Figure 1A:
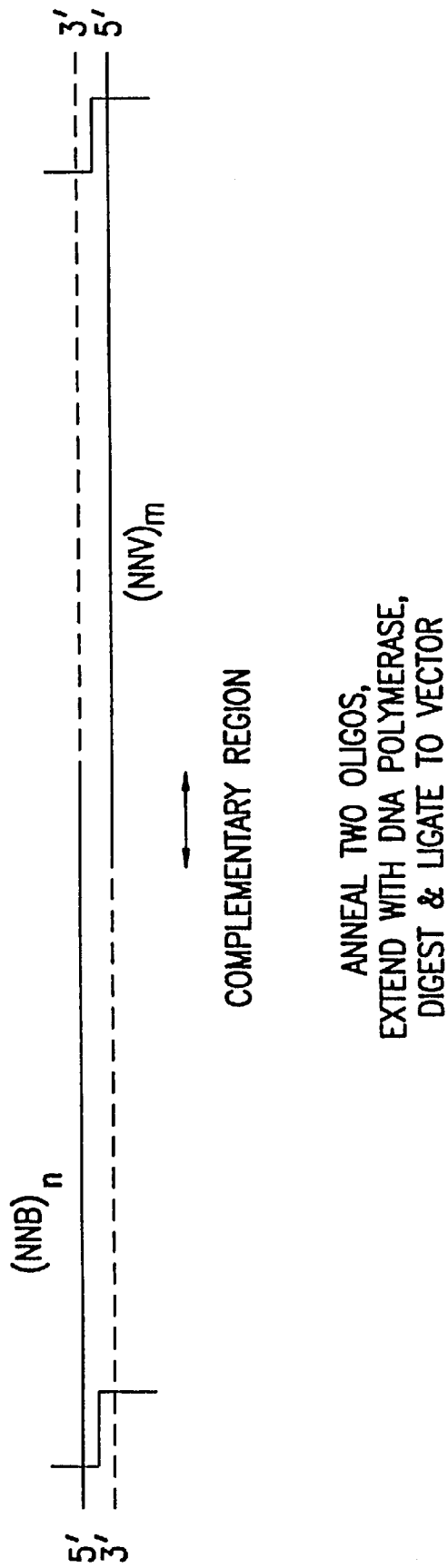
Figure 1B:
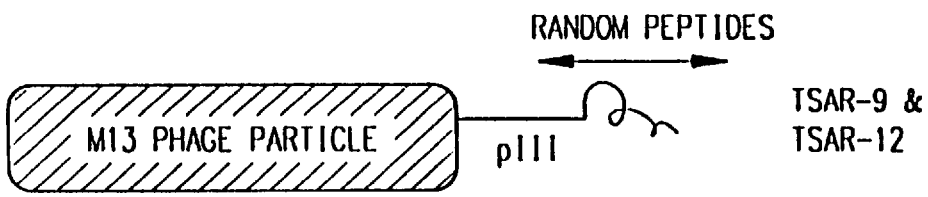
Figure 1C:
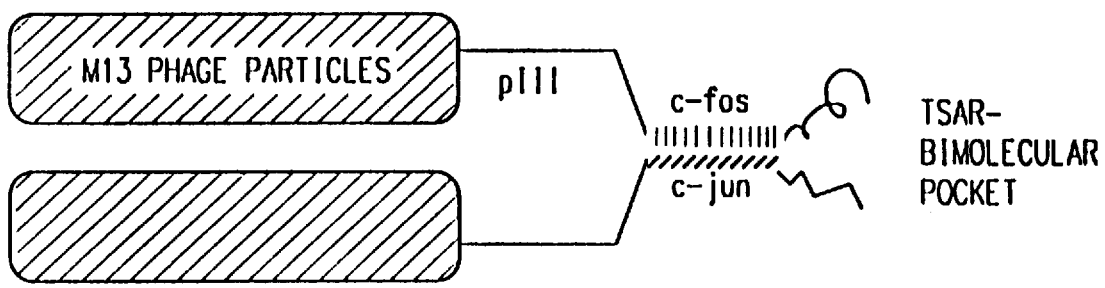

US005844076A

United States Patent [19]
Kay et al.

[11] Patent Number: 5,844,076
[45] Date of Patent: Dec. 1, 1998

[54] TOTALLY SYNTHETIC AFFINITY REAGENTS

[75] Inventors: Brian K. Kay; Dana M. Fowlkes, both of Chapel Hill, N.C.

[73] Assignee: The University of North Carolina at Chapel Hill, Chapel Hill, N.C.

[21] Appl. No.: 471,939

[22] Filed: Jun. 6, 1995

Related U.S. Application Data

[62] Division of Ser. No. 176,500, Dec. 30, 1993, Pat. No. 5,498,538, which is a continuation of Ser. No. 13,416, Feb. 1, 1993, abandoned, which is a continuation-in-part of Ser. No. 854,133, Mar. 19, 1992, abandoned, which is a continuation of Ser. No. 480,420, Feb. 15, 1990, abandoned.

[51] Int. Cl.$^6$ .................................................. A61K 38/04
[52] U.S. Cl. .................................................. 530/326
[58] Field of Search ........................................... 530/326

[56] References Cited

U.S. PATENT DOCUMENTS

| | | | |
|---|---|---|---|
| 4,522,918 | 6/1985 | Schlom et al. | 435/68 |
| 4,612,282 | 9/1986 | Schlom et al. | 435/7.23 |
| 4,732,864 | 3/1988 | Tolman | 424/1.45 |
| 4,769,326 | 9/1988 | Rutter | 435/68.1 |
| 5,096,815 | 3/1992 | Ladner et al. | 435/235.1 |
| 5,162,504 | 11/1992 | Horoszewicz | 530/388.2 |
| 5,198,346 | 3/1993 | Ladner et al. | 435/69.1 |
| 5,223,409 | 6/1993 | Ladner et al. | 435/69.7 |
| 5,270,170 | 12/1993 | Cull et al. | 435/7.37 |
| 5,403,484 | 4/1995 | Ladner et al. | 435/235.1 |

FOREIGN PATENT DOCUMENTS

| | | |
|---|---|---|
| 035384 | 9/1981 | European Pat. Off. . |
| 0244 221 | 11/1987 | European Pat. Off. . |
| 0371 820 | 6/1990 | European Pat. Off. . |
| 0383 620 A2 | 8/1990 | European Pat. Off. . |
| 59068A2 | 4/1994 | France . |
| 2 183 661 | 6/1982 | United Kingdom . |
| 2183661 | 6/1987 | United Kingdom . |
| WO 92/15679 | 9/1972 | WIPO . |
| WO 85/02909 | 7/1985 | WIPO . |
| WO 86/00991 | 2/1986 | WIPO . |
| WO 86/05803 | 10/1986 | WIPO . |
| WO 86/06487 | 11/1986 | WIPO . |
| WO 88/03168 | 5/1988 | WIPO . |
| WO 88/06630 | 9/1988 | WIPO . |
| WO 90/01035 | 2/1990 | WIPO . |
| WO 90/02809 | 3/1990 | WIPO . |
| WO 90/07862 | 7/1990 | WIPO . |
| WO 90/14430 | 11/1990 | WIPO . |
| WO 91/04329 | 4/1991 | WIPO . |
| WO 91/05058 | 4/1991 | WIPO . |
| WO 91/12328 | 8/1991 | WIPO . |
| WO 91/16912 | 11/1991 | WIPO . |
| WO 91/17271 | 11/1991 | WIPO . |
| WO 91/18980 | 12/1991 | WIPO . |
| WO 91/19818 | 12/1991 | WIPO . |
| WO 92/00091 | 1/1992 | WIPO . |
| WO 92/03461 | 3/1992 | WIPO . |
| WO 92/06176 | 4/1992 | WIPO . |
| WO 92/06191 | 4/1992 | WIPO . |
| WO 92/06204 | 4/1992 | WIPO . |
| WO 92/11272 | 7/1992 | WIPO . |
| WO 92/15677 | 9/1992 | WIPO . |
| WO 92/15702 | 9/1992 | WIPO . |

OTHER PUBLICATIONS

Alting–Mees et al., "pBluescript II: Gene Mapping Vectors", 1989, Nucl. Acid Res. 17(22):9494.

Amann et al., "Tightly Regulated tac Promoter Vectors Useful for the Expression of Unfused and Fused Proteins in *Escherichia coli*", 1988, Gene 69:301–315.

Anand, et al., "Bacterial Expression and Secretion of Various Single–Chain Fv Genes Encoding Proteins Specific for a Salmonella Serotype B O–Antigen", 1991, J. Biol. Chem. 266(32):21874–21879.

Appel, J.R., "Elucidation of Discontinuous Linear Determinants in Peptides", 1990, J. Immunol. 144(3):976–983.

Arkin and Youvan, "Optimizing Nucleotide Mixtures to Encode Specific Subsets of Amino Acids for Semi–Random Mutagenesis", 1992, Biotechnology 10:297–300.

Arnold, 1991, "Metal–Affinity Separations: A New Dimension in Protein Processing", Biotechnol. 9:151–156.

Baker et al., "A Gene Regulating the Heat Shock Response in *Escherichia coli* Also Affects Proteolysis", 1984, Proc. Natl. Acad. Sci. 81:6779–6783.

Baldwin et al., "Generation of a Catalytic Antibody by Site–Directed Mutagenesis", 1989, Science 245:1104–1107.

Barbas, et al., "Assembly of Combinatorial Antibody Libraries on Phage Surfaces: The Gene III Site", 1991, Proc. Natl. Acad. Sci. USA 88:7978–7982.

Barbas, et al., Semisynthetic Combinatorial Antibody Libraries: A Chemical Solution to the Diversity Problem, 1992, Proc. Natl. Acad. Sci. USA 89:4457–4461.

Barbas, et al., "Human Monoclonal Fab Fragments Derived From a Combinatorial Library Bind to Respiratory Syncytial Virus F Glycoprotein and Neutralize Infectivity", 1992, Proc. Natl. Acad. Sci. 89:10164–10168.

Barnett et al., "Carcinoembryonic Antigen Family: Characterization of cDNAs Coding for NCA and CEA and Suggestion of Nonrandom Sequence Variation in Their Conserved Loop–Domains", 1988, Genomics 3:59–66.

(List continued on next page.)

*Primary Examiner*—Cecilia J. Tsang
*Assistant Examiner*—Bennett Celsa
*Attorney, Agent, or Firm*—Pennie & Edmonds LLP

[57] ABSTRACT

A method for producing heterofunctional binding fusion proteins termed Totally Synthetic Affinity Reagents (TSARs) is disclosed. TSARs are concatenated heterofunctional proteins, polypeptides or peptides comprising at least two functional regions: a binding domain with affinity for a ligand and a second effector peptide portion that is chemically or biologically active. In one embodiment, the heterofunctional proteins, polypeptides or peptides further comprise a linker peptide portion between the binding domain and the second active peptide portion. The linker peptide can be either susceptible or not susceptible to cleavage by enzymatic or chemical means. Heterofunctional binding reagents as well as methods for using the reagents for a variety of in vitro and in vivo applications are also disclosed.

3 Claims, 20 Drawing Sheets

OTHER PUBLICATIONS

Barrett, et al., "Selective Enrichment and Characterization of High Affinity Ligands from Collections of Random Peptides on Filamentous Phage", 1992, Anal. Biochem. 204:357–364.

Bass, et al., "Hormone Phage: An Enrichment Method for Variant Proteins With Altered Binding Properties", 1990, Proteins 8:309–314.

Beaudry and Joyce, "Directed Evolution of an RNA Enzyme", 1992, Science 257:635–641.

Berg, "Potential Metal–Binding Domains in Nucleic Acid Binding Proteins", 1986, Science 232:485–487.

Berg, "Proposed Structure for the Zinc–Binding Domains from Transcription Factor IIIA and Related Proteins", 1988, Proc. Nat'l Acad. Sci. USA 85:99–102.

Berg, "Zinc Finger Domains: Hypotheses and Current Knowledge", 1990, Ann. Rev. Biophy. Biochem. 19:405–421.

Birnbaum and Mosbach, "Peptide Screening", 1992, Current Opinion in Biotechnology 3:49–54.

Blondelle, et al., "Evaluation of Peptide–Peptide Interactions Using Reversed–Phase High–Performance Liquid Chromatography", 1992, J. Chromatography 625:199–206.

Cabilly et al., "Generation of Antibody Activity From Immunoglobulin Polypeptide Chains Produced in *Escherichia coli*", 1984, Proc. Natl. Acad. Sci 81:3273–3277.

Chapman, et al., 1992, Biochemistry 31:12819–25.

Cesareni, G., "Peptide Display on Filamentous Phage Capsids—A New Powerful Tool to Study Protein–Ligand Interaction", 1992, FEBS Letters 307(1):66–70.

Chakrabarty et al., "Large Differences in the Helix Propensities of Alanine and Glycine", 1991, Nature 351:586–588.

Charbit, et al., "Summary—Expression of Foreign Peptides by Genetic Fusion in Bacteria and Bacteriophages", 1971, Bulletin de L Institut Pasteur 89(1):17–49 (Abstract only).

Charbit et al., "Versatility of a Vector for Expressing Foreign Polypeptides at the Surface of Gram–Negative Bacteria", 1988, Gene 70: 181–189.

Charbit, et al., "Permissive Sites and Topology of an Outer Membrane Protein with a Reporter Epitope", 1991, J. Bacteriol. 173(1):262–275.

Chaudhary et al., "A Rapid Method of Cloning Functional Variable–Region Antibody Genes in *Escherichia coli* as Single–Chain Immunotoxins", 1990, Proc. Natl. Acad. Sci. 87:1066–1070.

Cherny et al., "cDNA Sequence, Protein Structure, and Chromosomal Location of the Human Gene for Poly(ADP–ribose) Polymerase", 1987, Proc. Natl. Acad. Sci. 84:8370–8374.

Chien, et al., "Diagnosis of Hepatitis C Virus (HCV) Infection Using an Immunodominant Chimeric Polyprotein to Capture Circulating Antibodies: Reevaluation of the Role of HCV in Liver Disease", 1992, Proc. Natl Acad. Sci. USA 89:10011–10015.

Christian, et al., "Simplified Methods for Construction, Assessment and Rapid Screening of Peptide Libraries in Bacteriophage", 1992, J. Mol. Biol. 227:711–718.

Clackson, et al., "Making Antibody Fragments Using Phage Display Libraries", 1991, Nature 352:624–628.

Clement and Hofnung, "Gene Sequence of the λ Receptor, an Outer Membrane Protein of *E. coli* K12", 1981, Cell 27: 507–514.

Clement et al., "Bacterial Vectors to Target and/or Purify Polypeptides: Their Use in Immunological Studies", 1991, Ann. Bio. Clin. 49:249–254.

Clement et al., "Molecular and Cellular Targeting in the Expression of Foreign Polypeptides in Bacteria", 1992, Antonie van Leeuwenhoek 61:143–152.

Collet, et al., "A Binary Plasmid System for Shuffling Combinatorial Antibody Libraries", Nov. 1992, Proc. Natl. Acad. Sci. 89:10026–10030.

Crissman and Smith, "Gene–III Protein of Filamentous Phages: Evidence for a Carboxyl–Terminal Domain with a Role in Morphogenesis", 1984, Virology 132:445–455.

Cull et al., "Screening for Receptor Ligands Using Large Libraries of Peptides Linked to the C Terminus of the lac Repressor", 1992, Proc. Natl. Acad. Sci. USA 89:1865–1869.

Cwirla, et al., "Peptides on Phage: A Vast Library of Peptides for Identifying Ligands", 1990, Proc. Natl. Acad. Sci. USA 87:6378–6382.

De la Cruz, et al., "Immunogenicity and Epitope Mapping of Foreign Sequences Via Genetically Engineered Filamentous Phage", 1988, J. Biol. Chem. 263:4318–4322.

Derbyshire et al., "A Simple and Efficient Procedure for Saturation Mutagenesis Using Mixed Oligodeoxynucleotides", 1986, Gene 46:145–152.

Devlin, et al., "Random Peptide Libraries: A Source of Specific Protein Binding Molecules", 1990, Science 249:404–406.

Dower, et al., "The Search for Molecular Diversity (II): Recombinant and Synthetic Randomized Peptide Libraries", 1991, Ann. Rep. Med. Chem. 26:271–279.

Dunn et al., 1988, Protein Eng. 2:283–291.

Evan et al., "Isolation of Monoclonal Antibodies Specific for Human c–myc Proto–Oncogene Product", 1985, Mol. Cell. Biol. 5:3610–3616.

Evans, "The Steroid and Thyroid Hormone Receptor Superfamily", 1988, Nature 240:889–895.

Feild, et al., "Structure–Function Analysis of Human Transforming Growth Factor–α by Site–Directed Mutagenesis", 1992, J. Biochem. 283:91–98.

Felici, F., "Selection of Antibody Ligands from a Large Library of Oligopeptides Expressed on a Multivalent Exposition Vector", 1991, J. Mol. Biol. 222:301–310.

Fields et al., "A Novel Genetic System to Detect Protein–Protein Interactions", 1989, Nature 340:245–246.

Fieser, T.M. et al., "Influence of Protein Flexibility and Peptide Conformation on Reactivity of Monoclonal Anti–Peptide Antibodies with a Protein α–Helix", 1987, Proc. Natl. Acad. Sci. 84:8568–8572.

Fodor, et al., "Light–Directed, Spatially Addressable Parallel Chemical Synthesis", 1991, Science 251:767–773.

Fowlkes et al., "Multipurpose Vectors for Peptide Expression on the M13 Viral Surface", 1992, BioTechniques, 13:422–427.

Garrard et al., "Fab Assembly and Enrichment in a Monovalent Phage Display System", 1991, Biotechnol. 9:1373–1377.

Geisow, M.J., "Improved Selection Systems for Man–Made Antibodies", 1992, TIBTECH 10:75–76.

Germino et al., "Use of Gene Fusions and Protein–Protein Interaction in the Isolation of a Biologically Active Regulatory Protein: The Replication Initiator Protein of Plasmid R6K", 1983, Proc. Natl. Acad. Sci. USA 80:6848–6852.

Germino and Bastia, "Rapid Purification of a Cloned Gene Product by Genetic Fusion and Site–Specific Proteolysis", 1984, Proc. Natl. Acad. Sci. USA 81:4692–4696.

Geysen, H.M., "A Priori Delineation of a Peptide Which Mimics a Discontinuous Antigenic Determinant", 1986, Mol. Immun. 23(7):709–715.

Geysen, et al., "The Delineation of Peptides Able to Mimic Assembled Epitopes", 1986, Synthetic Peptides as Antigens, Wiley, Chichester (Ciba Foundation Symposium 119):130–149.

Geysen, et al., "Cognitive Features of Continuous Antigenic Determinants", 1988, J. Mol. Recog., 1:32–41.

Geysen, et al., 1988, "Mimotopes—Mimics of Antibody Epitopes", Molecular Mimicry in Health & Diseases (ed.), vol. 2 pp. 102–110, Elsevier Pub., Nordisk—Insulin Symposium No. 2, Amsterdam.

Giguere, et al., "Identification of a Receptor for the Morphogen Retinoic Acid", 1987, Nature 330:624–629.

Glaser et al., "Antibody Engineering by Codon–Based Mutagenesis in a Filamentous Phage Vector System", 1992, J. Immunol. 149(12):3903–3913.

Gluckman, et al., "Three–Dimensional Structure of a Cloning Vector—X-ray Diffraction Studies of Filamentous Bacteriophage M13 at 7 Å Resolution", 1992, J. Mol. Biol. 226:455–470.

Graf et al., "Identification of an Amino Acid Sequence in Laminin Mediating Cell Attachment, Chemotaxis, and Receptor Binding", 1987, Cell 48:989–996.

Gram et al., "In vitro Selection and Affinity Maturation of Antibodies from a Naive Combinatorial Immunoglobulin Library", 1992, Proc. Natl. Acad. Sci. USA 89:3576–3580.

Green et al., "Oestradiol Induction of a Glucocorticoid–Responsive Gene by a Chmaeric Receptor", 1987, Nature 325:75–77.

Greenwood, et al., "Multiple Display of Foreign Peptides on a Filamentous Bacteriophage—Peptides from *Plasmodium falciparum* Circumsporozoite Protein as Antigens", 1991, J. Mol. Biol. 220:821–827.

Grill et al., "Phytochelatins: The Principal Heavy–Metal Complexing Peptides of Higher Plants", 1985, Science 230:674–676.

Grossman et al., "The htpR Gene Produce of *E. coli* is a Sigma Factor for Heat–Shock Promoters", 1984, Cell 38:383–390.

Guarente et al., "Improved Methods for Maximizing Expression of a Cloned Gene: a Bacterium That Synthesizes Rabbit β–Globin", 1980, Cell 20:543–553.

Hammer, et al., "Identification of a Motif for HLA–DR1 Binding Peptides Using M13 Display Libraries", 1992, J. Exp. Med. 176:1007–1013.

Hawkins, R.E., "Selection of Phage Antibodies by Binding Affinity—Mimicking Affinity Maturation", 1992, J. Mol. Biol. 226:889–896.

Hawkins, et al., "Adapting Antibodies for Clinical Use", 1992, British Med. Journal 305:1348–1352.

Hemdan, et al., "Surface Topography of Histidine Residues: A Facile Probe by Immobilized Metal Ion Affinity Chromatography" 1989, Proc. Nat'l Acad. Sci. USA 86:1811–1815.

Honzatko et al., "Crystal and Molecular Structures of Native and CTP–Liganded Aspartate Carbamoyltransferase from *Escherichia coli*", 1982, J. Mol. Biol. 160:219–263.

Hoogenboom et al., "Multi–Subunit Proteins on the Surface of Filamentous Phage: Methodologies for Displaying Antibody (Fab) Heavy and Light Chains", 1991; Nucl. Acids. Res. 19:4133–4137.

Hoogenboom and Winter, "By–Passing Immunization—Human Antibodies from Synthetic Repertoires of Germline $V_h$ Gene Segments Rearranged in vitro", 1992, J. Mol. Biol. 227:381–388.

Horwitz and Loeb, 1986, Proc. Natl. Acad. Sci. USA 83:7405–7409.

Houghton et al., "The Use of Synthetic Peptide Combinatorial Libraries for the Identification of Bioactive Peptides", 1992, Biotechniques 13(3):412–421.

Houghten, et al., "Generation and Use of Synthetic Peptide Combinatorial Libraries for Basic Research ad Drug Discovery", 1991, Nature 354:84–86.

Hunkapiller et al., "A Microchemical Facility for the Analysis and Synthesis of Genes and Proteins", 1984, Nature 310:105–111.

Huse, et al., "Generation of a Large Combinatorial Library of the Immunoglobulin Repertoire in Phage Lambda", 1989, Science 246:1275–1281.

Huse, et al., "Application of a Filamentous Phage pVIII Fusion Protein System Suitable for Efficient Production, Screening, and Mutagenesis of F(ab) Antibody Fragments", 1992, J. Immunol 149(12):3914–3920.

Hutchinson et al., "A Complete Library of Point Substitution Mutations in the Glucocorticoid Response Element of Mouse Mammary Tumor Virus", 1986, Proc. Natl. Acad. Sci. 83:710–714.

Huynh et al., 1985, Glover ed., DNA Cloning: A Practical Approach, vol. 1, IRL Press, pp. 49–78.

Ikura, et al., 1992, Cell Calcium 13:391–400.

Israeli, et al., "Molecular Cloning of a Complementary DNA Encoding a Prostrate–Specific Membrane Antigen", 1993, Cancer Research 53:227–230.

Jones et al., "Replacing the Complementarity–Determining Regions in a Human Antibody With Those From a Mouse", 1986, Nature 321:522–525.

Joyce, G.F., "Directed Molecular Evolution", 1992, Scientific American, Dec. 1992 267(6):90–97.

Jurnak, "Structure of the GDP Domain of EF-Tu and Location of the Amino Acids Homologous to ras Oncogene Proteins", 1985, Science 230:32–36.

Kang et al., "Linkage of Recognition and Replication Functions by Assembling Combinatorial Antibody Fab Libraries Along Phage Surfaces", 1991, Proc. Nat'l Acad. Sci. USA 88:4363–4366.

Kauffman, S.A., "Applied Molecular Evolution", 1992 J. Theor. Biol. 157:1–7.

Kay et al., 1993, "An M13 phage library displaying random 38–amino–acid peptides as a source of novel sequences with affinity to selected targets," Gene 128:58–65.

Kemp and Cowman, 1981, Proc. Natl. Acad. Sci. USA 78:4520–4524.

Kleina et al., "Construction of *Escherichia coli* Amber Suppressor tRNA Genes", 1990, J. Mol. Biol. 213:705–717.

Klein, et al., "Effects of Signal Peptide Changes on the Secretion of Bovine Somatotropin (bST) from *Escherichia coli*", 1992, Protein Engineering 5(6):511–517.

Kostelny et al., "Formation of a Bispecific Antibody by the Use of Leucine Zippers", 1992, J. Immunol. 148:1547–1553.

Kretsinger et al., "Carp Muscle Calcium–Binding Protein", 1973, J. Biol. Chem. 248:3313.

la Cour et al., "Structural Details of the Binding of Guanosine Diphosphate to Elongation Factor Tu From *E. coli* as Studied by X-ray Crystallography", 1985, EMBO J. 4:2385–2388.

Lam, K., et al., "A New Type of Synthetic Peptide Library for Identifying Ligand–Binding Activity", 1991, Nature 354:82–84.

Langen and Taylor, "Alkaline Phosphatase–Somatostatin Hybrid Proteins as Probes for Somatostatin–Receptors", 1992, Proteins: Structure, Function and Genetics 14:1–9.

Landschultz et al., "The Leucine Zipper: A Hypothetical Structure Common to a New Class of DNA Binding Proteins", 1988, Science 240:1759.

Lemire et al., "The Mitochondrial Targeting Function of Randomly Generated Peptide Sequences Correlates With Predicted Helical Amphiphilicity", 1989, J. Biol. Chem. 264:20206–20215.

Lenstra, et al., "Isolation of Sequences from a Random–Sequence Expression Library That Mimic Viral Epitopes", 1992, J. Immunol Meth. 152:149–157.

Lerner, R.A., "Antibodies Without Immunization", 1992, Science 258:1313–1314.

Lowman et al., "Selecting High–Affinity Binding Proteins by Monovalent Phage Display", 1991, Biochemistry 30:10832–10838.

Lowman, "Monovalent Phage Display: A Method for Selecting Variant Proteins from Random Libraries", 1991, Methods 3:205–216.

Maeji et al., "Peptide Research—Systematic Screening for Bioactive Peptides", 1991, Peptide Res. 4(3):142–146.

Mandecki, W., "A Method for Construction of Long Randomized Open Reading Frames and Polypeptides", 1990, Protein Engineering 3(3):221–226.

Mannhold and Timmerman, 1992, Pharm. Weekbl.–Sci. 14(4):161–166.

Markland et al., "Design, Construction and Function of a Multicopy Display Vector Using Fusions to the Major Coat Protein for Bacteriophage M13", 1991, Gene 109:13–19.

Marks, et al., "By–Passing Immunization: Building High Affinity Human Antibodies by Chain Shuffling", 1992, Biotechnology 10:779–783.

Marks, et al., "Molecular Evaluation of Proteins on Filamentous Phage", 1992, J. Biol. Chem. 267(23):16007–16010.

Marks et al., "By–Passing Immunization—Human Antibodies from V–gene Libraries Displayed on Phage", 1991 J. Mol. Biol. 222:581–597.

Martineau, et al., "A Genetic System to Elicit and Monitor Anti–Peptide Antibodies Without Peptide Synthesis", 1991, Biotechnology 9:170–172.

Martineau et al., "Expression of Heterologous Peptides at Two Permissive Sites of the MalE Protein" Antigenicity and Immunogenicity of Foreign B–cell and T–cell Epitopes, 1992, Gene 113:35–46.

Matteucci et al., "Targeted Random Mutagenesis: The Use of Ambiguously Synthesized Oligonucleotides to Mutagenize Sequences Immediately 5'1 of an ATG Initiation Codon", 983, Nucl. Acids Res. 11:3113.

McCafferty et al., "Phage Antibodies: Filamentous Phage Displaying Antibody Variable Domains", 1990, Nature 348:552–554.

McCafferty et al., "Phage–Enzymes: Expression and Affinity Chromatography of Functional Alkaline Phosphatase on the Surface of Bacteriophage", 1991, Protein–Eng, 4:955–961.

McCormick et al., "A Model for the Tertiary Structure of p. 21, the Product of the ras Oncogene", 1985, Science 230:78–82.

McNeil et al., "*Saccharomyces cerevisiae CYC1* mRNA 5'–End Positioning: Analysis by In Vitro Mutagenesis, Using Synthetic Duplexes With Random Mismatch Base Pairs", 1985, Mol. Cell Biol. 5:3545.

Meador, et al., 1992, Science 257:1251–55.

Means, et al., 1991, Adv. Exp. Med. Biol. 304:11–24.

Merutka et al., "A Model Peptide With Enhanced Helicity", 1991, Biochem. 30:4245–4248.

Messing, "Cloning in M13 Phage or How to Use Biology at its Best", 1991, Gene 100:3–12.

Metallothioneins, "Metallothionein and Other Low Molecular Weight Metal–Binding Proteins", 1979, pp. 46–92 eds. Kagi and Nordberg, Birkhauser Verlag Basel.

Miller et al., "Repetitive Zinc–Binding Domains in the Protein Transcription Factor IIIA From *Xenopus* Oocytes", 1985, EMBO J. 4:1609.

Min et al., 1988, Nucleic Acids Res. 16:5075–5088.

Morrison et al., "Chimeric Human Antibody Molecules: Mouse Antigen–Binding Domains With Human Constant Region Domains", 1984, Proc. Natl. Acad. Sci. 81:6851.

Morrison, "Transfectomas Provide Novel Chimeric Antibodies", 1985, Science 229:1202–1207.

Nagai et al., "Generation of β–globin by Sequence–specific Proteolysis of a Hybrid Protein Produced in *Escherichia coli*", 1984, Nature 309:810–812.

Nakamura et al., "Two Types of Linkage Between Codon Usage and Gene–Expression Levels", 1991, FEBS Lett. 289:123–125.

Neuberger et al., "Recombinant–Antibodies Possessing Novel Effector Functions", 1984, Nature 312:604–608.

Oldenburg et al., "Peptide Ligands for a Sugar–Binding Protein Isolated From a Random Peptide Library", 1992, Proc. Natl. Acad. Sci. USA 89:5393–5397.

Oliphant et al., "Cloning of Random–Sequence Oligodeoxynucleotides", 1986, Gene 44:177–183.

Olivera, et al., "Conotoxins", 1991, J. Biol. Chem. 266(33):22067–22070.

O'Neil, et al., "Identification of Novel Peptide Antagonists for GPIIB/IIIa from a Conformationally Constrained Phage Peptide Library", 1992, PROTEINS: Structure, Function and Genetics 14:509–515.

O'Shea et al., "Mechanism of Specificity in the Fos–Jun Oncoprotein Heterodimer", 1992, Cell. 68:699–708.

Pabo and Sauer, "Protein–DNA Recognition", 1984, Ann. Rev. Biochem. 53:293–321.

Parmley and Smith, "Antibody–Selectable Filamentous fd Phage Vectors: Affinity Purification of Target Genes", 1988, Gene 73:305–318.

Parmley and Smith, "Filamentous Fusion Phage Cloning Vectors for the Study of Epitopes and Design of Vaccines", 1989, Adv. Exp. Med. Biol. 251:215–218.

Payne, et al., 1988, J. Biol. Chem. 263:7190–95.

Persechini and Kretsinger, 1988, J. Cardiovasc. Pharmacol. 12:S1–12.

Pinilla, C., "Rapid Identification of High Affinity Peptide Ligands Using Positional Scanning Synthetic Peptide Combinatorial Libraries", 1992, Biotechniques 13(6):901–905.

Pytela et al., "Identification and Isolation of a 140 kd Cell Surface Glycoprotein With Properties Expected of a Fibronectin Receptor", 1985, Cell 40:191–198.

Pytela et al., "Platelet Membrane Glycoprotein IIb/IIIa: Member of a Family of Arg–Gly–Asp—Specific Adhesion Receptors", 1986, Science 231:1559–1562.

Query et al., "A Common RNA Recognition Motif Identified Within a defined U1 RNA Binding Domain of the 70K U1 snRNP Protein", 1989, Cell 57:89–101.

Rao and Rossmann, "Comparison of Super–Secondary Structures in Proteins", 1973, J. Mol. Biol. 76:241.

Rebar and Pabo, 1993, Science, 263:671–73.

Reidhaar–Olson et al., "Combinatorial Cassette Mutagenesis as a Probe of the Informational Content of Protein Sequences", 1988, Science 241:53–57.

Riechmann et al., "Expression of an Antibody Fv Fragment in Myeloma Cells", 1988, J. Mol. Biol 203:825.

Roberts, et al., "Protease Inhibitor Display M13 Phage: Selection of High–Affinity Neutrophil Elastase Inhibitors", 1992, Gene 121(1):9–15.

Roberts et al., "Directed Evolution of a Protein: Selection of Potent Neutrophil Elastase Inhibitors Displayed on M13 Fusion Phage", 1992, Proc. Natl. Acad. Sci. USA 89:2429–2433.

Rosenstraus et al., "Carbohydrate–derivatized Immunoconjugate of the Anti–(Carcinoembryonic Antigen) Monoclonal Antibody C46: Immunohistological Reactivity and Pharmacokinetic Comparison With a Randomly Derivatized C46 Immunoconjugate", 1990, Cancer Immunol. Immunother. 32:207–213.

Ruoslahti et al., "Arg–Gly–Asp: A Versatile Cell Recognition Signal", 1986, Cell 44:517–518.

Ruoslahti et al., "New Perspectives in Cell Adhesion: RGD and Integrins", 1987, Science 238:491.

Russel, M., "Filamentous Phage Assembly", 1991, Molecular Microbiology 5:1607–1613 (Abstract Only).

Sacks et al., "Molecular Mimicry of a Carbohydrate Epitope on a Major Surface Glycoprotein of *Trypanosoma cruzi* by Using Anti–idiotypic Antibodies", 1985, J. Immunol. 135:4155–4159.

Sambrook, Fritsch, and Maniatis, "Analysis and Cloning, of Eukaryotic Genomic NDA," Chapter 9 in Cloning, A Laboratory Manual, 2d ed., Cold Spring Harbor Laboratory Press, pp. 9.2–9.62.

Sambrook, Fritsch, and Maniatis, "Construction and Analysis of cDNA Libraries," Chapter 8 in Cloning, A Laboratory Manual, ed ed., Cold Spring Harbor Laboratory Press, 1989, pp. 8.2–8.86.

Sambrook, Fritsch, and Maniatis, "Screening Expression Libraries with Antibodies and Oligonucleotides," Chapter 12 in Cloning, A Laboratory Manual, 2d ed., Cold Spring Harbor Laboratory Press, 1989, pp. 12.2–12.44.

Sambrook, Fritsh and Maniatis, "Choosing a Bacterial Host for Bacteriophage λ Vectors", Molecular Cloning: A Laboratory Manual, 2d. ed. Cold Spring Harbor Laboratory Press, pp. 2.55, 2.57–.59, 4.13–4.15 1989.

Sanger, "DNA Sequencing With Chain–Terminating Inhibitors", 1979, Proc. Nat'l. Acad. Sci. USA 74:5463–5467.

Saragori, H.U., "Loops and Secondary Structure Mimetics: Development and Applications in Basic Science and Rational Drug Design", 1992, Biotechnology 10:773–778.

Schneider and Stormo, 1989, Nucleic Acids Res. 17:659–674.

Schoner et al., "Translation of a Synthetic Two–Cistron mRNA in *Escherichia coli*", 1986, Proc. Nat'l. Acad. Sci. 83:8506–8510.

Schumacher et al., "Synthetic Peptide Libraries in the Determination of T Cell Epitopes and Peptide Binding Specificity of Class I Molecules", 1992, Eur. J. Immunol. 22:1405–1418.

Scott and Smith, "Searching for Peptide Ligands With an Epitope Library", 1990, Science 249:386–390.

Scott et al., "A Family of Concanavalin A–Binding Peptides From a Hexapeptide Epitope Library", 1991, Proc. Natl. Acad. Sci. USA 89:5398–5402.

Scott, J.K., "Discovering Peptide Ligands Using Epitope Libraries", 1992, TIB 517:241–245.

Sharma et al., "Calcium Ion Binding to δ– and to β–Crystallins", 1989, J. Biol. Chem. 264:12794–12799.

Simon, et al., "Peptoids: A Modular Approach to Drug Discovery", 1992, Proc. Natl. Acad. Sci. 89:9367–9371.

Smith, G.P., "Filamentous Fusion Phage: Novel Expression Vectors That Display Cloned Antigens on the Virion Surface", 1985, Science 228:1315–1317.

Smith, G.P., "Surface Presentation of Protein Epitopes Using Bacteriophage Expression Systems", 1991, Cur. Opin. Biotech. 2:668–673.

Snouwaert et al., "Large Numbers of Random Point and Cluster Mutations Within the Adenovirus VA I Gene Allow Characterization of Sequences Required for Efficient Transcription", 1987, Nucl. Acids Res. 15:8293–8303.

Sominskaya, I., "Tetrapeptide QDPR is a Minimal Immunodominant Epitope Within the preS2 Domain of Hepatitis B Virus", 1992, Immunol. Lett. 33:169–172.

Sondek et al., "A General Strategy for Random Insertion and Substitution Mutagenesis: Substoichiometric Coupling of Trinucleotide Phosphormidities", 1992, Proc. Nat'l Acad. Sci. USA 89:3581–3585.

Stephen and Lane, "Mutant Conformation of p53—Precise Epitope Mapping Using a Filamentous Phage Epitope Library", 1992, J. Mol. Biol. 255:577–583.

Swimmer et al., "Phage Display of Ricin B Chain and its Single Binding Domains: System for Screening Galactose––Binding Mutants", 1992, Proc. Natl. Acad. Sci. USA 89:3756–3760.

Vasavada et al., "A Contingent Replication Assay for the Detection of Protein–Protein Interactions in Animal Cells", 1991, Proc. Natl. Acad. Sci. USA 88:10686–10690.

Weber, et al., "Crystal Structure and Ligand–Binding Studies of a Screened Peptide Complexed With Streptavidin", 1992, Biochemistry 31:9350–9354.

Wells et al., "Cassette Mutagenesis: an Efficient Method for Generation of Multiple Mutations at Defined Sites", 1985, Gene 34:315.

Wells et al., "Rapid Evolution of Peptide and Protein Binding Properties in vitro", 1992, Current Opinion Struct'l Biol. 2:597–604.

Wetzel, R., "Learning From the Immune System: Laboratory Methods for Creating and Refining Molecular Diversity in Polypeptides", 1991, Protein Engineering 4(4):371–374.

Williams et al., "Production of Antibody–Tagged Enzymes by Myeloma Cells: Application to DNA Polymerase I Klenow Fragment", 1986, Gene 43:319–324.

Yip, et al., "Evaluation of the Interaction of Peptides with Cu(II), Ni(II), and Zn(II) by High–Performance Immobilized Metal Ion Affinity Chromatography", 1989, Anal. Biochem. 183:159–171.

Young and Davis, 1983, Proc. Natl. Acad. Sci. USA 80:1194–1198.

Zhang et al., "Low–Usage Codons in *Escherichia coli*, Yeast, Fruit Fly and Primates", 1991, Gene 105:61–72.

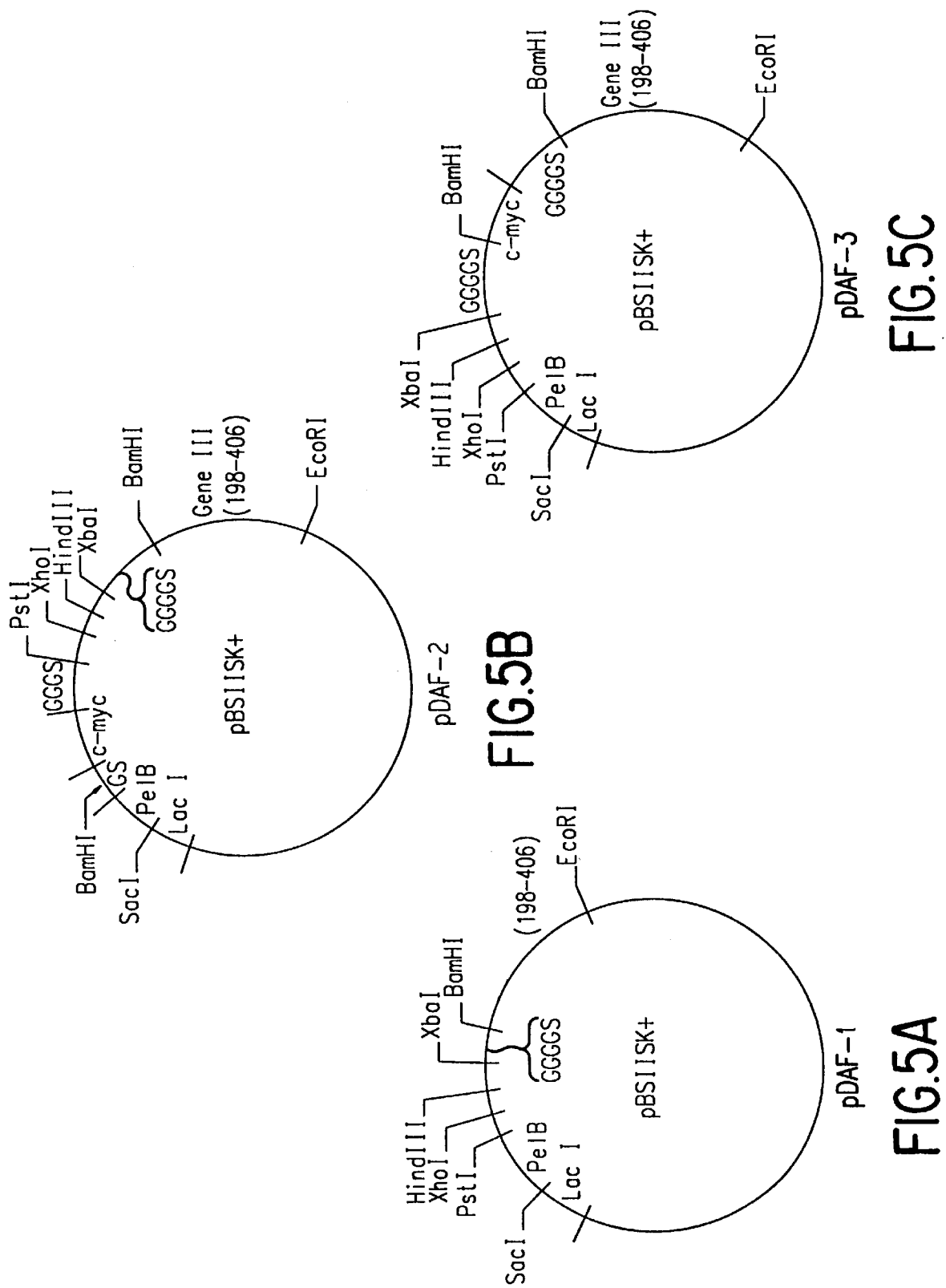

SEQUENCE LISTING ( 1 ) GENERAL INFORMATION:

( i i i ) NUMBER OF SEQUENCES: 141

( 2 ) INFORMATION FOR SEQ ID NO:1:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:1:

```
Gly Pro Val Lys Lys Ile Cys Ala Arg Asp Asn Ser Ala Arg Gly Asp
 1               5                  10                  15
Asn Asp Pro Gly Leu His Asn Gly Ser Ser Val His Val Ser Gly Thr
             20                  25                  30
Leu Ser Cys Asn Gln Tyr
             35
```

( 2 ) INFORMATION FOR SEQ ID NO:2:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:2:

```
Ser Thr Val Val Asp Ala Cys Thr Arg Tyr Ala Asn His Arg Ala Leu
 1               5                  10                  15
Ser Pro Gly Leu Asn Arg Arg Glu Val Asn Met Ala Asp Gly His Val
             20                  25                  30
Tyr Cys Asn His Val Xaa
             35
```

( 2 ) INFORMATION FOR SEQ ID NO:3:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:3:

```
His Cys Ile Gly Val Ile Ser Ser Asn Glu His Asn Cys Cys Asp Ser
 1               5                  10                  15
Trp Pro Pro Gly Ser Gly Asn Phe Ser His Asp Ser Cys Gln Gly Ala
             20                  25                  30
Ala Pro Asp Glu Pro Ser
             35
```

( 2 ) INFORMATION FOR SEQ ID NO:4:

( i ) SEQUENCE CHARACTERISTICS:
        ( A ) LENGTH: 38 amino acids
        ( B ) TYPE: amino acid
        ( C ) STRANDEDNESS: single (D) TOPOLOGY: unknown (ii) MOLECULE TYPE: peptide (xi) SEQUENCE DESCRIPTION: SEQ ID NO:4:

| Asn | Asp | Asn | Arg | Trp | Phe | Asn | Leu | Tyr | Gly | Asp | Ser | Asn | Ile | Pro | Gly |
|---|---|---|---|---|---|---|---|---|---|---|---|---|---|---|---|
| 1 | | | | 5 | | | | | 10 | | | | | 15 | |

| Cys | Ile | Pro | Gly | Phe | Pro | Thr | His | Ile | Leu | Arg | Glu | Gly | Val | Thr | Phe |
|---|---|---|---|---|---|---|---|---|---|---|---|---|---|---|---|
| | | | 20 | | | | 25 | | | | | 30 | | | |

Ala Asp His Val Cys Ser
              35

(2) INFORMATION FOR SEQ ID NO:5:

(i) SEQUENCE CHARACTERISTICS:
(A) LENGTH: 38 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:5:

| Asp | Phe | Arg | Leu | Glu | Leu | Val | Arg | Ser | Ser | Arg | Cys | Ser | Gln | Asp | Phe |
|---|---|---|---|---|---|---|---|---|---|---|---|---|---|---|---|
| 1 | | | | 5 | | | | | 10 | | | | | 15 | |

| Ile | Ser | Pro | Gly | Leu | Ser | Ala | Phe | Arg | Ala | Ser | Cys | Gln | Phe | Pro | Leu |
|---|---|---|---|---|---|---|---|---|---|---|---|---|---|---|---|
| | | | 20 | | | | | 25 | | | | | 30 | | |

Asp Thr Gln Ile Ser Pro
              35

(2) INFORMATION FOR SEQ ID NO:6:

(i) SEQUENCE CHARACTERISTICS:
(A) LENGTH: 11 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:6:

| Glu | Gln | Lys | Leu | Ile | Ser | Glu | Glu | Asp | Leu | Asn |
|---|---|---|---|---|---|---|---|---|---|---|
| 1 | | | | 5 | | | | | 10 | |

(2) INFORMATION FOR SEQ ID NO:7:

(i) SEQUENCE CHARACTERISTICS:
(A) LENGTH: 1323 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:7:

```
GTGAAAAAAT TATTATTCGC AATTCCTTTA GTTGTTCCTT TCTATTCTCA CTCCTCGAGA        60
GAGCAGAAAC TGATCTCTGA AGAAGACCTG AACTCTAGAC CTTCGAGAAC TGTTGAAAGT       120
TGTTTAGCAA AACCCCATAC AGAAAATTCA TTTACTAACG TCTGGAAAGA CGACAAAACT       180
TTAGATCGTT ACGCTAACTA TGAGGGTTGT CTGTGGAATG CTACAGGCGT TGTAGTTTGT       240
ACTGGTGACG AAACTCAGTG TTACGGTACA TGGGTTCCTA TTGGGCTTGC TATCCCTGAA       300
AATGAGGGTG GTGGCTCTGA GGGTGGCGGT TCTGAGGGTG GCGGTTCTGA GGGTGGCGGT       360
ACTAAACCTC CTGAGTACGG TGATACACCT ATTCCGGGCT ATACTTATAT CAACCCTCTC       420
```

| | | | | | |
|---|---|---|---|---|---|
| GACGGCACTT | ATCCGCCTGG | TACTGAGCAA | AACCCCGCTA | ATCCTAATCC | TTCTCTTGAG | 480 |
| GAGTCTCAGC | CTCTTAATAC | TTTCATGTTT | CAGAATAATA | GGTTCCGAAA | TAGGCAGGGG | 540 |
| GCATTAACTG | TTTATACGGG | CACTGTTACT | CAAGGCACTG | ACCCCGTTAA | AACTTATTAC | 600 |
| CAGTACACTC | CTGTATCATC | AAAAGCCATG | TATGACGCTT | ACTGGAACGG | TAAATTCAGA | 660 |
| GACTGCGCTT | TCCATTCTGG | CTTTAATGAA | GATCCATTCG | TTTGTGAATA | TCAAGGCAA | 720 |
| TCGTCTGACC | TGCCTCAACC | TCCTGTCAAT | GCTGGCGGCG | GCTCTGGTGG | TGGTTCTGGT | 780 |
| GGCGGCTCTG | AGGGTGGTGG | CTCTGAGGGT | GGCGGTTCTG | AGGGTGGCGG | CTCTGAGGGA | 840 |
| GGCGGTTCCG | GTGGTGGCTC | TGGTTCCGGT | GATTTTGATT | ATGAAAAGAT | GGCAAACGCT | 900 |
| AATAAGGGGG | CTATGACCGA | AAATGCCGAT | GAAAACGCGC | TACAGTCTGA | CGCTAAGGC | 960 |
| AAACTTGATT | CTGTCGCTAC | TGATTACGGT | GCTGCTATCG | ATGGTTTCAT | TGGTGACGTT | 1020 |
| TCCGGCCTTG | CTAATGGTAA | TGGTGCTACT | GGTGATTTTG | CTGGCTCTAA | TTCCCAAATG | 1080 |
| GCTCAAGTCG | GTGACGGTGA | TAATTCACCT | TTAATGAATA | ATTTCCGTCA | ATATTACCT | 1140 |
| TCCCTCCCTC | AATCGGTTGA | ATGTCGCCCT | TTTGTCTTTA | GCGCTGGTAA | ACCATATGAA | 1200 |
| TTTTCTATTG | ATTGTGACAA | AATAAACTTA | TTCCGTGGTG | TCTTTGCGTT | TCTTTTATAT | 1260 |
| GTTGCCACCT | TTATGTATGT | ATTTTCTACG | TTTGCTAACA | TACTGCGTAA | TAAGGAGTCT | 1320 |
| TAA | | | | | | 1323 |

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:8:

CATGGCTCGA GGCTGAGTTC TAGA　　　　　　　　　　　　　　　　　　　　　　　　24

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:9:

GATCTCTAGA ACTCAGCCTC GAGC　　　　　　　　　　　　　　　　　　　　　　　　24

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:10:

Cys Xaa Xaa Cys Xaa Xaa Xaa Xaa His Xaa Xaa Xaa Xaa Cys
 1               5                          10

( 2 ) INFORMATION FOR SEQ ID NO:11:

( i ) SEQUENCE CHARACTERISTICS:
( A ) LENGTH: 21 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:11:

Cys Xaa Xaa Cys Xaa Xaa Xaa Xaa Xaa Xaa Xaa Xaa Xaa Xaa Xaa
1               5                           10                          15

Xaa Cys Xaa Xaa Cys
        20

( 2 ) INFORMATION FOR SEQ ID NO:12:

( i ) SEQUENCE CHARACTERISTICS:
( A ) LENGTH: 17 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:12:

Cys Xaa Xaa Cys Xaa Xaa Xaa Xaa Xaa Xaa Xaa Xaa Xaa Cys Xaa Xaa
1               5                           10                          15

Cys ( 2 ) INFORMATION FOR SEQ ID NO:13:

( i ) SEQUENCE CHARACTERISTICS:
( A ) LENGTH: 21 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:13:

Cys Xaa Xaa Cys Xaa Xaa Xaa Xaa Xaa Xaa Xaa Xaa Xaa Xaa Xaa
1               5                           10                          15

Xaa His Xaa Xaa His
        20

( 2 ) INFORMATION FOR SEQ ID NO:14:

( i ) SEQUENCE CHARACTERISTICS:
( A ) LENGTH: 13 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:14:

Cys Xaa Xaa His Xaa Xaa Xaa Xaa Xaa Cys Xaa Xaa Cys
1               5                           10

( 2 ) INFORMATION FOR SEQ ID NO:15:

( i ) SEQUENCE CHARACTERISTICS:
( A ) LENGTH: 12 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:15:

Glu Ala Ala Ala Arg Ala Ala Glu Ala Ala Arg
1               5                   10

( 2 ) INFORMATION FOR SEQ ID NO:16:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:16:

Thr Asp Thr Leu Gln Ala Glu Thr Asp Gln Leu Glu Asp Lys Lys Ser
1               5                   10                  15

Ala Leu Gln Thr Glu Ile Ala Asn Leu Leu Lys Glu Lys Glu Lys Leu
            20                  25                  30

( 2 ) INFORMATION FOR SEQ ID NO:17:

( i ) SEQUENCE CHARACTERISTICS:
    ( A ) LENGTH: 32 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:17:

Ile Ala Arg Leu Glu Glu Lys Val Lys Thr Leu Lys Ala Gln Asn Ser
1               5                   10                  15

Glu Leu Ala Ser Thr Ala Asn Met Leu Arg Glu Gln Val Ala Gln Leu
            20                  25                  30

( 2 ) INFORMATION FOR SEQ ID NO:18:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:18:

Asp Asp Asp Lys
1

( 2 ) INFORMATION FOR SEQ ID NO:19:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:19:

Ile Glu Gly Arg
1

( 2 ) INFORMATION FOR SEQ ID NO:20:

( i ) SEQUENCE CHARACTERISTICS:

(A) LENGTH: 7 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:20:

Leu Val Pro Arg Gly Ser Pro
1               5

(2) INFORMATION FOR SEQ ID NO:21:

(i) SEQUENCE CHARACTERISTICS:
(A) LENGTH: 17 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:21:

AGCGTAACGA TCTCCCG                                                                17

(2) INFORMATION FOR SEQ ID NO:22:

(i) SEQUENCE CHARACTERISTICS:
(A) LENGTH: 38 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:22:

Ser Ser Cys Ala Tyr Ala Arg Tyr Val Pro Leu Leu Leu Leu Leu Tyr
1               5                   10                  15

Ala Asn Pro Gly Met Tyr Ser Arg Leu His Ser Pro Ala Val Arg Pro
                20                  25                  30

Leu Thr Gln Ser Ser Ala
            35

(2) INFORMATION FOR SEQ ID NO:23:

(i) SEQUENCE CHARACTERISTICS:
(A) LENGTH: 38 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:23:

Ser Val Gln Phe Lys Ser Ile Ser Ser Arg Ser Met Asp Asp Val Val
1               5                   10                  15

Lys Asp Pro Gly Pro Lys Pro Ala Met Trp Lys Met Leu His Ser Lys
                20                  25                  30

Asn Pro Phe Thr Leu Ser
            35

(2) INFORMATION FOR SEQ ID NO:24:

(i) SEQUENCE CHARACTERISTICS:
(A) LENGTH: 38 amino acids
(B) TYPE: amino acid
(C) STRANDEDNESS: single
(D) TOPOLOGY: unknown (i) MOLECULE TYPE: peptide (xi) SEQUENCE DESCRIPTION: SEQ ID NO:24:

```
Phe Asp His Thr Tyr Ser Gly Pro Val Cys Val Lys Asn Gly Gly Leu
1               5                   10                  15
Val Ser Pro Gly Val Leu Ser Met Tyr Asn Arg Leu His Ser Asp Gly
            20                  25                  30
Gly Pro Ser Leu Ala Ser
            35
```

(2) INFORMATION FOR SEQ ID NO:25:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:25:

```
Thr Val Ala Thr Met His Asp Thr Leu His Ser Ala Pro Gly Ser Gly
1               5                   10                  15
Asn Leu Pro Gly Ser Tyr Asp Ile Lys Pro Ile Phe Lys Ala Ser Gly
            20                  25                  30
Ala Leu His Ser Thr Xaa
            35
```

(2) INFORMATION FOR SEQ ID NO:26:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:26:

```
Ile Asp Met Pro Glu Thr Ala Ser Thr Met Tyr Asn Met Leu His Arg
1               5                   10                  15
Asn Glu Pro Gly Gly Arg Lys Leu Ser Pro Pro Ala Asn Asp Met Pro
            20                  25                  30
Pro Ala Leu Leu Lys Arg
            35
```

(2) INFORMATION FOR SEQ ID NO:27:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:27:

```
Arg Leu Gly Asn Val Trp Arg Val Glu Gly Gly Gly Met Tyr Gln Gln
1               5                   10                  15
Leu His His Asn Phe Pro Xaa
            20
```

(2) INFORMATION FOR SEQ ID NO:28:

(i) SEQUENCE CHARACTERISTICS:

(A) LENGTH: 23 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:28:

Arg Asp Ser Ala Val Glu Asn Pro Ser Val Gly Gly Glu Ile Pro Met
1               5                   10                  15

Tyr Arg Tyr Leu His Gln Arg
            20

(2) INFORMATION FOR SEQ ID NO:29:

(i) SEQUENCE CHARACTERISTICS:
(A) LENGTH: 23 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:29:

Pro Val Gln Lys Glu Tyr Gly Phe Phe Met Ser Gly Ala Ser Met Ile
1               5                   10                  15

Arg Leu Leu Arg Glu Thr Pro
            20

(2) INFORMATION FOR SEQ ID NO:30:

(i) SEQUENCE CHARACTERISTICS:
(A) LENGTH: 23 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:30:

Gln Lys Gly Gly Pro Gly Leu Leu Leu Tyr Gly Gly Asp Ser Met Trp
1               5                   10                  15

Ile Thr Leu His Glu Pro Gly
            20

(2) INFORMATION FOR SEQ ID NO:31:

(i) SEQUENCE CHARACTERISTICS:
(A) LENGTH: 15 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:31:

Leu Tyr Ala Asn Pro Gly Met Tyr Ser Arg Leu His Ser Pro Ala
1               5                   10                  15

(2) INFORMATION FOR SEQ ID NO:32:

(i) SEQUENCE CHARACTERISTICS:
(A) LENGTH: 18 amino acids
(B) TYPE: amino acid
(C) STRANDEDNESS: single
(D) TOPOLOGY: unknown (ii) MOLECULE TYPE: peptide ( x i ) SEQUENCE DESCRIPTION: SEQ ID NO:32:

Pro Ser Tyr Tyr Arg Gly Asp Ala Gly Pro Ser Tyr Tyr Arg Gly Asp
1               5                   10                  15
Ala Gly ( 2 ) INFORMATION FOR SEQ ID NO:33:

( i ) SEQUENCE CHARACTERISTICS:
     ( A ) LENGTH: 17 amino acids
     ( B ) TYPE: amino acid
     ( C ) STRANDEDNESS: single
     ( D ) TOPOLOGY: unknown ( i i ) MOLECULE TYPE: peptide ( x i ) SEQUENCE DESCRIPTION: SEQ ID NO:33:

Ser Tyr Gly Arg Gly Asp Val Arg Gly Asp Phe Lys Cys Thr Cys Cys
1               5                   10                  15
Ala ( 2 ) INFORMATION FOR SEQ ID NO:34:

( i ) SEQUENCE CHARACTERISTICS:
     ( A ) LENGTH: 38 amino acids
     ( B ) TYPE: amino acid
     ( C ) STRANDEDNESS: single
     ( D ) TOPOLOGY: unknown ( i i ) MOLECULE TYPE: peptide ( x i ) SEQUENCE DESCRIPTION: SEQ ID NO:34:

Thr Gly Leu His Thr Phe Ala His Gly Val Ser Tyr Gly Tyr Phe Gly
1               5                   10                  15
Ile Gly Pro Gly His His Ser Ser Glu Gly Asp His Ile Pro Ile His
                20                  25                  30
Thr Asp Val Ser His His
                35

( 2 ) INFORMATION FOR SEQ ID NO:35:

( i ) SEQUENCE CHARACTERISTICS:
     ( A ) LENGTH: 38 amino acids
     ( B ) TYPE: amino acid
     ( C ) STRANDEDNESS: single
     ( D ) TOPOLOGY: unknown ( i i ) MOLECULE TYPE: peptide ( x i ) SEQUENCE DESCRIPTION: SEQ ID NO:35:

Gly Val Val Ser Ser Glu Trp Ala Ser Lys His Tyr Asn His His Phe
1               5                   10                  15
His Thr Pro Gly Phe Leu Val Arg His Phe Cys Thr Pro Ile Ser Gln
                20                  25                  30
Met Asp His Lys Glu Thr
                35

( 2 ) INFORMATION FOR SEQ ID NO:36:

( i ) SEQUENCE CHARACTERISTICS:
     ( A ) LENGTH: 38 amino acids
     ( B ) TYPE: amino acid
     ( C ) STRANDEDNESS: single
     ( D ) TOPOLOGY: unknown ( i i ) MOLECULE TYPE: peptide -continued ( x i ) SEQUENCE DESCRIPTION: SEQ ID NO:36:

Gly Ala Tyr Gly His Arg Tyr Met Gly His Pro Ile Leu Ile Asn Val
1               5                   10                  15

Gln Asp Pro Gly Phe Gln Ile Leu Ser Thr His Trp Glu Phe Asn Asn
                20                  25                  30

Arg Ala Ser His His Pro
            35

( 2 ) INFORMATION FOR SEQ ID NO:37:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:37:

Glu Lys Phe Asp Ala Ala His Gly Thr Asp Met Tyr Phe Ser Ser Gln
1               5                   10                  15

His Tyr Pro Gly His Asn Asn Ile Pro His His Pro Arg Ala Glu Phe
                20                  25                  30

Phe His Gly His Thr Leu
            35

( 2 ) INFORMATION FOR SEQ ID NO:38:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:38:

Thr Thr His Gln His His Val Thr Phe Ser Thr Ser Ala His Asn Pro
1               5                   10                  15

Phe Ser Pro Gly His Asn Tyr Gly Val Arg Thr Gln Leu Pro Ala Thr
                20                  25                  30

Ser His Thr His Ile Pro
            35

( 2 ) INFORMATION FOR SEQ ID NO:39:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:39:

His Glu Thr Trp Asp Tyr Tyr His His Asn Ser Phe Leu Pro His Asp
1               5                   10                  15

Tyr Ser Pro Gly Ile Leu Ser Ser His Asn Val Phe Arg Lys Glu Arg
                20                  25                  30

Arg Glu Tyr Glu Asn Ser
            35

( 2 ) INFORMATION FOR SEQ ID NO:40:

( i ) SEQUENCE CHARACTERISTICS:
  ( A ) LENGTH: 38 amino acids
  ( B ) TYPE: amino acid
  ( C ) STRANDEDNESS: single
  ( D ) TOPOLOGY: unknown ( i i ) MOLECULE TYPE: peptide ( x i ) SEQUENCE DESCRIPTION: SEQ ID NO:40:

Tyr Asn Leu Ile Ala Pro Ser Phe His Gly Gly Asn Asp Arg Ala Gln
1               5                   10                  15

Ser Val Pro Gly Val His His His His Pro Glu Ser Lys Ala Tyr Pro
            20                  25                  30

Gln Leu Ser Tyr Gly Lys
            35

( 2 ) INFORMATION FOR SEQ ID NO:41:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:41:

Ala His Glu Pro Asn Ser Phe Gly Phe Val Gln Gly Ala His Asp His
1               5                   10                  15

Asn Pro Pro Gly Thr Thr Ser Pro Ser Pro His Asp Trp Pro Asn Leu
            20                  25                  30

His His Trp Gly Ile Ile
            35

( 2 ) INFORMATION FOR SEQ ID NO:42:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:42:

Ser Ser His Gln His Phe Pro Tyr Leu Asn Ser Arg Asp Pro Ile Arg
1               5                   10                  15

Ser His Pro Gly His Pro Glu His Gln Tyr Pro Tyr Gly Ala Gly Ile
            20                  25                  30

Ser Ser Asn Ser Pro Ser
            35

( 2 ) INFORMATION FOR SEQ ID NO:43:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:43:

Met Gly Pro Ser Tyr Thr Asp Asn Gly Asp Gly Asn Arg His Asp His
1               5                   10                  15

Tyr Val Pro Gly His Pro Ile Pro Pro Asn Glu Leu His Arg His Thr 20                          25                          30

Thr Ile Pro Glu Ser Leu
                    35

(2) INFORMATION FOR SEQ ID NO:44:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:44:

Gly Pro Pro Gly Asp Gly Ala His Ala Asp Asp His Lys His Arg Trp
        1               5                   10                  15

Thr His Pro Gly Tyr His Ser Gly Tyr Met His Ser Pro Leu Thr Leu
                        20                  25                  30

His Thr Gln His Ser Gln
                        35

(2) INFORMATION FOR SEQ ID NO:45:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:45:

Ser Ser His Asp Ser Ile Tyr Asn Phe Glu Phe Arg Glu Val Asn His
        1               5                   10                  15

His Ser Pro Gly Asn Gly Leu Gly Gly Val Ser His Thr His His Ser
                        20                  25                  30

Asn Met Ser Arg Leu Asp
                        35

(2) INFORMATION FOR SEQ ID NO:46:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:46:

Gln Pro Thr Ile Ser Pro Pro Asp Phe Asn His Arg Ala Ser Leu Asn
        1               5                   10                  15

His Leu Pro Gly His Asn Met Ser His Ser Asn Ser Ser Gly Ser Leu
                        20                  25                  30

Thr Leu Pro Ala Val His
                        35

(2) INFORMATION FOR SEQ ID NO:47:

(i) SEQUENCE CHARACTERISTICS:
        (A) LENGTH: 38 amino acids
        (B) TYPE: amino acid
        (C) STRANDEDNESS: single
        (D) TOPOLOGY: unknown (i i) MOLECULE TYPE: peptide (x i) SEQUENCE DESCRIPTION: SEQ ID NO:47:

Asp Ala Asn Gly Thr Ser Leu Ser Asp Glu Arg Met Tyr His His Asn
1               5                   10                  15

Val Ser Pro Gly Phe Arg His Phe Gln Gly Trp Thr His Asp His Asp
                20              25                  30

His Ala Tyr Pro His Met
            35

(2) INFORMATION FOR SEQ ID NO:48:

(i) SEQUENCE CHARACTERISTICS:
    (A) LENGTH: 38 amino acids
    (B) TYPE: amino acid
    (C) STRANDEDNESS: single
    (D) TOPOLOGY: unknown (i i) MOLECULE TYPE: peptide (x i) SEQUENCE DESCRIPTION: SEQ ID NO:48:

Gly Tyr Pro Arg Val Thr Thr Arg Phe Ser Asp Ser Ile Gly Tyr His
1               5                   10                  15

Tyr Ala Pro Gly Pro Arg Ala Glu His Ser Val His His Gly Thr His
                20              25                  30

Asp Ser His Pro Asn Thr
            35

(2) INFORMATION FOR SEQ ID NO:49:

(i) SEQUENCE CHARACTERISTICS:
    (A) LENGTH: 38 amino acids
    (B) TYPE: amino acid
    (C) STRANDEDNESS: single
    (D) TOPOLOGY: unknown (i i) MOLECULE TYPE: peptide (x i) SEQUENCE DESCRIPTION: SEQ ID NO:49:

Tyr Asp His His Ser Tyr Asn Gly Asp Met His Tyr Pro Gly Trp Pro
1               5                   10                  15

Pro Leu Pro Gly Pro His His Phe Ala Pro Ile Asp Val Thr Thr His
                20              25                  30

Ser His Thr Gln Pro Asp
            35

(2) INFORMATION FOR SEQ ID NO:50:

(i) SEQUENCE CHARACTERISTICS:
    (A) LENGTH: 38 amino acids
    (B) TYPE: amino acid
    (C) STRANDEDNESS: single
    (D) TOPOLOGY: unknown (i i) MOLECULE TYPE: peptide (x i) SEQUENCE DESCRIPTION: SEQ ID NO:50:

Ile Asp His His His His Thr Phe Thr Thr Arg Asn Ala Pro Ser Gln
1               5                   10                  15

Pro Asn Pro Gly Pro Pro Tyr Phe Pro His Val His His Arg Asp Ser
                20              25                  30

Ser Ser Met Ser Lys Arg
            35

( 2 ) INFORMATION FOR SEQ ID NO:51:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:51:

```
His Ser Tyr His Asp Val Ala Thr Thr Lys Pro Gly Ser His Cys Met
 1               5                  10                 15
His Asn Pro Gly His Pro Pro Pro Asn Cys His Met Ala Lys Ala
            20              25              30
His Ser His Asn Arg Ile
        35
```

( 2 ) INFORMATION FOR SEQ ID NO:52:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:52:

```
Ala Thr Glu Gln His Tyr Trp Thr Gln Tyr His Lys Pro Tyr His Pro
 1               5                  10                 15
Ser Val Pro Gly Phe His Val Lys Ser Val Thr Glu Thr Thr Asp His
            20              25              30
Trp Glu Ser Arg Asn Gly
        35
```

( 2 ) INFORMATION FOR SEQ ID NO:53:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:53:

```
Ser Val Lys Ala His His Met Glu Arg Pro Leu Asn Asn Phe Asp Gly
 1               5                  10                 15
Pro Pro Pro Gly Asp Arg Val Val Gly Cys His Leu Phe Arg Val Thr
            20              25              30
Ser Gly Gln Cys Arg His
        35
```

( 2 ) INFORMATION FOR SEQ ID NO:54:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:54:

```
Phe Ala Tyr Gly Ser Thr Asn Val Val Met Val Glu His Asn Ser Asp
 1               5                  10                 15
```

```
          His  Asn  Pro  Gly  His  Thr  Val  Ser  Cys  Ser  Ala  Thr  Gln  Gly  His  Ile
                         20                       25                      30

Cys  Asp  Asp  Asn  Thr  Arg
                         35
```

(2) INFORMATION FOR SEQ ID NO:55:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:55:

```
          Glu  Leu  Val  Ile  Asn  Leu  Ala  Ser  Ile  Val  Ala  Gly  Ser  Arg  Asn
          1                   5                        10                      15

Ile  Gly  Pro  Gly  Arg  Leu  Ser  Gly  Leu  His  Tyr  Gly  Pro  Pro  Glu  Gln
                         20                       25                      30

Tyr  Phe  Arg  His  Ser  Pro
                         35
```

(2) INFORMATION FOR SEQ ID NO:56:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:56:

```
          Tyr  Leu  Ala  Thr  Ser  Arg  Phe  Pro  Leu  Thr  Gln  Ser  Val  Ala  Leu  Thr
          1                   5                        10                      15

His  Ser  Pro  Gly  Ser  Ser  Ser  His  Pro  Leu  Thr  Ser  Tyr  Arg  Trp  Asp
                         20                       25                      30

Ala  His  Ser  Asn  His  Pro
                         35
```

(2) INFORMATION FOR SEQ ID NO:57:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:57:

```
          Asp  Tyr  Ser  Val  Leu  Val  Thr  Ser  Leu  Arg  Ile  Thr  Gly  Ser  Leu  Tyr
          1                   5                        10                      15

Cys  Pro  Pro  Gly  Pro  Arg  Tyr  Asn  Phe  His  Asp  Asn  His  Gly  Arg  Pro
                         20                       25                      30

Cys  Gly  Ser  Arg  Ser  Cys
                         35
```

(2) INFORMATION FOR SEQ ID NO:58:

(i) SEQUENCE CHARACTERISTICS:
        (A) LENGTH: 38 amino acids
        (B) TYPE: amino acid
        (C) STRANDEDNESS: single (D) TOPOLOGY: unknown (i i) MOLECULE TYPE: peptide (x i) SEQUENCE DESCRIPTION: SEQ ID NO:58:

Tyr Phe Ala Val Met Cys Asp Glu Gly Arg Asn Thr Arg Val Cys His
1               5                   10                  15

His Ser Pro Gly Trp Leu Thr His Gly Arg Tyr Ser Val Ser Ala Thr
            20                  25                  30

Asp Asp Leu Ser Gly Ser
            35

(2) INFORMATION FOR SEQ ID NO:59:

(i) SEQUENCE CHARACTERISTICS:
    (A) LENGTH: 38 amino acids
    (B) TYPE: amino acid
    (C) STRANDEDNESS: single
    (D) TOPOLOGY: unknown (i i) MOLECULE TYPE: peptide (x i) SEQUENCE DESCRIPTION: SEQ ID NO:59:

Cys His Ile Thr Cys Lys Asp Cys Thr Gly Glu His His Ser Val Tyr
1               5                   10                  15

Cys Thr Pro Gly Ile Asp Ser Ser Asn Thr Glu Pro Gln Ala Ser Met
            20                  25                  30

His Tyr Phe Asn Pro His
            35

(2) INFORMATION FOR SEQ ID NO:60:

(i) SEQUENCE CHARACTERISTICS:
    (A) LENGTH: 38 amino acids
    (B) TYPE: amino acid
    (C) STRANDEDNESS: single
    (D) TOPOLOGY: unknown (i i) MOLECULE TYPE: peptide (x i) SEQUENCE DESCRIPTION: SEQ ID NO:60:

Tyr Asn Gly Lys Asp His Gln Leu Pro Met Leu Thr Pro Ser His Ala
1               5                   10                  15

Thr Gly Pro Gly Ser Cys Trp Phe Asn Gln Thr Thr Val Pro Thr Ser
            20                  25                  30

Asp Ile Glu Gly His His
            35

(2) INFORMATION FOR SEQ ID NO:61:

(i) SEQUENCE CHARACTERISTICS:
    (A) LENGTH: 38 amino acids
    (B) TYPE: amino acid
    (C) STRANDEDNESS: single
    (D) TOPOLOGY: unknown (i i) MOLECULE TYPE: peptide (x i) SEQUENCE DESCRIPTION: SEQ ID NO:61:

His Glu Ser Asp Arg His Asp Ala Ile Ser Ser Val Gly Arg Ser Leu
1               5                   10                  15

Asp Val Pro Gly Thr His Arg Asp Trp Ala Ser His Tyr Ile His Phe
            20                  25                  30

Ile Thr Gly His Asn Phe
            35

(2) INFORMATION FOR SEQ ID NO:62:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:62:

```
Glu Ser Ile Arg Tyr Tyr Thr Ser Arg Gln Asp Ser Tyr Arg Ser Asn
1               5                   10                  15
Leu Ala Pro Gly Thr Tyr Asn Ile Val Asp Tyr Asn Thr Ser Leu His
            20                  25                  30
Thr Leu Thr His Thr Thr
            35
```

(2) INFORMATION FOR SEQ ID NO:63:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:63:

```
Ser Pro Ile Cys His His Ser Gly Gln Phe Val Tyr Asp His Pro Asn
1               5                   10                  15
His Ser Pro Gly Pro Met Lys Ser Leu Phe Gln His His Cys Arg Asn
            20                  25                  30
Asn Glu Leu Pro Leu Asn
            35
```

(2) INFORMATION FOR SEQ ID NO:64:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:64:

```
Asp Val Asp Met Gly Thr Ile Phe Asn Thr Ile Ala Asn Asn Ile Thr
1               5                   10                  15
Ser Arg Pro Gly Val Ser Trp Gly Gly Ser Thr Arg Thr Ile Thr Lys
            20                  25                  30
Pro Lys Gly Ala Val Ala
            35
```

(2) INFORMATION FOR SEQ ID NO:65:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:65:

-continued

```
Gln Thr Ala Gly Gln Pro Gly Arg Thr Leu Ser Lys Pro Pro Ile Pro
1               5                   10                  15

Asn Thr Pro Gly Pro Arg Glu Pro Ser Leu Leu His Ser Met Pro His
            20              25                  30

Leu Pro Asn Leu Thr Ala
            35
```

( 2 ) INFORMATION FOR SEQ ID NO:66:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:66:

```
Val Arg Thr Ile Ser Lys Pro Val Ala Arg Glu Gly Trp Thr Arg Asp
1               5                   10                  15

Thr Val Pro Gly Pro Ala Thr Ser Ile Val Glu Lys Arg Phe His Leu
            20              25                  30

Ile Gly Val Asn Ala Gln
            35
```

( 2 ) INFORMATION FOR SEQ ID NO:67:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:67:

```
Lys Gly Ala Ser Phe Tyr Pro Gln Cys Gly Glu Cys Gln Ile Tyr
1               5                   10                  15

Arg Val Pro Gly Asp His Leu Pro Leu Phe Ser Leu His Arg Thr Gly
            20              25                  30

Thr Pro Arg His Asp Ser
            35
```

( 2 ) INFORMATION FOR SEQ ID NO:68:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:68:

```
Asn Ala Val Arg Val Asp Ser Gly Tyr Pro Pro Asn Pro Asn Thr Phe
1               5                   10                  15

His Leu Pro Gly Cys Ile Asp Val Leu Ser Ser Gly Cys Arg Leu Phe
            20              25                  30

Ser Ala His Ser Glu Tyr
            35
```

( 2 ) INFORMATION FOR SEQ ID NO:69:

( i ) SEQUENCE CHARACTERISTICS:
        ( A ) LENGTH: 38 amino acids ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:69:

Cys Asn Phe Arg Gly Gln Cys Val Ser Ala Pro Gln Thr Ser Asn Ser
1               5                   10                  15

Lys Ser Pro Gly Trp Asp Thr Thr Trp His Asp Phe Arg Lys Glu Gln
                20                  25                  30

Phe Tyr Asn Leu Thr Ser
            35

( 2 ) INFORMATION FOR SEQ ID NO:70:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:70:

His Pro Ala Cys Met Gly Phe Ser His Pro Tyr Gly Pro Thr Asn Cys
1               5                   10                  15

Leu Ser Pro Gly Glu Val Asn Lys Asn Val Pro Ser Leu Pro Ile Thr
                20                  25                  30

Pro Asp Arg Glu Ser Pro
            35

( 2 ) INFORMATION FOR SEQ ID NO:71:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:71:

Ser Gln Val Pro Thr Ile Asp Ala Phe Ser Val Gly Met Gly Lys Asp
1               5                   10                  15

Asp His Pro Gly Met Ile Ser Glu Pro Ser Phe Asn Leu Arg Val Pro
                20                  25                  30

His Ile Asp Lys Phe Ala
            35

( 2 ) INFORMATION FOR SEQ ID NO:72:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:72:

Pro Gly Glu Gln Ser Asn Leu Asn Thr Arg Val Lys Glu Gly Asn Trp
1               5                   10                  15

Ser Ser Ser

-continued ( 2 ) INFORMATION FOR SEQ ID NO:73:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:73:

Ala Tyr Gly Thr Val Cys Cys Ser Gly Met Phe Thr Tyr Ser Asn Ser
1               5                   10                  15

Pro Arg Pro Gly Val Asn Glu Asn Arg Val Pro Val Gly Asp Lys
            20                  25                  30

Gly Asn Asn Pro Asp Leu
            35

( 2 ) INFORMATION FOR SEQ ID NO:74:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:74:

Thr Ser Pro Ala Cys Ala Ser Gly Ser Thr His Gly Ala Leu Thr Asp
1               5                   10                  15

Cys Trp Pro Gly Phe Ser Tyr Asn Thr Arg Val Pro Tyr Ile Ser Gln
            20                  25                  30

Val Glu Thr Asn Ala Xaa
            35

( 2 ) INFORMATION FOR SEQ ID NO:75:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:75:

Tyr Gly Phe Ser Asn Thr Met Met Ala His Gly Thr His Val Tyr Phe
1               5                   10                  15

Ser Pro Pro Gly Phe Thr Leu Val Val Pro Ile Ser Tyr Asn Ser Arg
            20                  25                  30

Val Pro Arg Ala Asp Ala
            35

( 2 ) INFORMATION FOR SEQ ID NO:76:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:76:

Arg Tyr Asn Glu Pro Val Tyr Leu Tyr Gln Pro Ser Val Asp Gln Lys
1               5                   10                  15

```
            Gly  Ile  Pro  Gly  Pro  Tyr  Leu  Thr  Leu  Val  His  Tyr  Asn  Asn  Arg  Val
                            20                      25                       30

Pro  Leu  Thr  Ala  Ser  Ile
                       35
```

( 2 ) INFORMATION FOR SEQ ID NO:77:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:77:

```
            Gly  Asp  Gly  Val  Pro  Leu  Phe  Asn  Asn  Ser  Thr  His  Lys  Ile  Thr  Met
            1                    5                      10                       15

Leu  Asn  Pro  Gly  His  Asp  Thr  Arg  Met  Lys  Thr  Asp  Phe  Val  Asn  Lys
                            20                      25                       30

Lys  Ser  Val  Tyr  Ser  Pro
                       35
```

( 2 ) INFORMATION FOR SEQ ID NO:78:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:78:

```
            Thr  Phe  Lys  Pro  Asp  Leu  Lys  Ser  Asn  Phe  Ala  Gly  Ser  Ser  Ala  Ser
            1                    5                      10                       15

Pro  Asn  Pro  Gly  Ala  Trp  Asn  Gly  Leu  Arg  Pro  Arg  Pro  Val  Asp  Gly
                            20                      25                       30

Val  Pro  Ser  Ala  Val  Asp
                       35
```

( 2 ) INFORMATION FOR SEQ ID NO:79:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:79:

```
            Ser  Asn  Glu  His  Phe  Arg  Asp  Arg  Val  Ser  Ile  Ser  Lys  Ile  His  Ile
            1                    5                      10                       15

Ser  Ser  Pro  Gly  Tyr  Ala  Asn  Trp  Leu  Asn  Pro  His  Leu  Ala  His  Lys
                            20                      25                       30

Met  Lys  Gly  Gln  Ala  Asn
                       35
```

( 2 ) INFORMATION FOR SEQ ID NO:80:

( i ) SEQUENCE CHARACTERISTICS:
        ( A ) LENGTH: 38 amino acids
        ( B ) TYPE: amino acid
        ( C ) STRANDEDNESS: single (D) TOPOLOGY: unknown (ii) MOLECULE TYPE: peptide (xi) SEQUENCE DESCRIPTION: SEQ ID NO:80:

```
Tyr Leu Pro Trp Ser Lys Ser Phe Ser Pro Ser Gln Tyr Thr Ser Met
1               5                   10                  15

Ile Asn Pro Gly His Asn Ser Phe Ser Ser Gln Asp Thr Leu Tyr Phe
            20                  25                  30

Glu Arg Val Ala Pro His
            35
```

(2) INFORMATION FOR SEQ ID NO:81:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:81:

```
Ala Phe Gly Arg Glu Ile Cys Ile Asp Phe Met His Pro Cys Ser Arg
1               5                   10                  15

Thr Arg Pro Gly His Asp Phe Ser Glu Lys Pro Asn Gly Ser Lys Asp
            20                  25                  30

Pro Gln Ile Ser Phe Ser
            35
```

(2) INFORMATION FOR SEQ ID NO:82:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:82:

```
Ser Asp Gly Met His Cys Pro His Ala Phe Cys Asn Glu His Tyr His
1               5                   10                  15

Ala Pro Pro Gly Pro His Met Leu Ser Asp Leu Phe Pro Gly Arg Glu
            20                  25                  30

Lys Pro Pro Tyr Thr Pro
            35
```

(2) INFORMATION FOR SEQ ID NO:83:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:83:

```
Val Arg Asp Ala Asp His Thr Val Phe Asp Ala Thr Tyr Cys Ser Ser
1               5                   10                  15

Ser Ala Pro Gly Ser Pro Ser His Ser Asn Gln Met Leu Leu Asn Pro
            20                  25                  30

His Ile Leu Arg Pro Cys
            35
```

( 2 ) INFORMATION FOR SEQ ID NO:84:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:84:

```
Gly Pro Val Asp Val His Val Ala Leu Ser Val Ser His Asn Ser Ser
1               5                   10                  15
Lys His Pro Gly Thr Ala Pro Phe Thr Glu Met His Ser Pro Leu Phe
                20                  25                  30
Asp Asn Pro His His Thr
            35
```

( 2 ) INFORMATION FOR SEQ ID NO:85:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:85:

```
Ala Asp Ser His Met Gly Xaa Trp Gln Tyr Tyr Arg Trp Trp Met Arg
1               5                   10                  15
Val Gly Pro Gly Arg Trp Gly Ser Thr Pro Val Leu Phe Arg Pro Glu
                20                  25                  30
Phe Asp Arg Glu Trp Phe
            35
```

( 2 ) INFORMATION FOR SEQ ID NO:86:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:86:

```
Asp Pro Leu Leu Arg Asp Glu Ile Asn Asn Lys Pro Gly Gly Asp Phe
1               5                   10                  15
Tyr Leu Pro Gly Phe Leu Trp Pro Trp Asn Tyr Asn Phe His Ser Val
                20                  25                  30
His Thr Gln Arg Pro Ser
            35
```

( 2 ) INFORMATION FOR SEQ ID NO:87:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:87:

```
    Thr  Met  Arg  Thr  Asp  Trp  Gly  Phe  Arg  Asp  Leu  Asn  Pro  Tyr  Ile  Leu
    1              5                        10                       15

Ser  Pro  Pro  Gly  Leu  Ser  Arg  Thr  Asp  Phe  Gly  Pro  Thr  Glu  Phe  Arg
                   20                       25                  30

Gln  Asn  Asp  Ala  Lys  Lys
                   35
```

(2) INFORMATION FOR SEQ ID NO:88:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:88:

```
    Gly  Arg  Thr  Trp  His  Asn  Ile  Ser  Thr  Phe  His  Pro  Ala  His  Asn  Ser
    1              5                        10                       15

Glu  Gly  Pro  Gly  Tyr  Ile  Ala  Phe  Leu  Asn  Pro  Phe  Ser  Glu  Thr  Tyr
                   20                       25                  30

Val  Ser  Ser  Gly  Ser  Ser
                   35
```

(2) INFORMATION FOR SEQ ID NO:89:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:89:

```
    Pro  Ala  Glu  Gly  Gly  Asp  Glu  Ala  Gly  Arg  Gly  Gly  Ala  Thr  Cys  Arg
    1              5                        10                       15

Gln  Lys  Leu  Arg  Ile  Ala  Cys
                   20
```

(2) INFORMATION FOR SEQ ID NO:90:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:90:

```
    Gly  Asn  Asp  Arg  His  Ile  Gly  Glu  Asn  Arg  Cys  Gly  Val  Trp  Trp  Arg
    1              5                        10                       15

Glu  Pro  Glu  Cys  Gly  Ala  Thr
                   20
```

(2) INFORMATION FOR SEQ ID NO:91:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:91:

```
Gly Lys Leu Gly Ser Trp Arg His Ala Xaa Xaa Val Cys Pro Thr Ile
1               5                   10                  15
Pro
```

(2) INFORMATION FOR SEQ ID NO:92:

(i) SEQUENCE CHARACTERISTICS:
        (A) LENGTH: 17 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:92:

```
Asp Ser Cys Ser Ile Ala Trp Phe Xaa Ala Cys Gly Glu Ile Pro Val
1               5                   10                  15
Pro
```

(2) INFORMATION FOR SEQ ID NO:93:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:93:

```
Asp Val Pro Asp Val Met Gly Ala Arg Cys Gly Gly Ala Xaa Arg Gly
1               5                   10                  15
Trp Pro Glu Leu Leu Arg Pro
                20
```

(2) INFORMATION FOR SEQ ID NO:94:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:94:

```
Val Arg Leu Leu Asp Ile Leu Ser Pro Glu Gln Leu Ser Leu Asp Asp
1               5                   10                  15
Val Ser Pro Gly Leu Pro Glu Val Asn Arg Tyr Pro Ser Lys Leu Pro
                20                  25                  30
Pro Pro Asn Arg Leu Gly
                35
```

(2) INFORMATION FOR SEQ ID NO:95:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:95:

```
Glu Ala Leu Gly Asp Ser Gly Lys Lys Gly Gly Gly Val Pro Ser Gly
```

```
                1               5                       10                      15
```

Pro Glu Leu Phe Arg Tyr Pro
                20

(2) INFORMATION FOR SEQ ID NO:96:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:96:

Val Asp Pro Ser Thr Pro Asn Thr Leu Thr Asp Tyr Tyr Tyr Met Leu
1               5                       10                      15

Ser Gly Pro Gly Ala Thr Ser Phe Asp Gly Glu Arg Asn Arg Tyr Pro
                20                      25                      30

Ile Val Ser Thr Gln His
                35

(2) INFORMATION FOR SEQ ID NO:97:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:97:

Tyr Tyr Pro Val Tyr Gly Ser Met Arg Arg Leu Ala Asp Tyr Tyr Ser
1               5                       10                      15

Asn Gly Pro Gly Pro Glu Cys Val Arg His Gln Cys Thr Asp Glu His
                20                      25                      30

Arg Lys Ala Ile Asp Lys
                35

(2) INFORMATION FOR SEQ ID NO:98:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:98:

Glu Tyr Lys Ala Arg Ser Ser Phe Val Val Met Thr Gly Ala Glu Gly
1               5                       10                      15

Asn Ser Pro Gly Cys Asp Val Asp Arg His Cys Pro Tyr His His Ser
                20                      25                      30

Tyr Trp Thr Glu Ser Ile
                35

(2) INFORMATION FOR SEQ ID NO:99:

(i) SEQUENCE CHARACTERISTICS:
        (A) LENGTH: 23 amino acids
        (B) TYPE: amino acid
        (C) STRANDEDNESS: single
        (D) TOPOLOGY: unknown ( i i ) MOLECULE TYPE: peptide ( x i ) SEQUENCE DESCRIPTION: SEQ ID NO:99:

Asp Gln Ala Ser Tyr Phe Leu Asp Arg Trp Gly Gly Asp Gly Trp Ser
1               5                   10                  15

Phe Thr Pro Thr Pro Pro Met
            20

( 2 ) INFORMATION FOR SEQ ID NO:100:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:100:

Ser Leu Phe Phe Arg Pro Val Trp Glu Thr Ser Gly Glu Cys Phe Gln
1               5                   10                  15

Leu Phe Gln Pro Pro Pro Gly
            20

( 2 ) INFORMATION FOR SEQ ID NO:101:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:101:

Asn Gly Gly Arg Gly Cys Pro Val Glu Arg Cys Gly Asp Ser Val Thr
1               5                   10                  15

Gly Arg Ala Tyr Asp Ala Ile
            20

( 2 ) INFORMATION FOR SEQ ID NO:102:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:102:

Met Gly Gly Thr Tyr Trp Glu Asp Arg Trp Gly Gly Val Thr Leu Xaa
1               5                   10                  15

Pro Gln Xaa Arg Glu Thr Pro
            20

( 2 ) INFORMATION FOR SEQ ID NO:103:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:103:

```
His Gly Met Ala Ser Gln Tyr Phe Thr Cys Phe His Asp Ser Glu Pro
1               5                   10                  15

Ser Ser Pro Gly Met Phe Gly Trp Asp Pro Thr Thr Pro Thr Leu Pro
                20              25              30

His Pro Gln Val Asp Glu
                35
```

( 2 ) INFORMATION FOR SEQ ID NO:104:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:104:

```
Ile Ala His Arg Val Val Ala Tyr Asn Ser Leu Asp Ser Asn Pro Ile
1               5                   10                  15

Trp Leu Pro Gly Glu Glu Ser Ser Ser Val Phe Gly Asp Tyr His Pro
                20              25              30

Met Phe Arg Ala Pro Val
                35
```

( 2 ) INFORMATION FOR SEQ ID NO:105:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:105:

```
His Val Pro Val Phe Thr Arg Tyr Asn Tyr Ala Lys Pro Asn Asp Thr
1               5                   10                  15

Asp Trp Pro Gly Gly Phe Val Asp Ser Leu Ser Ala His Pro Gln Gly
                20              25              30

Pro Ile Ala Gly Gly Arg
                35
```

( 2 ) INFORMATION FOR SEQ ID NO:106:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:106:

```
Met Thr Leu Gly Tyr Asp Arg Ala Ser Pro Ala Pro Asn Thr Ser Phe
1               5                   10                  15

Ser Asn Pro Gly Leu Asp Phe Asn Pro Phe Thr Tyr His Pro Gln Gly
                20              25              30

Pro His Gln Ile Leu Gln
                35
```

( 2 ) INFORMATION FOR SEQ ID NO:107:

( i ) SEQUENCE CHARACTERISTICS:
        ( A ) LENGTH: 38 amino acids (B) TYPE: amino acid
(C) STRANDEDNESS: single
(D) TOPOLOGY: unknown (ii) MOLECULE TYPE: protein (xi) SEQUENCE DESCRIPTION: SEQ ID NO:107:

```
Ala  Gly  Arg  Ala  Ala  Arg  Asp  Asp  Asp  Cys  Arg  Gly  His  Ala  Cys  Met
1                   5                        10                      15
Ile  Ile  Pro  Gly  Val  Ser  Leu  Phe  Asn  Ser  Asp  His  Pro  Met  Gly  Ala
                20                        25                      30
His  Pro  Ser  Ile  Arg  Arg
                35
```

(2) INFORMATION FOR SEQ ID NO:108:

(i) SEQUENCE CHARACTERISTICS:
  (A) LENGTH: 38 amino acids
  (B) TYPE: amino acid
  (C) STRANDEDNESS: single
  (D) TOPOLOGY: unknown (ii) MOLECULE TYPE: protein (xi) SEQUENCE DESCRIPTION: SEQ ID NO:108:

```
Asp  Phe  Ser  Ser  Phe  Leu  Thr  Gly  Thr  Asn  Ala  Met  Ala  Pro  Phe  Trp
1                   5                        10                      15
Pro  Phe  Pro  Gly  Ser  Thr  Tyr  Leu  Leu  Gly  His  Pro  Met  Ala  Pro  Arg
                20                        25                      30
Asp  Leu  Gln  Thr  Ser  Asn
                35
```

(2) INFORMATION FOR SEQ ID NO:109:

(i) SEQUENCE CHARACTERISTICS:
  (A) LENGTH: 38 amino acids
  (B) TYPE: amino acid
  (C) STRANDEDNESS: single
  (D) TOPOLOGY: unknown (ii) MOLECULE TYPE: protein (xi) SEQUENCE DESCRIPTION: SEQ ID NO:109:

```
Ser  Ala  Ser  Trp  Lys  Phe  Asn  Ser  Ser  Phe  Gly  Tyr  Pro  Thr  Gly  Gly
1                   5                        10                      15
Ile  Glu  Pro  Gly  Pro  Asn  Cys  His  Pro  Gln  Ala  Cys  Pro  Asp  Val  Leu
                20                        25                      30
Ala  Lys  Ser  Leu  Ser  Pro
                35
```

(2) INFORMATION FOR SEQ ID NO:110:

(i) SEQUENCE CHARACTERISTICS:
  (A) LENGTH: 38 amino acids
  (B) TYPE: amino acid
  (C) STRANDEDNESS: single
  (D) TOPOLOGY: unknown (ii) MOLECULE TYPE: protein (xi) SEQUENCE DESCRIPTION: SEQ ID NO:110:

```
Val  Ser  Glu  Met  Ser  Ser  Phe  Ser  Gly  Cys  Asn  Thr  Asp  His  His  Pro
1                   5                        10                      15
Gln  Gly  Pro  Gly  Gly  Arg  His  Asp  Ile  Met  Arg  Ser  Ile  Ser  Glu  Ser
                20                        25                      30
```

Arg Gly Tyr Gly Ser Leu
35

( 2 ) INFORMATION FOR SEQ ID NO:111:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:111:

Glu Met Leu Thr Leu Pro Leu Thr Ser Ile Pro Ile Pro Trp His Pro
1               5                   10                  15

Gln Gly Pro Gly Tyr Leu Tyr His Lys Pro Pro Arg Gly Thr Asp Phe
            20                  25                  30

Arg Met Leu Ser Ser Lys
35

( 2 ) INFORMATION FOR SEQ ID NO:112:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:112:

Pro Tyr Arg Phe Tyr His Pro Tyr Ser His Pro Arg His Pro Gln Gly
1               5                   10                  15

Asp Val Pro Gly Ser Ser Ala Glu Val Phe His Thr Phe Pro Asn Thr
            20                  25                  30

Gln Gly Arg Asn Ser Arg
35

( 2 ) INFORMATION FOR SEQ ID NO:113:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:113:

Ala Asp Tyr Gly Thr Ile Gly Glu Ser Pro Cys His Pro Gln Val Asp
1               5                   10                  15

Ile Cys Pro Gly Ala Leu His His Glu Phe Asn Glu Phe Phe Val Gly
            20                  25                  30

Met Ser Pro Glu Pro Ser
35

( 2 ) INFORMATION FOR SEQ ID NO:114:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:114:

| Ala | Arg | Met | Ala | Gly | Leu | Thr | Glu | His | Pro | Gln | Gly | Asp | Ile | Ile | Asp |
| 1 | | | | 5 | | | | | 10 | | | | | 15 | |

| His | His | Pro | Gly | Trp | Val | His | Asp | Ser | Lys | Ile | Ser | Pro | Arg | Asn | Gln |
| | | | 20 | | | | | 25 | | | | | 30 | | |

| Asp | Thr | Tyr | His | Ser | Ser |
| | | | 35 | | |

( 2 ) INFORMATION FOR SEQ ID NO:115:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:115:

| Ala | His | Leu | Phe | Gly | His | Pro | Gln | Val | Gly | Phe | Asp | Ser | Ile | Gly | Ser |
| 1 | | | | 5 | | | | | 10 | | | | | 15 | |

| Ala | Phe | Pro | Gly | Asp | Ile | His | Cys | Lys | Gln | Tyr | Lys | Ala | Asp | Ser | Gly |
| | | | 20 | | | | | 25 | | | | | 30 | | |

| Leu | Gln | Ser | Ala | Ala | Ala |
| | | | 35 | | |

( 2 ) INFORMATION FOR SEQ ID NO:116:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:116:

| Pro | Asp | Tyr | Asp | Leu | Met | Ser | Ser | Thr | Cys | Arg | Phe | Tyr | Gly | Cys | Ser |
| 1 | | | | 5 | | | | | 10 | | | | | 15 | |

| Lys | Met | Pro | Gly | Gly | Val | Ala | Val | Asn | Gly | Leu | Phe | Ala | Val | Gln | Gly |
| | | | 20 | | | | | 25 | | | | | 30 | | |

| His | Ser | Lys | Tyr | Ser | Ser |
| | | | 35 | | |

( 2 ) INFORMATION FOR SEQ ID NO:117:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:117:

| Thr | Trp | Asp | Phe | Thr | Arg | Ser | Ser | Leu | Pro | Ala | Gly | Asp | Thr | Ser | Phe |
| 1 | | | | 5 | | | | | 10 | | | | | 15 | |

| Thr | Ser | Pro | Gly | Ser | Tyr | Ser | Val | Met | Thr | Arg | Ser | Cys | Gly | Ile | Ser |
| | | | 20 | | | | | 25 | | | | | 30 | | |

| Cys | Val | Pro | Ala | Glu | Val |
| | | | 35 | | |

( 2 ) INFORMATION FOR SEQ ID NO:118:

(  i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:118:

```
Ser Ser Arg Leu Ala Tyr Asp His Tyr Phe Pro Ser Trp Arg Ser Tyr
1               5                   10                  15
Ile Phe Pro Gly Ser Asn Ser Ser Tyr Tyr Asn Asn Ser Trp Pro Thr
            20                  25                  30
Ile Thr Met Glu Thr Asn
            35
```

( 2 ) INFORMATION FOR SEQ ID NO:119:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:119:

```
Pro Tyr Trp Met Phe Tyr Gly Phe Asp Trp Arg Gly Gly Phe Pro Pro
1               5                   10                  15
Ser His Gln Ile Met Asp Gln
            20
```

( 2 ) INFORMATION FOR SEQ ID NO:120:

( i ) SEQUENCE CHARACTERISTICS:
    ( A ) LENGTH: 38 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:120:

```
Asp Ser Trp Pro Leu Arg Ile Tyr Ser Gly Leu Ser Asn Tyr Tyr His
1               5                   10                  15
Tyr Phe Pro Gly Ser Leu Val Tyr Asn Met Met Tyr Pro Ser His Gly
            20                  25                  30
Glu Ala Pro Lys Gly Asp
            35
```

( 2 ) INFORMATION FOR SEQ ID NO:121:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:121:

```
Trp Gly Trp Ala Arg Gly Leu Gly Gly Gly Lys Gly Asp Ala Arg His
1               5                   10                  15
Pro Ser Ala Pro Glu Ala His
            20
```

( 2 ) INFORMATION FOR SEQ ID NO:122:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:122:

```
Trp Met Gln Ser Trp Tyr Tyr His Trp Gly Gly Gly Glu Thr Phe Pro
1               5                   10                  15
Ile Arg Arg Asp Ser Gly Gly
            20
```

( 2 ) INFORMATION FOR SEQ ID NO:123:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:123:

```
His His Gly Ala Met Asn Arg Tyr Tyr Thr Trp Leu Trp Asp Asn Ser
1               5                   10                  15
Arg Phe Pro Gly Arg Ser Tyr Leu Leu Ser Ala Pro Ala Thr Gln Pro
            20              25                  30
Glu Ala Ser Ile Ser Gln
            35
```

( 2 ) INFORMATION FOR SEQ ID NO:124:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:124:

```
Leu Gly Phe Ser Gly Trp Tyr Trp Gln Gly Leu Tyr Gly Leu Gly Ser
1               5                   10                  15
His Asp Pro Gly Phe Ile His Glu Gln Ser Pro Ala Glu Val Ala Met
            20              25                  30
Glu Asp Thr Glu Gln Ser
            35
```

( 2 ) INFORMATION FOR SEQ ID NO:125:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:125:

```
Arg Pro Tyr Leu Tyr Asp Pro Asn Glu Trp His Arg Tyr Tyr Ser Tyr
1               5                   10                  15
Leu Leu Pro Gly His Ser Tyr Asn Val Gln Ser Trp Pro Asp Gly Leu
            20              25                  30
```

Gly ( 2 ) INFORMATION FOR SEQ ID NO:126:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:126:

```
Pro Trp Trp Trp Val Ser Trp Val Asp Ala Gly Gly Gly Ser Leu Ala
1               5                   10                  15
Leu Pro Thr Gln Pro Ser Asp
            20
```

( 2 ) INFORMATION FOR SEQ ID NO:127:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:127:

```
Ile Tyr Tyr Pro Phe Phe Val Trp Gly Asn Tyr Ala Asn Gly Gly Leu
1               5                   10                  15
Leu Ser Pro Gly His Val Tyr Ser Ser Asn Phe Ile Pro Leu Tyr Met
            20                  25                  30
Gln Arg Glu Val Ser Pro
            35
```

( 2 ) INFORMATION FOR SEQ ID NO:128:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:128:

```
Gly Trp Gln Ser Gly Trp Glu Trp Trp Ile Gly Gly Gly Asn Trp Thr
1               5                   10                  15
Ser Asn Thr Thr His
            20
```

( 2 ) INFORMATION FOR SEQ ID NO:129:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:129:

```
Glu Ile His Gly Asn Leu Tyr Asn Trp Ser Pro Leu Leu Gly Tyr Ser
1               5                   10                  15
Tyr Phe Pro Gly Ile Ser Pro Lys His Ile Ser Gly Glu Val Leu Leu
```

-continued

```
                        20                        25                        30

Gly  Arg  Leu  Pro  Gln  Val
                      35
```

(2) INFORMATION FOR SEQ ID NO:130:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:130:

```
Tyr  Thr  Gly  Trp  Glu  Thr  Trp  Tyr  Ser  Phe  Asp  Pro  Phe  Thr  His  Tyr
 1                  5                       10                      15

Gly  Gly  Pro  Gly  Ser  Arg  Phe  Asp  Phe  Val  His  Asp  Lys  Ser  Glu  Asp
               20                       25                      30

Pro  Ile  Asp  Arg  Ser  Tyr
                35
```

(2) INFORMATION FOR SEQ ID NO:131:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:131:

```
Gln  Asp  Leu  Asp  His  Trp  Ser  Tyr  Trp  Ser  Met  Tyr  Ser  Thr  Tyr  Pro
 1                  5                       10                      15

Thr  Ser  Pro  Gly  Leu  Val  Pro  Tyr  Ser  Trp  Gly  Tyr  Gly  Ser  Pro  Asn
               20                       25                      30

Ser  His  Thr  Asp  Lys  Leu
                35
```

(2) INFORMATION FOR SEQ ID NO:132:

(i) SEQUENCE CHARACTERISTICS:
        (A) LENGTH: 23 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:132:

```
Trp  Trp  Asp  Pro  Asp  Ile  Trp  Phe  Gly  Trp  Gly  Gly  Ala  His  Pro  Pro
 1                  5                       10                      15

Asn  Leu  Ile  Gln  Pro  Ile  Ser
               20
```

(2) INFORMATION FOR SEQ ID NO:133:

(i) SEQUENCE CHARACTERISTICS:
        (A) LENGTH: 38 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:133:

Gln Thr Leu Ile Asp Phe His Asp Leu His Tyr Trp Gly Ala Tyr Tyr
1               5                   10                  15

Gly Trp Pro Gly Ile Tyr Asp Glu Ala Ser Gly Ser Gln Ala Val Arg
            20              25              30

His Asn Met Thr His Thr
            35

( 2 ) INFORMATION FOR SEQ ID NO:134:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:134:

Thr Tyr Asp Tyr Thr Tyr Asp Trp Ser Gly Leu Phe Trp Ser Pro Phe
1               5                   10                  15

Thr His Pro Gly Ala His Met Thr Thr His Ser Pro Trp Ala Gly His
            20              25              30

Lys Pro His Ala Glu Thr
            35

( 2 ) INFORMATION FOR SEQ ID NO:135:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:135:

Val Pro Arg Trp Ile Glu Asp Ser Leu Arg Gly Gly Ala Ala Arg Ala
1               5                   10                  15

Gln Thr Arg Leu Ala Ser Ala
            20

( 2 ) INFORMATION FOR SEQ ID NO:136:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:136:

CGTTACGAAT TCTTAAGACT CCTTATTACG CA    32

( 2 ) INFORMATION FOR SEQ ID NO:137:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:137:

CGTTAGGATC CCCATTCGTT TCTGAATATC AA    32

(2) INFORMATION FOR SEQ ID NO:138:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:138:

GCGACGCGAC GAGCTCGACT GCAAATTCTA TTTCAA 36

(2) INFORMATION FOR SEQ ID NO:139:

(i) SEQUENCE CHARACTERISTICS:
        (A) LENGTH: 54 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:139:

CTAATGTCTA GAAAGCTTCT CGAGCCCTGC AGCTGCACCT GGGCCATCGA CTGG 54

(2) INFORMATION FOR SEQ ID NO:140:

(i) SEQUENCE CHARACTERISTICS:
        (A) LENGTH: 5 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:140:

Gly Gly Gly Gly Ser
1                   5

(2) INFORMATION FOR SEQ ID NO:141:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:141:

CATGTATCGA TTAAATAAGG AGGAATAAC 29

TOTALLY SYNTHETIC AFFINITY REAGENTS

This is a divisional of application Ser. No. 08/176,500, filed Dec. 30, 1993 now U.S. Pat. No. 5,498,538, which is a continuation of application Ser. No. 08/013,416 filed Feb. 1, 1993, now abandoned, which is a continuation-in-part of application Ser. No. 07/854,133 filed Mar. 19, 1992 abandoned, which in turn is a continuation of application Ser. No. 07/480,420 filed Feb. 15, 1990 abandoned, the entire disclosures of which are incorporated herein by reference.

TABLE OF CONTENTS
1. FIELD OF THE INVENTION
2. BACKGROUND OF THE INVENTION
3. SUMMARY OF THE INVENTION
   3.1. OBJECTS AND ADVANTAGES OF THE INVENTION
4. BRIEF DESCRIPTION OF THE FIGURES
5. DETAILED DESCRIPTION OF THE INVENTION
   5.1. METHODS TO IDENTIFY TSARs: CONSTRUCTION OF LIBRARIES
      5.1.1. SYNTHESIS AND ASSEMBLY OF OLIGONUCLEOTIDES
      5.1.2. INSERTION OF SYNTHETIC OLIGONUCLEOTIDES INTO AN APPROPRIATE VECTOR
         5.1.2.1. LINEAR LIBRARIES
         5.1.2.2. BIOMOLECULAR LIBRARIES
      5.1.3. EXPRESSION OF VECTORS
   5.2. METHODS TO IDENTIFY TSARs: SCREENING LIBRARIES
   5.3. TSARs AND COMPOSITIONS COMPRISING A TSAR BINDING DOMAIN
   5.4. APPLICATIONS AND USES OF TSARs AND TSAR COMPOSITIONS
6. EXAMPLE: PREPARATION OF TSAR LIBRARIES
   6.1. PREPARATION OF THE TSAR-9 LIBRARY
      6.1.1. SYNTHESIS AND ASSEMBLY OF OLIGONUCLEOTIDES
      6.1.2. CONSTRUCTION OF VECTORS
      6.1.3. EXPRESSION OF THE TSAR-9 LIBRARY
   6.2. PREPARATION OF TSAR-12 LIBRARY
   6.3. CHARACTERIZATION OF THE TSAR-9 AND -12 LIBRARIES
      6.3.1. CHARACTERIZATION OF TSAR-9 LIBRARY
      6.3.2. CHARACTERIZATION OF TSAR-12 LIBRARY
7. IDENTIFICATION OF LIGAND BINDING TSARS
   7.1. METHODS FOR SCREENING
   7.2. IDENTIFICATION OF 7E11-C5 BINDING TSARS
   7.3. IDENTIFICATION OF METAL BINDING TSARS
   7.4. IDENTIFICATION OF TSARs BINDING A POLYCLONAL ANTIBODY
   7.5. IDENTIFICATION OF TSARs BINDING C46 ANTIBODY
   7.6. IDENTIFICATION OF TSARs BINDING ANTI-Sm ANTIBODY
   7.7. IDENTIFICATION OF TSARs BINDING STREPTAVIDIN
   7.8. IDENTIFICATION OF TSARs BINDING POLYSTYRENE
   7.9. IDENTIFICATION OF CALMODULIN BINDING TSARs
8. EXAMPLE: PHAGEMID VECTORS USEFUL FOR EXPRESSION OF TSAR LIBRARIES
   8.1. CONSTRUCTION OF VECTOR pDAF1
   8.2. CONSTRUCTION OF VECTORS pDAF2 AND pDAF3
9. EXAMPLE: PLASMID VECTOR USEFUL FOR EXPRESSION OF TSAR LIBRARIES
   9.1. THE INITIAL VECTOR pJG200
   9.2. REMOVAL OF THE $P_R$,$C_{I857}$ REPRESSOR AND AMINO TERMINUS OF CRO
   9.3. ADDITION OF THE $P_{TAC}$ PROMOTER, SHINE DALGARNO SEQUENCE AND ATG CODON
   9.4. IMPROVEMENT OF THE RIBOSOME BINDING SITE
10. DEPOSIT OF MICROORGANISMS

1. FIELD OF THE INVENTION

The present invention relates generally to methods for generating and screening large protein, polypeptide and/or peptide libraries for proteins, polypeptides, and/or peptides designated Totally Synthetic Affinity Reagents (TSARs) having binding specificity and desired affinity for ligands of choice. The invention further relates to novel TSARs identified according to the methods of the invention as well as compositions comprising the binding domains or a portion thereof having the same binding specificity.

2. BACKGROUND OF THE INVENTION

There have been two different approaches to the construction of random peptide libraries. According to one approach, peptides have been chemically synthesized in vitro in several formats. For example, Fodor, S., et al., 1991, Science 251: 767–773, describes use of complex instrumentation, photochemistry and computerized inventory control to synthesize a known array of short peptides on an individual microscopic slide. Houghten, R., et al., 1991, Nature 354: 84–86, describes mixtures of free hexapeptides in which the first and second residues in each peptide were individually and specifically defined. Lam, K., et al., 1991, Nature 354: 82–84, describes a "one bead, one peptide" approach in which a solid phase split synthesis scheme produced a library of peptides in which each bead in the collection had immobilized thereon a single, random sequence of amino acid residues. For the most part, the chemical synthetic systems have been directed to generation of arrays of short length peptides, generally fewer than about 10 amino acids or so, more particularly about 6–8 amino acids. Direct amino acid sequencing alone or in combination with complex record keeping of the peptide synthesis schemes is required. According to a second approach using recombinant DNA techniques, peptides have been expressed in vivo as either soluble fusion proteins or viral capsid fusion proteins. The second approach is discussed briefly below.

A number of peptide libraries according to the second approach have used the M13 phage. M13 is a filamentous bacteriophage that has been a workhorse in molecular biology laboratories for the past 20 years. The viral particles consist of six different capsid proteins and one copy of the viral genome, as a single-stranded circular DNA molecule. Once the M13 DNA has been introduced into a host cell such as E. coli, it is converted into double-stranded, circular DNA. The viral DNA carries a second origin of replication that is used to generate the single-stranded DNA found in the viral particles. During viral morphogenesis, there is an ordered assembly of the single-stranded DNA and the viral proteins, and the viral particles are extruded from cells in a process much like secretion. The M13 virus is neither lysogenic nor lytic like other bacteriophage (e.g., λ); cells, once infected, chronically release virus. This feature leads to high titers of virus in infected cultures, i.e., $10^{12}$ pfu/ml.

The genome of the M13 phage is ~8000 nucleotides in length and has been completely sequenced. The viral capsid protein, protein III (pIII) is responsible for infection of bacteria. In *E. coli*, the pillin protein encoded by the F factor interacts with pIII protein and is responsible for phage uptake. Hence, all *E. coli* hosts for M13 virus are considered male because they carry the F factor. Several investigators have determined from mutational analysis that the 406 amino acid long pIII capsid protein has two domains. The C-terminus anchors the protein to the viral coat, while portions of the N-terminus of pIII are essential for interaction with the *E. coli* pillin protein (Crissman, J. W. and Smith, G. P., 1984, Virology 132: 445–455). Although the N-terminus of the pill protein has shown to be necessary for viral infection, the extreme N-terminus of the mature protein does tolerate alterations. In 1985, George Smith published experiments reporting the use of the pill protein of bacteriophage M13 as an experimental system for expressing a heterologous protein on the viral coat surface (Smith, G. P., 1985, Science 228: 1315–1317). It was later recognized, independently by two groups, that the M13 phage pill gene display system could be a useful one for mapping antibody epitopes. De la Cruz, V., et al., (1988, J. Biol. Chem. 263: 4318–4322) cloned and expressed segments of the cDNA encoding the *Plasmodium falciparum* surface coat protein into the gene III, and recombinant phage were tested for immunoreactivity with a polyclonal antibody. Parmley, S. F. and Smith, G. P., (1988, Gene 73: 305–318) cloned and expressed segments of the *E. coli* β-galactosidase gene in the gene III and identified recombinants carrying the epitope of an anti-β-galactosidase monoclonal antibody. The latter authors also described a process termed "biopanning", in which mixtures of recombinant phage were incubated with biotinylated monoclonal antibodies, and phage-antibody complexes could be specifically recovered with streptavidin-coated plastic plates.

In 1989, Parmley, S. F. and Smith, G. P., (1989, Adv. Exp. Med. Biol. 251: 215–218), suggested that short, synthetic DNA segments cloned into the pIII gene might represent a library of epitopes. These authors reasoned that since linear epitopes were often ~6 amino acids in length, it should be possible to use a random recombinant DNA library to express all possible hexapeptides to isolate epitopes that bind to antibodies.

Scott and Smith (Scott, J. K. and Smith, G. P., 1990, Science 249: 386–390) describe construction and expression of an "epitope library" of hexapeptides on the surface of M13. The library was made by inserting a 33 base pair Bgl I digested oligonucleotide sequence into an Sfi I digested phage fd-tet, i.e., fUSE5 RF. The 33 base pair fragment contain a random or "degenerate" coding sequence $(NNK)_6$ where N represents G, A, T and C and K represents G and T. The authors stated that the library c on $2 \times 10^8$ recombinants expressing $4 \times 10_7$ different hexapeptides; theoretically, this library expressed 69% of the $6.4 \times 10^7$ possible peptides ($20^6$). Cwirla et al. (Cwirla, S. E., et al., 1990, Proc. Natl. Acad. Sci. USA 87: 6378–6382) also described a somewhat similar library of hexapeptides expressed as gene pIII fusions of M13 fd phage. WO91/19818 published Dec. 26, 1991 by Dower and Cwirla describes a similar library of pentameric to octameric random amino acid sequences.

Devlin et al., 1990, Science, 249: 404–406, describes a peptide library of about 15 residues generated using an (NNS) coding scheme for oligonucleotide synthesis in which S is G or C.

Christian and colleagues have described a phage display library, expressing decapeptides (Christian, R. B., et al., 1992, J. Mol. Biol. 227: 711–718). The starting DNA was generated by means of an oligonucleotide comprising the degenerate codons $[NN(G/T)]_{10}$ with a self-complementary 3' terminus. This sequence, in forming a hairpin, creates a self-priming replication site which could be used by T4 DNA polymerase to generate the complementary strand. The double-stranded DNA was cleaved at the SfiI sites at the 5' terminus and hairpin for cloning into the fUSE5 vector described by Scott and Smith, supra.

Other investigators have used other viral capsid proteins for expression of non-viral DNA on surface of phage particles. The protein pVIII is a major viral capsid protein and interacts with the single stranded DNA of M13 viral particles at its C-terminus. It is 50 amino acids long and exists in approximately 2,700 copies per particle. The N-terminus of the protein is exposed and will tolerate insertions, although large inserts have been reported to disrupt the assembly of fusion pVIII proteins into viral particles (Cesareni, G., 1992, FEBS Lett. 307: 66–70). To minimize the negative effect of pVIII-fusion proteins, a phagemid system has been utilized. Bacterial cells carrying the phagemid are infected with helper phage and secrete viral particles that have a mixture of both wild-type and fusion pVIII molecules. Gene VIII has also served as a site for expressing peptides on the surface of M13 viral particles. Four and six amino acid sequences corresponding to different segments of the *Plasmodium falciparum* major surface antigen have been cloned and expressed in the comparable gene of the filamentous bacteriophage fd (Greenwood, J., et al., 1991, J. Mol. Biol. 220: 821–827).

Lenstra, (1992, J. Immunol. Meth. 152: 149–157) describes construction of a library by a laborious process encompassing annealing oligonucleotides of about 17 or 23 degenerate bases with an 8 nucleotide long palindromic sequence at their 3' ends to express random hexa- or octa-peptides as fusion proteins with the β-galactosidase protein in a bacterial expression vector. The DNA was then converted into a double-stranded form with Klenow DNA polymerase, blunt-end ligated into a vector, and then released as HindIII fragments. These fragments were then cloned into an expression vector at the C-terminus of a truncated β-galactosidase to generate $10^7$ recombinants. Colonies were then lysed, blotted on nitrocellulose filters ($10^4$/filter) and screened for immunoreactivity with several different monoclonal antibodies. A number of clones were isolated by repeated rounds of screening and were sequenced.

Completely unlike the above discussed methods for generating a library of peptides which have been suggested for use to identify peptides having binding affinity for a chosen ligand, the present scheme for synthesis and assembly of the oligonucleotides provides sequences of oligonucleotides encoding unpredicted amino acid sequences which are larger in size, i.e., longer in length than any prior conventional libraries.

Completely contrary to the conventional teaching in the art that the length of inserted oligonucleotides should be kept small encoding preferably less than 15 and most preferably about 6–8 amino acids, the present inventors have found that not only can libraries encoding greater than about 22 amino acids be constructed, but that such libraries can be advantageously screened to identify TSARs or proteins, polypeptides and/or proteins having binding specificity for a variety of ligands.

Additionally, the longer length of the inserted synthesized oligonucleotides of the present libraries may provide the opportunity for the development of secondary and/or tertiary structure in the potential binding proteins/peptides and in sequences flanking the actual binding portion of the binding domain of the peptide. Such complex structural developments are not feasible when only shorter length oligonucleotides are used.

As understood in the art, there is a need to reduce TAG (stop) codon frequency in the oligonucleotides expressed by a peptide library. Those skilled in the art would expect to solve this problem by using hosts carrying suppressor tRNA genes. However, contrary to the conventional teaching, the present inventors have surprisingly discovered that suppression may not be 100% efficient to avoid stop codon expression in an oligonucleotide coding for a random peptide. This problem becomes very serious when expressing oligonucleotides of longer length encoding random peptides. The present invention effectively and efficiently minimizes the negative impact of such problem on the generation of a useful library.

Citation or identification of any reference in Section 2 of this application shall not be construed as an admission that such reference is available as prior art to the present invention.

3. SUMMARY OF THE INVENTION

The present invention provides methods and compositions, i.e., libraries, for identifying proteins/polypeptides and/or peptides called TSARs which bind to a ligand of choice. As used in the present invention, a TSAR is intended to encompass a concatenated heterofunctional protein, polypeptide and/or peptide that includes at least two distinct functional regions. One region of the heterofunctional TSAR molecule is a binding domain with affinity for a ligand, that is characterized by 1) its strength of binding under specific conditions, 2) the stability of its binding under specific conditions, and 3) its selective specificity for the chosen ligand. A second region of the heterofunctional TSAR molecule is an effector domain that is biologically or chemically active to enhance expression and/or detection and/or purification of the TSAR.

According to one embodiment of the invention, a TSAR can contain an optional additional linker domain or region between the binding domain and the effector domain. The linker region serves (1) as a structural spacer region between the binding and effector domains; (2) as an aid to uncouple or separate the binding and effector domains; or (3) as a structural aid for display of the binding domain and/or the TSAR by the expression vector.

The present invention further provides novel TSAR reagents as well as compositions comprising a binding domain of a TSAR or a portion thereof, all having specificity for a ligand of choice and methods for using TSARs and compositions comprising a binding domain of a TSAR, or a portion thereof which retains the binding specificity of the TSAR binding domain.

According to the methods of the invention, a library of recombinant vectors is generated or constructed to express a plurality of heterofunctional fusion proteins, polypeptides and/or peptide TSARs. In a preferred embodiment, the TSARs are expressed an the surface of the recombinant vectors of the library.

In order to prepare a library of recombinant vectors expressing a plurality of protein, polypeptide and/or peptide TSARs according to the present invention, single stranded sets of nucleotides are synthesized and assembled in vitro according to the following scheme.

The synthesized nucleotide sequences are designed to have both invariant nucleotide positions and variant or unpredicted nucleotide positions. The invariant nucleotides are positioned at particular sites in the nucleotide sequences to aid in assembly and cloning of the synthesized oligonucleotides. At the 5' termini of the sets of variant nucleotides, the invariant nucleotides encode for efficient restriction enzyme cleavage sites. The 3' termini invariant nucleotide positions are complementary pairs of 6, 9 or 12 nucleotides to aid in annealing two synthesized single stranded sets of nucleotides together and conversion to double-stranded DNA, designated herein synthesized double stranded oligonucleotides.

The scheme for synthesis and assembly of the unpredictable oligonucleotides used to construct the libraries of the present invention incorporates m+n variant, unpredicted nucleotide sequences of the formula $(NNB)_{n+m}$ into the coding stranded where B is G, T or C and n and m are each an integer, such that $20 \leq n+m \leq 200$ into the synthesized double stranded oligonucleotides, encoding the plurality of proteins, polypeptides and/or peptides.

The present invention provides methods for identifying a protein, polypeptide and/or peptide which binds to a ligand of choice, comprising: screening a library of vectors expressing a plurality of heterofunctional fusion proteins containing (a) a binding domain encoded by a double stranded oligonucleotide assembled by annealing a first nucleotide sequence of the formula 5'X $(NNB)_n$ J Z 3' with a second nucleotide sequence of the formula 3'Z'O U $(NNV)_m$ Y 5' where X and Y are restriction enzyme recognition sites, such that X≈Y;

N is A, C, G or T;

B is G, T or C;

V is G, A or C;

n is an integer, such that $10 \leq n \leq 100$;

m is an integer, such that $10 \leq m \leq 100$;

Z and Z' are each a sequence of 6, 9 or 12 nucleotides, such that

Z and Z' are complementary to each other; and

J is A, C, G, T or nothing;

O is A, C, G, T or nothing; and

U is G, A, C or nothing; provided, however, if any one of J, O or U is nothing then J, O and U are all nothing, and converting the annealed nucleotide sequences to a double stranded oligonucleotide, and (b) an effector domain encoded by an oligonucleotide sequence encoding a protein or peptide that enhances expression or detection of the binding domain, by contacting the plurality of heterofunctional fusion proteins with said ligand of choice under conditions conducive to ligand binding and isolating the heterofunctional fusion protein which binds said ligand.

The present invention further encompasses methods for preparing a protein, polypeptide and/or a peptide which binds to a ligand of choice, comprising synthesizing, either chemically or by recombinant techniques, the amino acid sequence identified by screening a library of vectors of the invention.

3.1. OBJECTS AND ADVANTAGES OF THE INVENTION

The present invention provides a method for identifying a binding molecule, that is reproducible, quick, simple, efficient and relatively inexpensive. More particularly, the invention provides a method of generating and screening a large library of diverse protein, polypeptide and/or peptide molecules. Thus, the invention provides a rapid and easy way of producing a large library that results in a plurality of longer proteins, polypeptides and/or peptides that can efficiently be screened to identify those with novel and improved binding specificities, affinities and stabilities for a given ligand of choice. The diversity of binding characteristics that can be obtained with the other binding molecules that are formed in vivo.

In contrast to methods that rely on isolation of specific genes and known sequences, the present invention has the advantage that there is no need for purifying or isolating genes nor any need for detailed knowledge of the function of portions of the binding sequence or the amino acids that are involved in ligand binding in order to produce a TSAR. The only requirement is having the ligand needed to screen a TSAR library to find TSARs with affinity for that ligand. Since TSARs are screened in vitro, the solvent requirements involved in TSAR/ligand interactions are not limited to aqueous solvents; thus, nonphysiological binding interactions and conditions different from those found in vivo can be exploited.

The variant nucleotides, according to the present scheme, encode all twenty naturally occurring amino acids by use of 48 different codons. Although this affords somewhat less variability than found in nature, in which 64 different codons are used, the present scheme for designing the variant nucleotides advantageously provides greater variability than in conventional schemes such as those which use nucleotides of other formulas.

Use of the presently taught NNB scheme is particularly advantageous by minimizing the number of recombinants with internal stop codons. This difference becomes magnified when longer peptides are expressed. This becomes especially important where the size of the inserted oligonucleotides is large, e.g., greater than about 20 codons. For example, using the presently taught method, in an oligonucleotide of 100 codons, the probability of not having a stop codon, i.e., of having an open reading frame, would be $(47/48)^{100}$ or about 12% whereas using the (NNS) or (NNK) method, such probability would be $(31/32)^{100}$ or about only 4%. The NNN scheme could be used, but there would be a terrific increase in the number of recombinants with stop codons, i.e., the frequency of not having a stop codon would be $(61/64)^{100}$ or less than about 1%.

The NNB scheme offers additional flexibility when the TSAR peptides are expressed in hosts that lack suppressor tRNA genes. That is, the NNB scheme is not restricted to host organisms that have been subject to intense molecular genetic manipulation and thus offers greater flexibility in host selection.

One could avoid stop codons altogether by use of codon triplets, but then one would need to know codon preference ideally for each host. NNB offers greater flexibility in host range. In addition, oligonucleotides in codon triplet form are not commercially available and the chemistry to synthesize triplets is cumbersome.

Additionally, the present scheme avoids the use of synthesized oligonucleotides rich in GC nucleotides such as is often found in libraries using an NNS formula for variant codons. Such oligonucleotides are difficult to assemble and sequence properly.

Perhaps most significantly, the present scheme for synthesis and assembly of the oligonucleotides provides sequences of oligonucleotides encoding unpredicted amino acid sequences which are larger in size than any prior conventional libraries. As constructed according to the present invention, the present synthesized double stranded oligonucleotides comprise at least about 77–631 nucleotides in length encoding the restriction enzyme sites, the complementary site and about 20–200 unpredicted amino acids in the TSAR binding domain. According to a preferred embodiment, n and m are greater than or equal to 10 and less than or equal to 50. Thus, the synthesized double stranded oligonucleotides comprise at least 77–331 nucleotides and encode about 20–100 unpredicted amino acids in the TSAR binding domain. In the specifically exemplified examples, the synthesized oligonucleotides encode respectively, 27 and 42 amino acids in the TSAR binding domain.

Completely contrary to the conventional teaching in the art that the length of inserted oligonucleotides should be kept small encoding preferably less than 15 and most preferably about 6–8 amino acids, the present inventors have found that not only can libraries encoding greater than about 22 amino acids be constructed, but that such libraries can be advantageously screened to identify TSARs or proteins, polypeptides and/or proteins having binding specificity for a variety of ligands.

Additionally, the longer length of the inserted synthesized oligonucleotides of the present libraries may provide the opportunity for the development of secondary and/or tertiary structure in the potential binding proteins/peptides and in sequences flanking the actual binding portion of the binding domain of the peptide. Such complex structural developments are not feasible when only shorter length oligonucleotides are used.

TSARs are particularly useful in systems in which development of binding affinities for a new substance and developing different binding affinities for known substances are desirable.

TSARs or compositions comprising the binding domain of a TSAR (or a portion thereof having the same binding specificity) may be used in any in vivo or in vitro application that might make use of a peptide or polypeptide with binding affinity. Thus, TSARs or the TSAR compositions can be used in place of or to bind to a cell surface receptor, a viral receptor, an enzyme, a lectin, an integrin, an adhesin, a $Ca^{++}$ binding protein, a metal binding protein, DNA or RNA binding proteins, immunoglobulins, vitamin cofactors, peptides that recognize any bioorganic or inorganic compound, etc.

By virtue of the affinity for a target, TSARs or compositions comprising a TSAR binding domain or a portion thereof used in vivo can deliver a chemically or biologically active moiety, such as a metal ion, a radioisotope, peptide, toxin or fragment thereof, or enzyme or fragment thereof, to the specific target in or on the cell. The TSARs can also have in vitro a utility similar to monoclonal antibodies or other specific binding molecules for the detection, quantitation, separation or purification of other molecules. In one embodiment, a number of TSARs or the binding domains thereof can be assembled as multimeric units to provide multiple binding domains that have the same specificity and can be fused to another molecule that has a biological or chemical activity.

The TSARs that are produced in this invention can replace the function of macromolecules such as monoclonal or polyclonal antibodies and thereby circumvent the need for the complex methods for hybridoma formation or in vivo antibody production. Moreover, TSARs differ from other natural binding molecules in that TSARs have an easily characterized and designed activity that can allow their direct and rapid detection in a screening process.

4. BRIEF DESCRIPTION OF THE FIGURES

The present invention may be understood more fully by reference to the following detailed description of the invention, examples of specific embodiments of the invention and the appended figures in which:

FIG. 1 (A–F) schematically illustrates construction of TSAR libraries according to the methods of the invention. FIG. 1A schematically depicts the synthesis and assembly of synthetic oligonucleotides for the linear libraries and bimolecular libraries illustrated in FIG. 1B and 1C. N=A, C, G or T; B=G, T or C and V=G, A, or C; and n and m are integers, such that $10 \leq n \leq 100$ and $10 \leq m \leq 100$; Z and Z' are each 6, 9 or 12 nucleotides, such that Z and Z' are complementary to each other, J is A, C, G, T or nothing; O is A, C, G, T or nothing; and U is G, A, C or nothing, provided, however, if any one of J, O or U is nothing then J, O and U are all nothing. FIG. 1D–F schematically depicts representative libraries which are designed to be rigid libraries. The synthesis and assembly of the oligonucleotides for the rigid libraries are as in FIG. 1A with modifications to include specified invariant positions. See Section 5.1 text for details.

Figure 2:
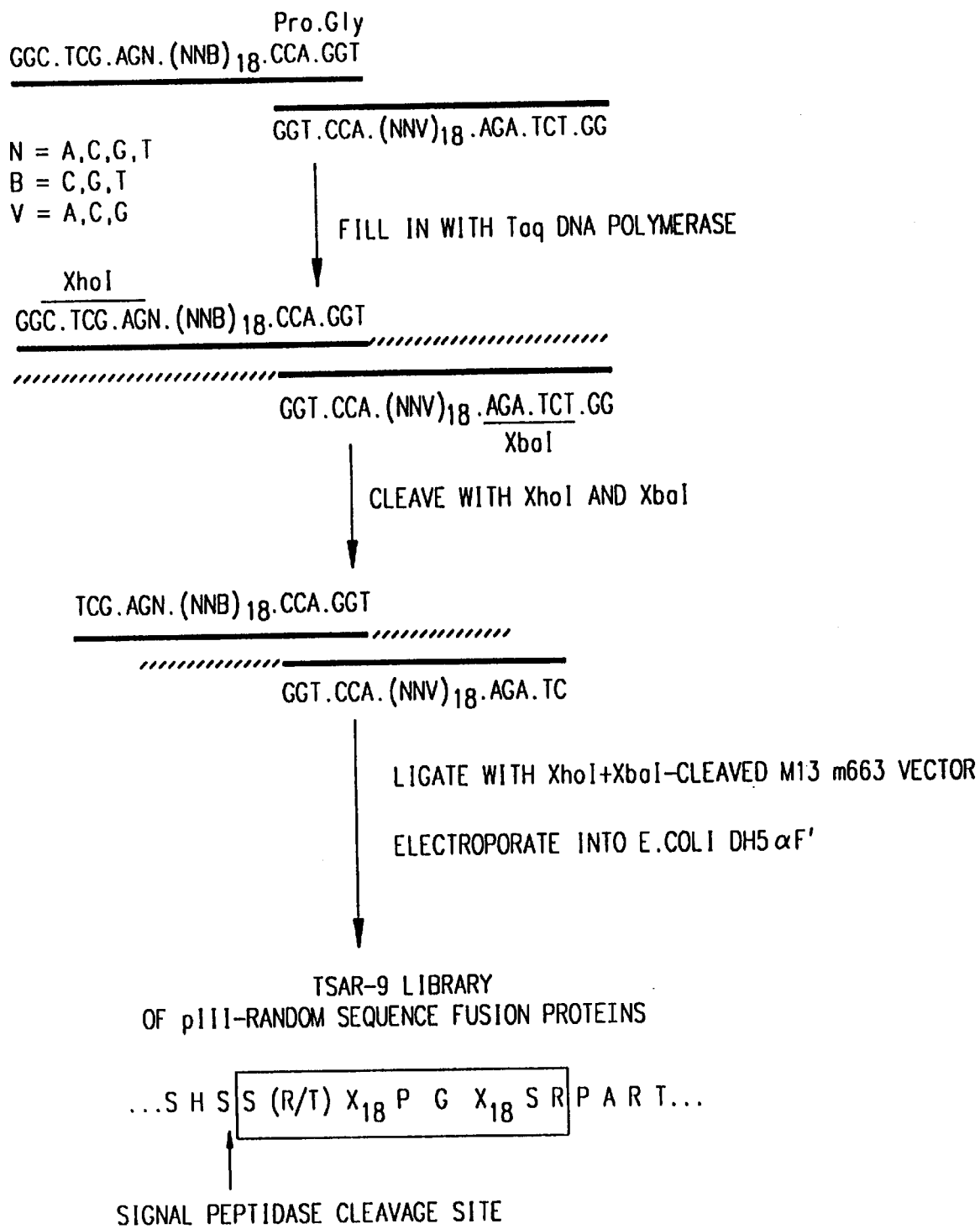

FIG. 2 schematically illustrates construction of the TSAR-9 library. N=A, C, G or T; B=G, T or C and V=G, A or C. See text Section 6.1.1 for details.

Figure 3:
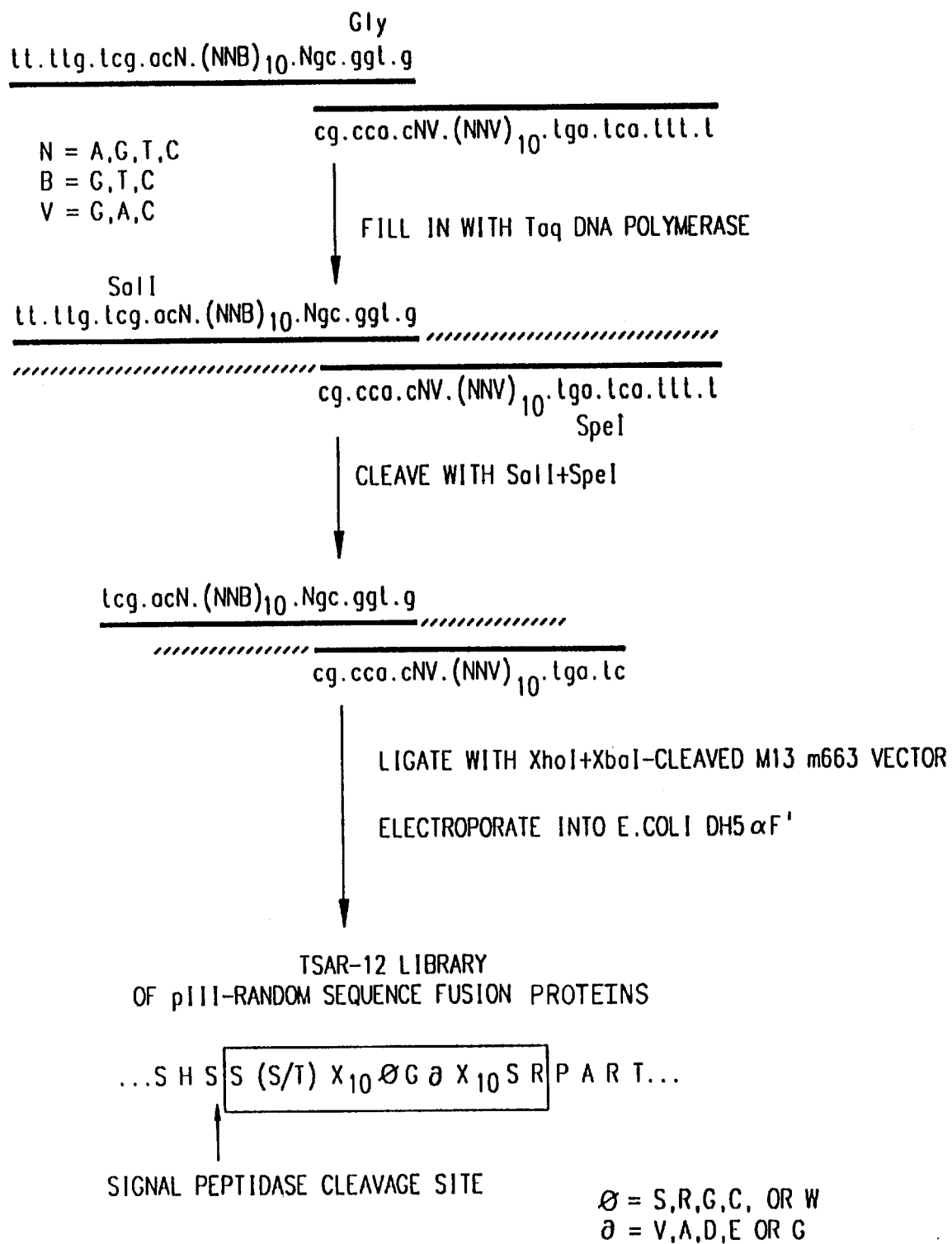

FIG. 3 schematically illustrates construction of the TSAR-12 library. N=A, C, G or T; B=G. T or C and V=G, A or C. See text Section 6.2 for details. insertion into a representative, appropriate vector and expression in an appropriate host is illustrated.

Figure 4:
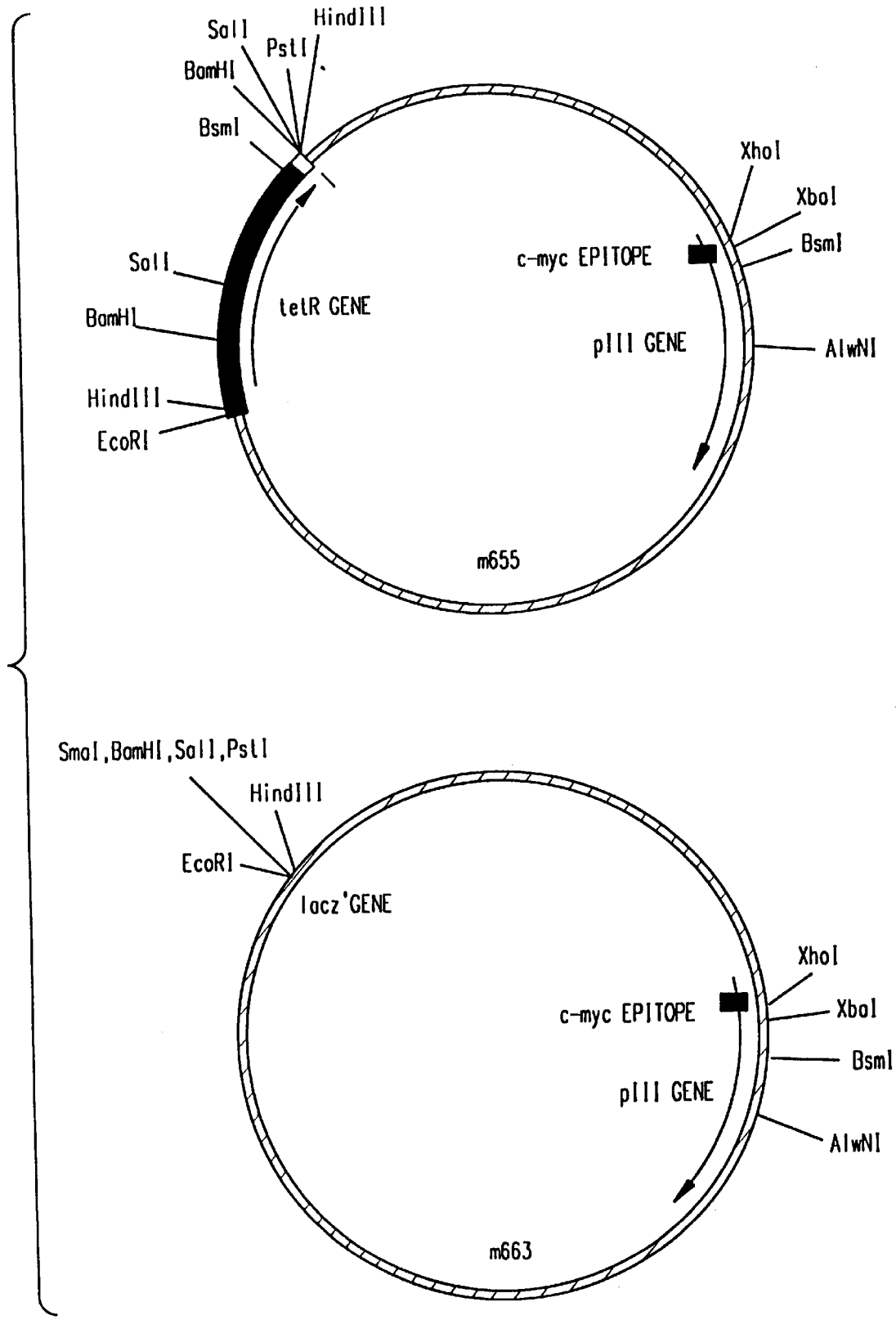

FIG. 4 depicts maps of derivatives of m13mp8, vectors m655 and m663, (see Fowlkes et al., 1992, BioTechniques, 13: 422–427)

Figure 5D:
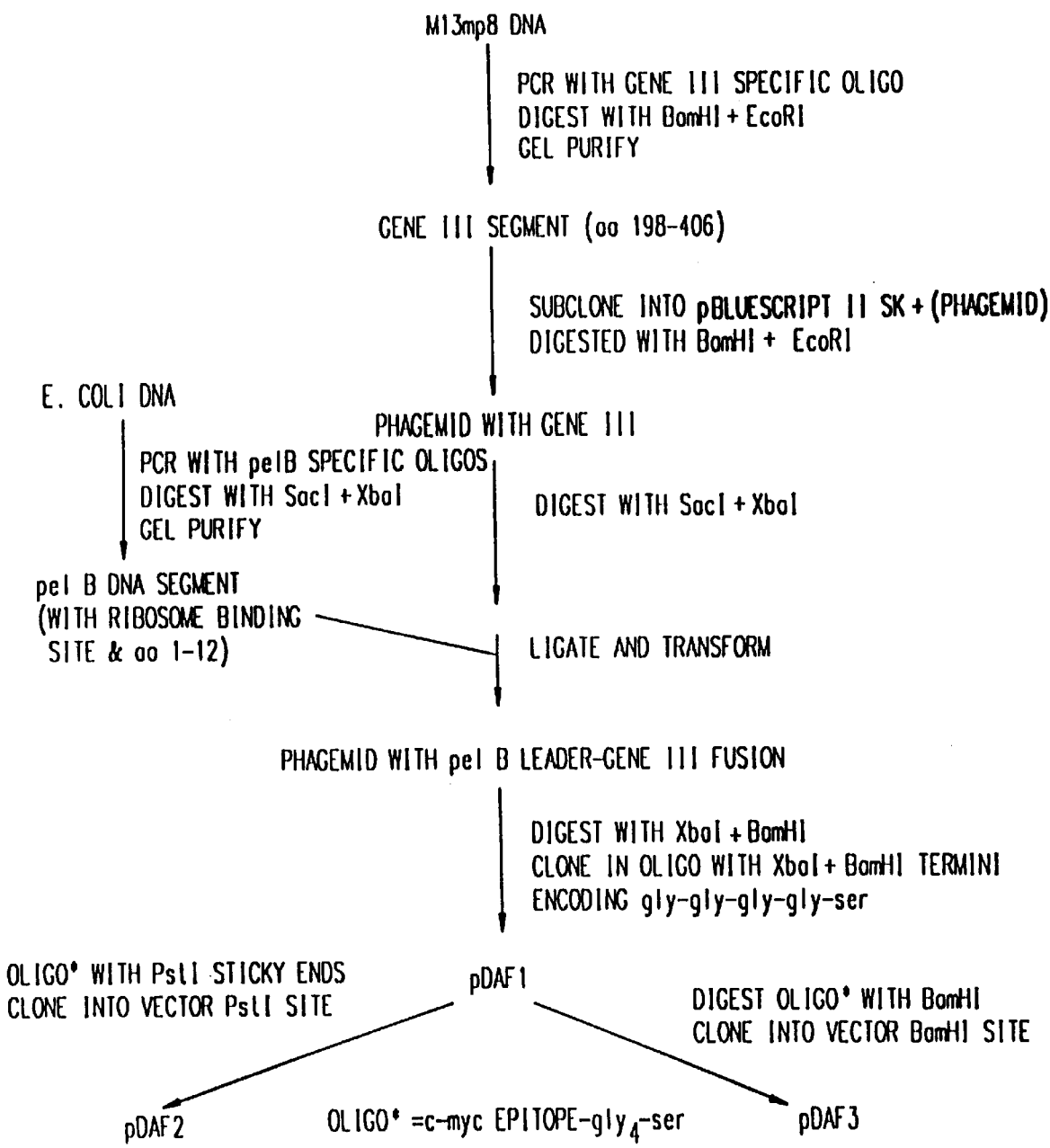

FIG. 5 (A–D) represents circular restriction maps of phagemid vectors, derived from phagemid pBluescript II SK$^+$, in which a truncated portion encoding amino acid residues 198–406 of the pIII gene of M13 is linked to a leader sequence of the E. coli Pel B gene and is expressed under control of a lac promoter. G and S represent the amino acids glycine and serine, respectively; c-myc represents the human c-myc oncogene epitope recognized by the 9E10 monoclonal antibody described in Evan et al., 1985, Mol. Cell. Biol. 5: 3610–3616. FIG. 5A illustrates the restriction map of phagemid pDAF1; FIG. 5B illustrates the restriction map of phagemid pDAF2; FIG. 5C illustrates the restriction map of phagemid pDAF3; FIG. 5D schematically illustrates the construction of phagemids pDAF$_1$, pDAF$_2$ and pDAF$_3$.

Figure 6A:
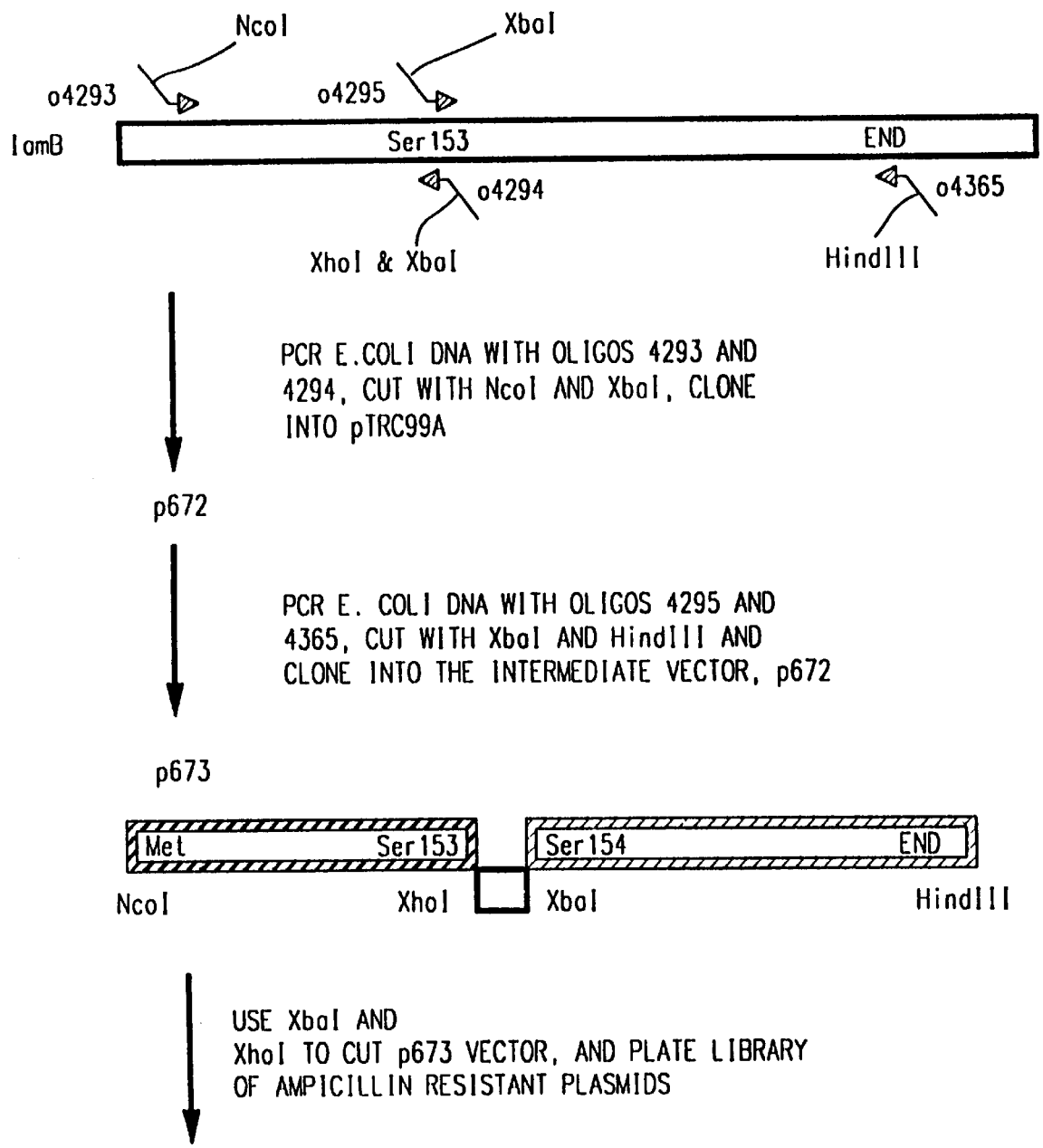
Figure 6B:
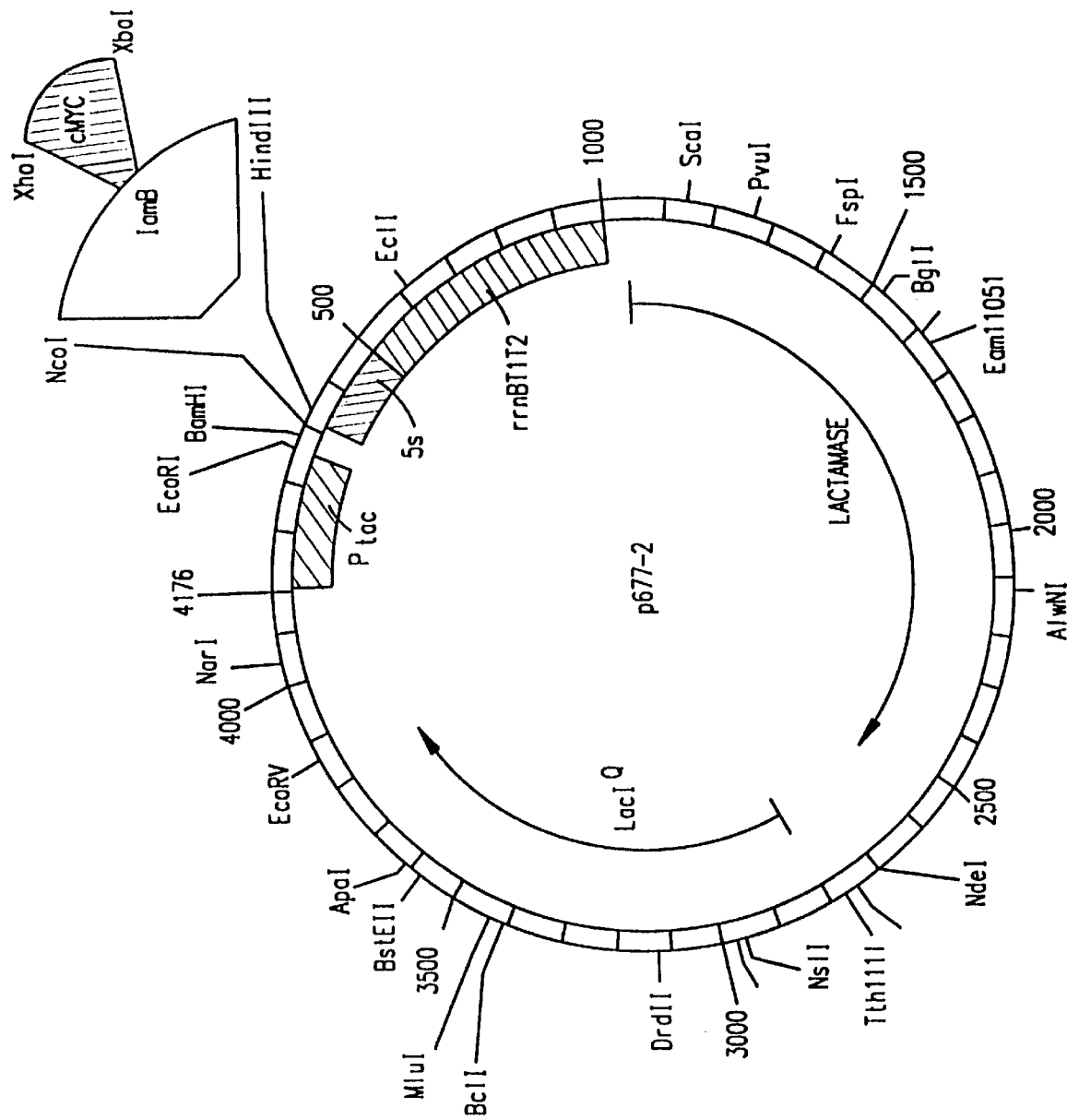

FIG. 6(A–B) depicts the steps in construction of (FIG. 6A) and structure of FIG. 6B expression vector plasmid p677–2. See text Section 5.1.2.1 for details.

Figure 7:
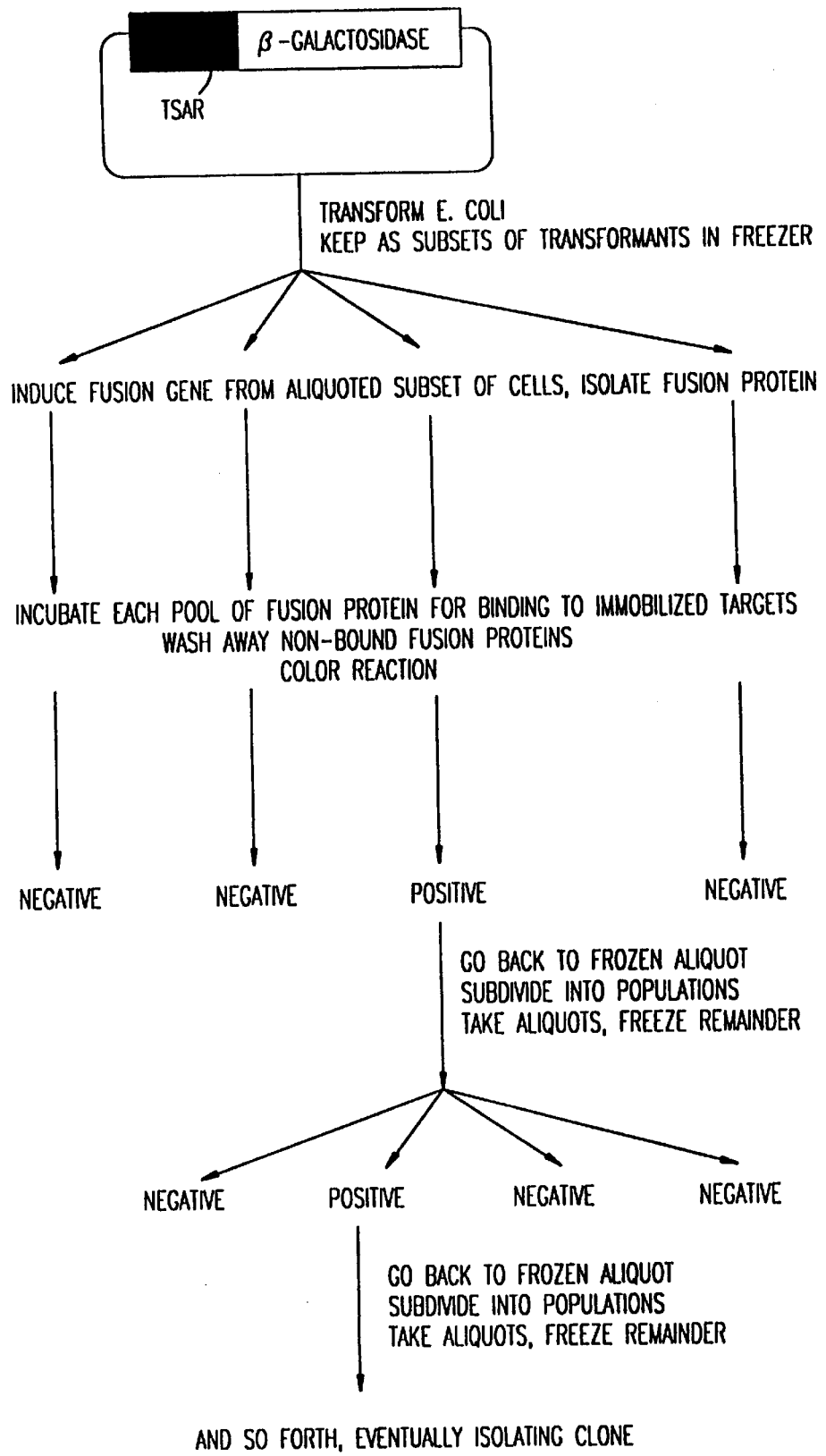

FIG. 7 schematically presents a scheme for screening a TSAR library expressed in a plasmid vector. See text Section 5.2 for details.

Figure 8:
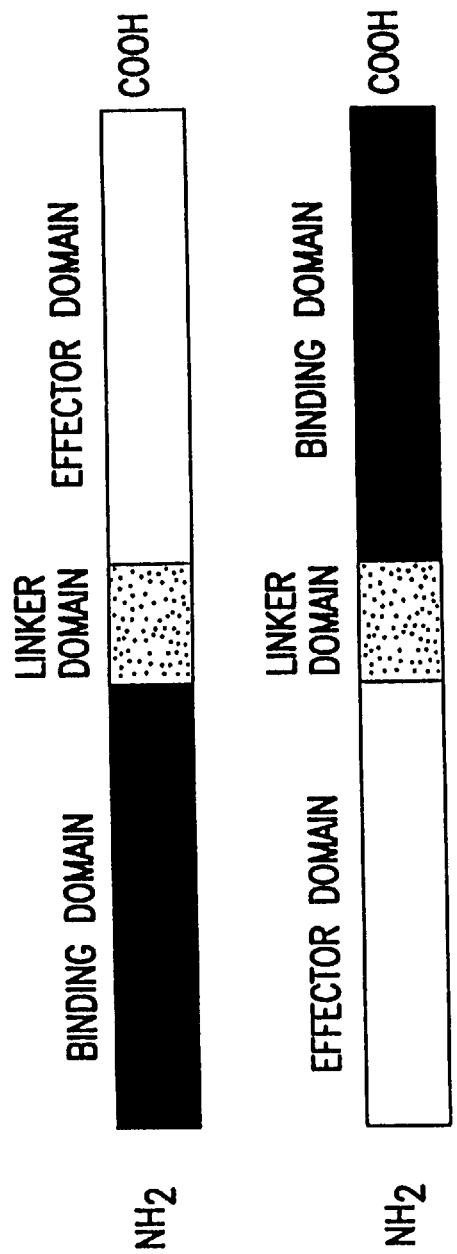

FIG. 8 schematically represents TSARs in which a linker domain joins the binding domain and the effector domain. The schematic illustration is not necessarily drawn to scale. See text Section 5.3 for details.

Figure 9:
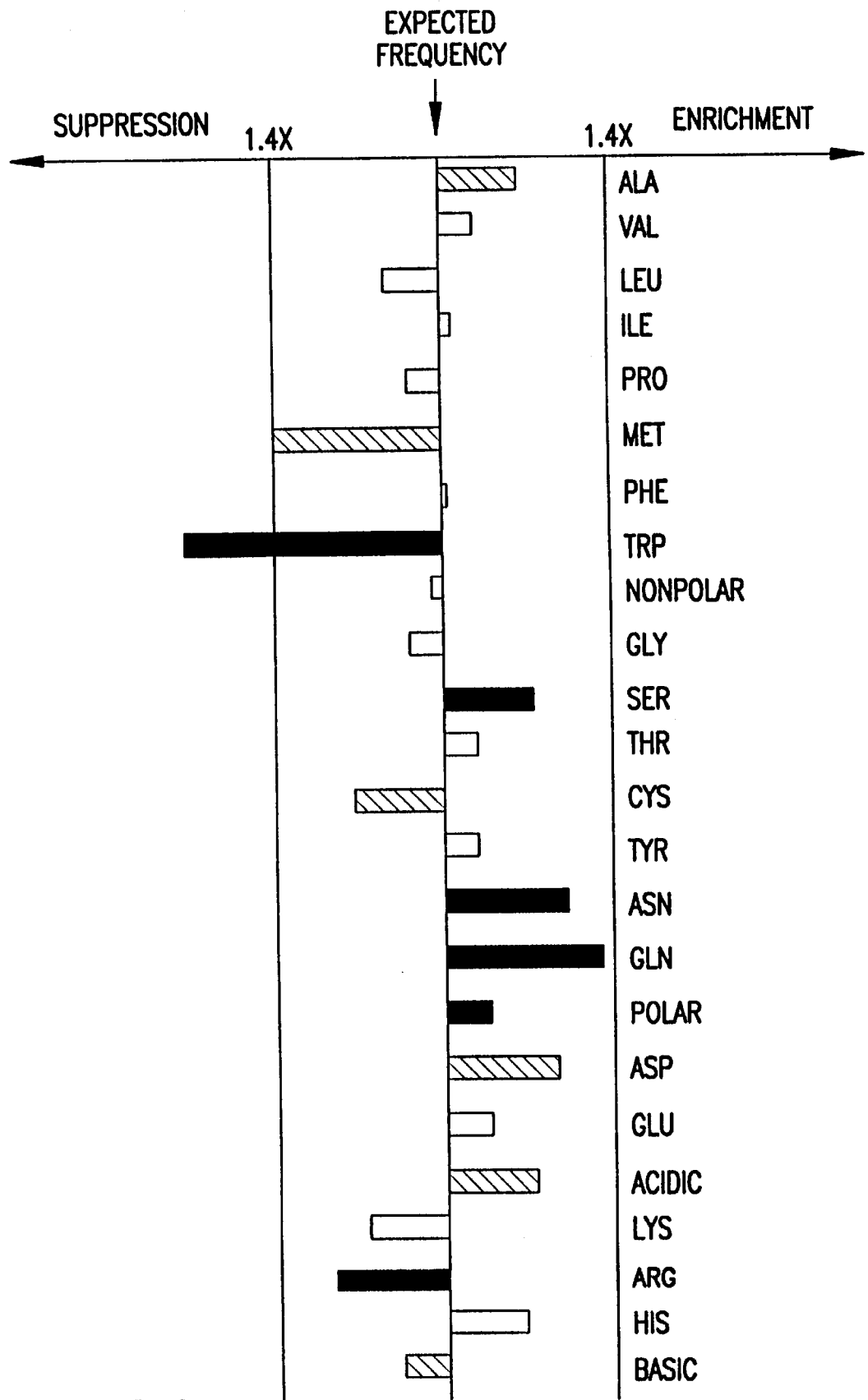

FIG. 9 presents the usage frequency of amino acids encoded by the variant regions of the synthetic oligonucleotides of 23 randomly chosen members of the TSAR-9 library. The values presented compare the number of times each amino acid was observed with that predicted based on the formula used to synthesize the oligonucleotides; the divergence from the predicted values is represented by the size of the bars above and below the baseline. See text Section 6.3.1 for details.

Figure 10:
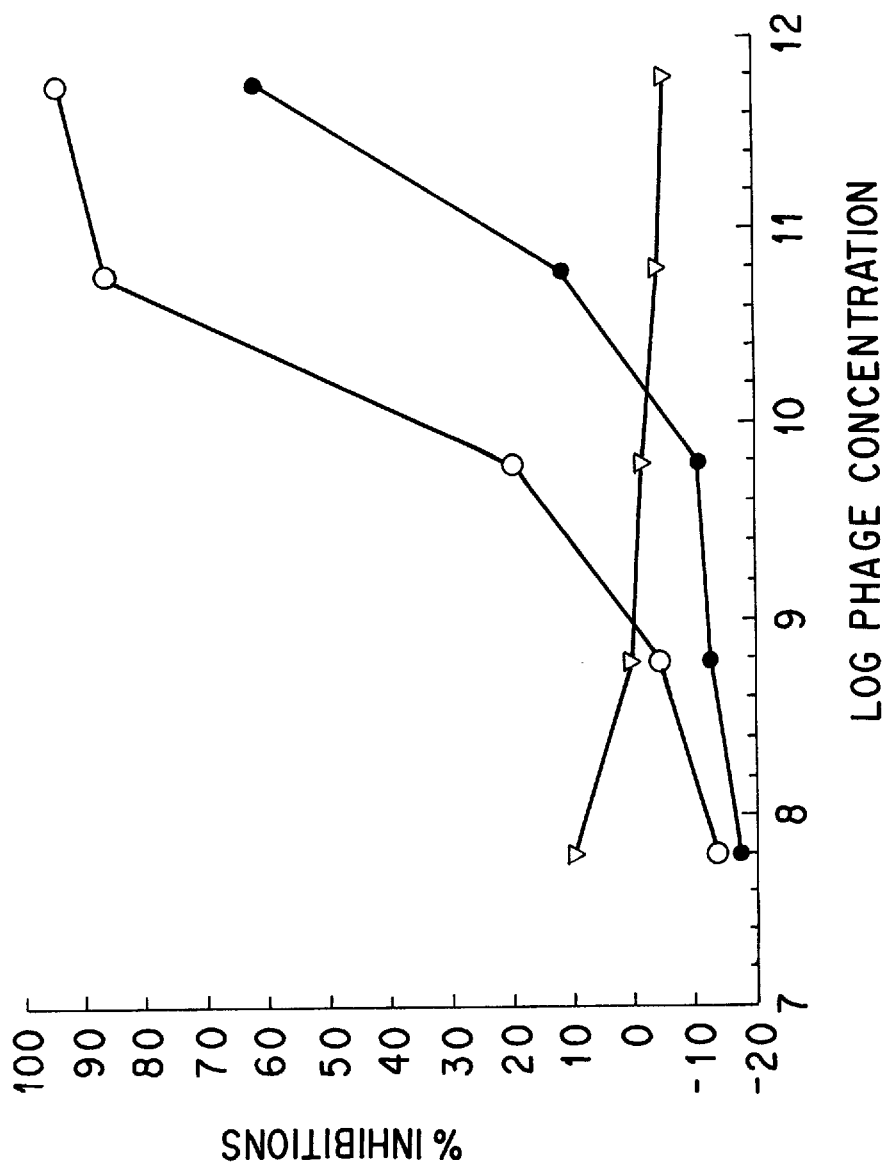

FIG. 10 demonstrates that TSARs, expressed on phage vectors, designated 7E11.9-5 and 7E11.12-3 (SEQ ID NOS: 26 and 29, respectively) inhibited the binding of the 7E11-C5 monoclonal antibody to its antigen in a dose dependent manner. O represents competition of binding by TSAR 7E11.9-5 (IC 50=$1.7 \times 10^{10}$); ● represents competitive inhibition of binding by TSAR 7E11.12-3 (IC 50=$3.55 \times 10^{11}$); ▽ represents competitive inhibition of binding by the pIII gene of vector M663, a control protein. See text Section 7.2 for details.

Figure 11:
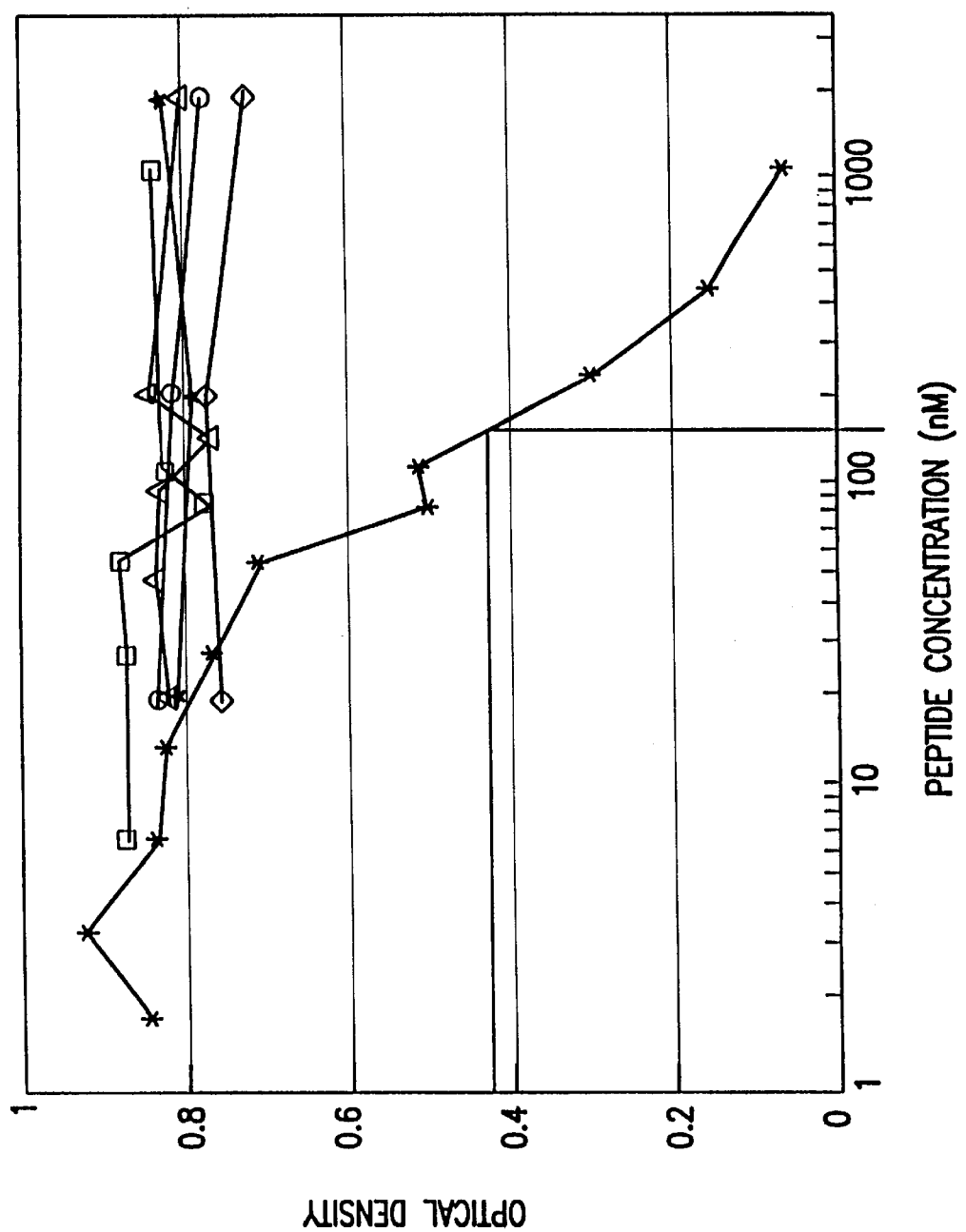

FIG. 11 demonstrates that a peptide (amide form) (SEQ ID NO 31) comprising a portion of the binding domain of a 7E11-C5 binding TSAR competitively inhibited binding of the 7E11-C5 antibody to its antigen. Two (amide form) control peptides 1 and 2 (SEQ ID NOS: 32 and 33) were included for comparison. The ability to inhibit binding of B139, another monoclonal antibody which recognizes an antigen in the LNCaP cell extract different from that recognized by the 7E11-C5 antibody was also evaluated. * represents inhibition of 7E11-C5 monoclonal antibody binding to the LNCaP cell extract by SEQ ID NO 31; □, inhibition of B139 monoclonal antibody binding to the LNCaP cell extract by SEQ ID NO 31; ◇ represents inhibition of 7E11-C5 monoclonal antibody binding by control peptide 1 SEQ ID NO 32; ▲ represents inhibition of B139 monoclonal antibody binding by control peptide 1 SEQ ID NO 32; ⊖ represents inhibition of 7E11-C5 monoclonal antibody by control peptide 2 SEQ ID NO 33; and ✽ represents inhibition of B139 monoclonal antibody by control peptide 2 SEQ ID NO 33. See text Section 7.2 for details.

Figure 12:
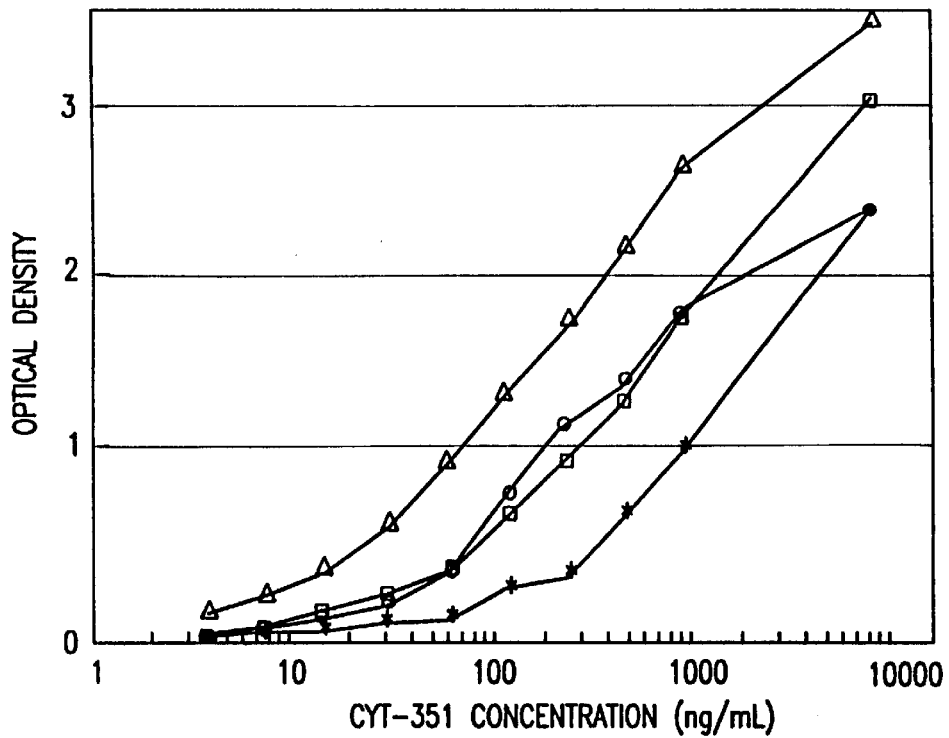

FIG. 12 demonstrates dose dependent binding of the 7E11-C5 monoclonal antibody to a peptide comprising a portion of a 7E11-C5 binding TSAR, the peptide designated (amide) SEQ ID NO 31 when immobilized using 50 μl/well at concentrations ranging from 0.5–500 μg/ml. ⊖ represents SEQ ID NO 31 at 0.5 μg/ml; ▲ represents SEQ ID NO 31 at 5.0 μg/ml; ⊟ represents SEQ ID NO 31 at 50 μg/ml; and * represents SEQ ID NO 31 at 500 μg/ml, See text Section 7.2 for details.

Figure 13:
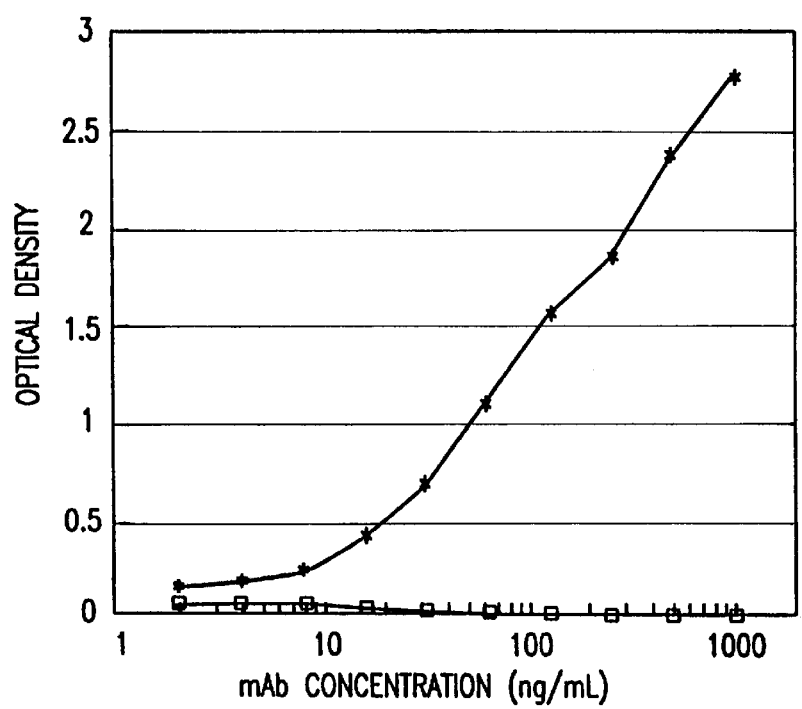

FIG. 13 demonstrates that the 7E11-C5 monoclonal antibody specifically binds to a peptide comprising a portion of a 7E11-C5 binding TSAR, the peptide designated (amide form) SEQ ID NO 31 whereas another, irrelevant monoclonal antibody B139 did not. * represents binding of 7E11-C5 antibody to immobilized SEQ ID NO 31; ⊟ represents binding of B139 antibody to immobilized SEQ ID NO 31.

Figure 14A:
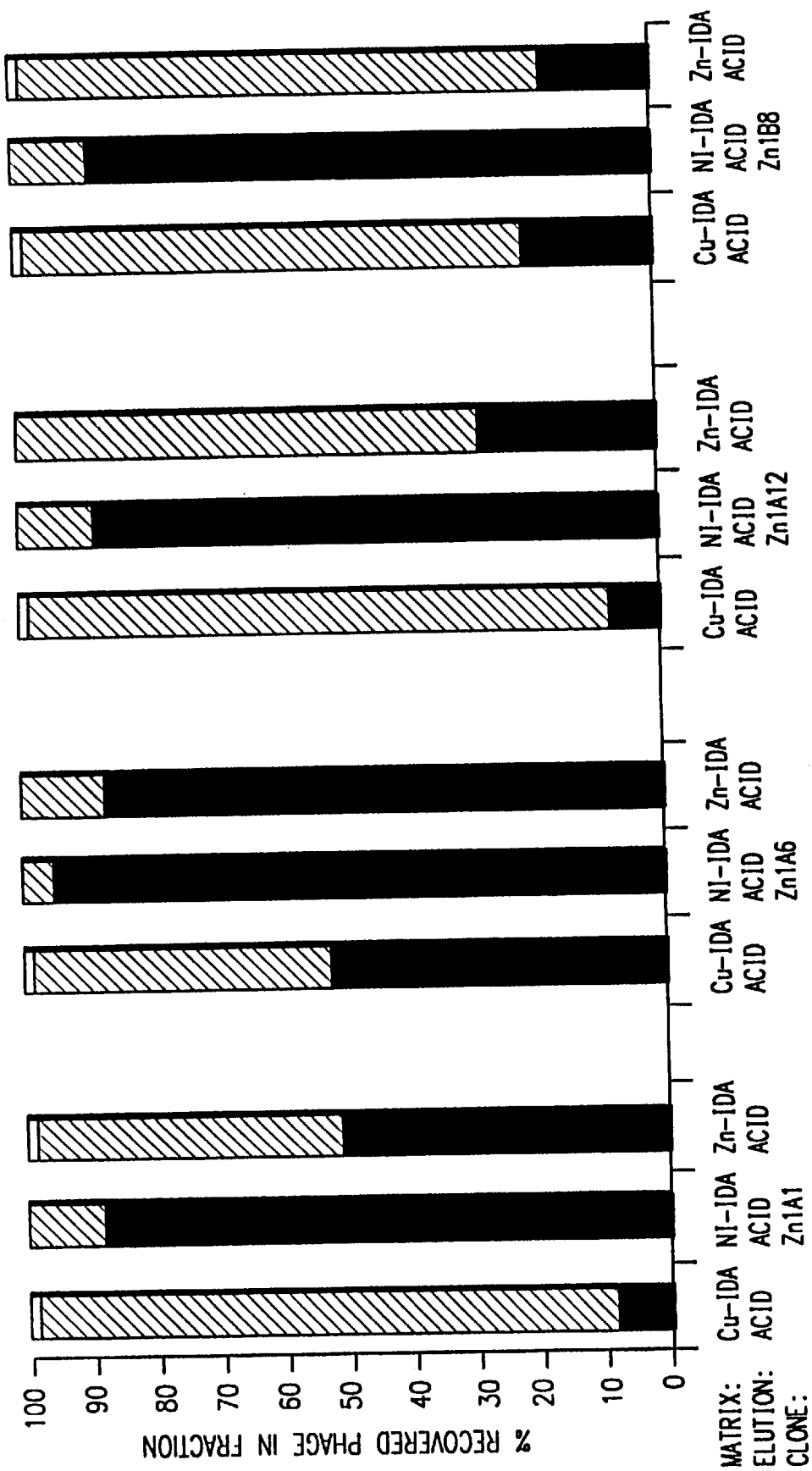
Figure 14B:
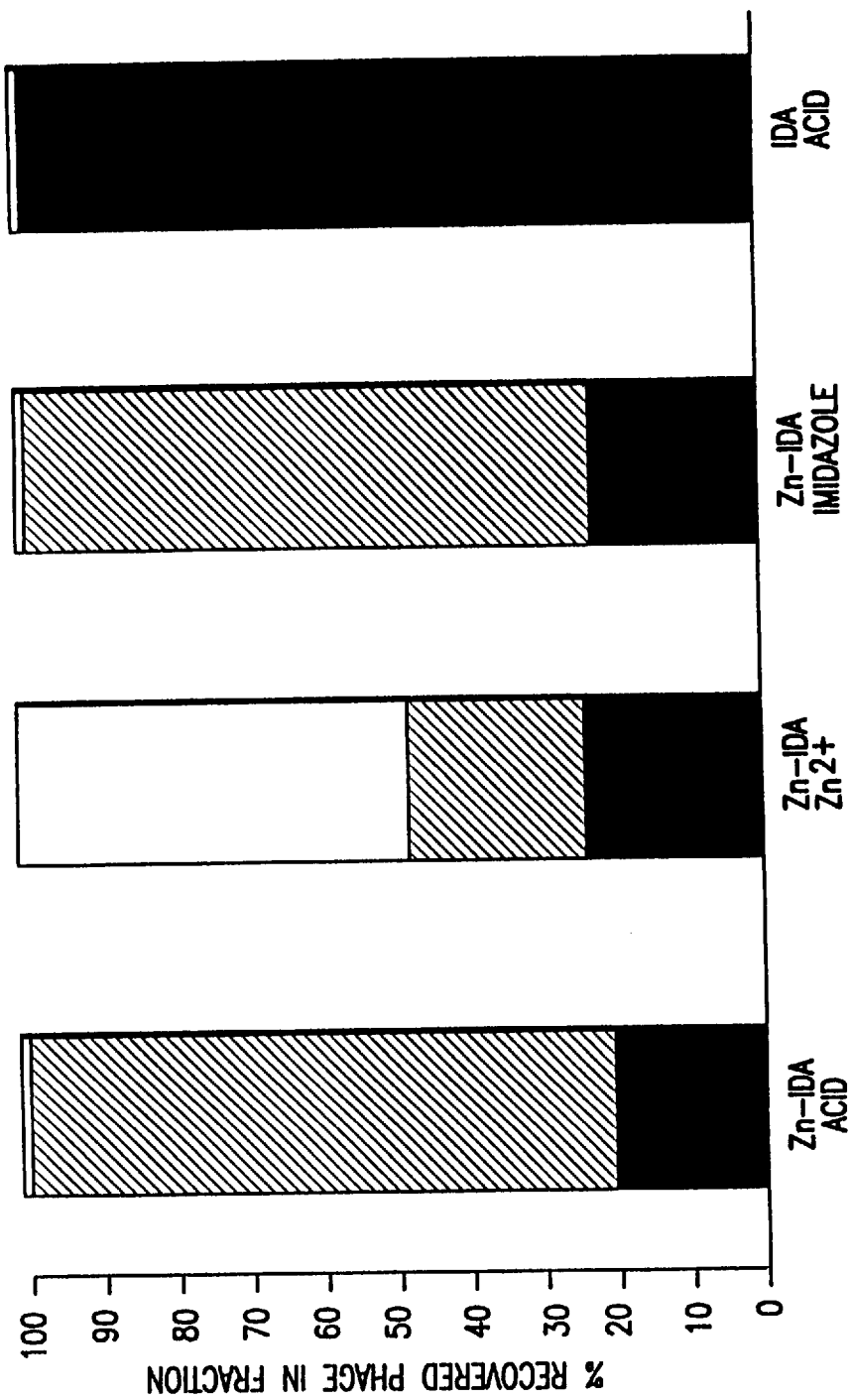

FIG. 14 (A–B) diagrammatically shows chromatographic characteristics of isolated Zn(II)-IDA-selected phage fractionated on Zn(II)-IDA, Cu(II)-IDA, and Ni(II)-IDA. FIG. 14A shows four Zn(II)-IDA-selected phage (Table 2) chosen for further characterization. The clones were fractionated on Zn(II)-IDA, Cu(II)-IDA, and Ni(II)-IDA. Three fractions were collected and titered for the presence of phage: the wash (■), the elution (▨), and the metal(II)-IDA column matrix resuspended in T10NT (□). The percentage of recovered phage in each fraction is indicated. FIG. 14B shows elution of Zn(II)-IDA-selected clone Zn 1B8 from Zn(II)-IDA. Zn1B8 was fractionated over Zn(II)IDA- and eluted with various reagents. Three fractions were collected and titered for the presence of phage: the wash fraction (■), the elution fraction (▣), and the metal(II)-IDA column matrix resuspended in T10NT (□). Values are presented as percent recovered phage in fraction. See text Section 7.3 for details.

Figure 15:
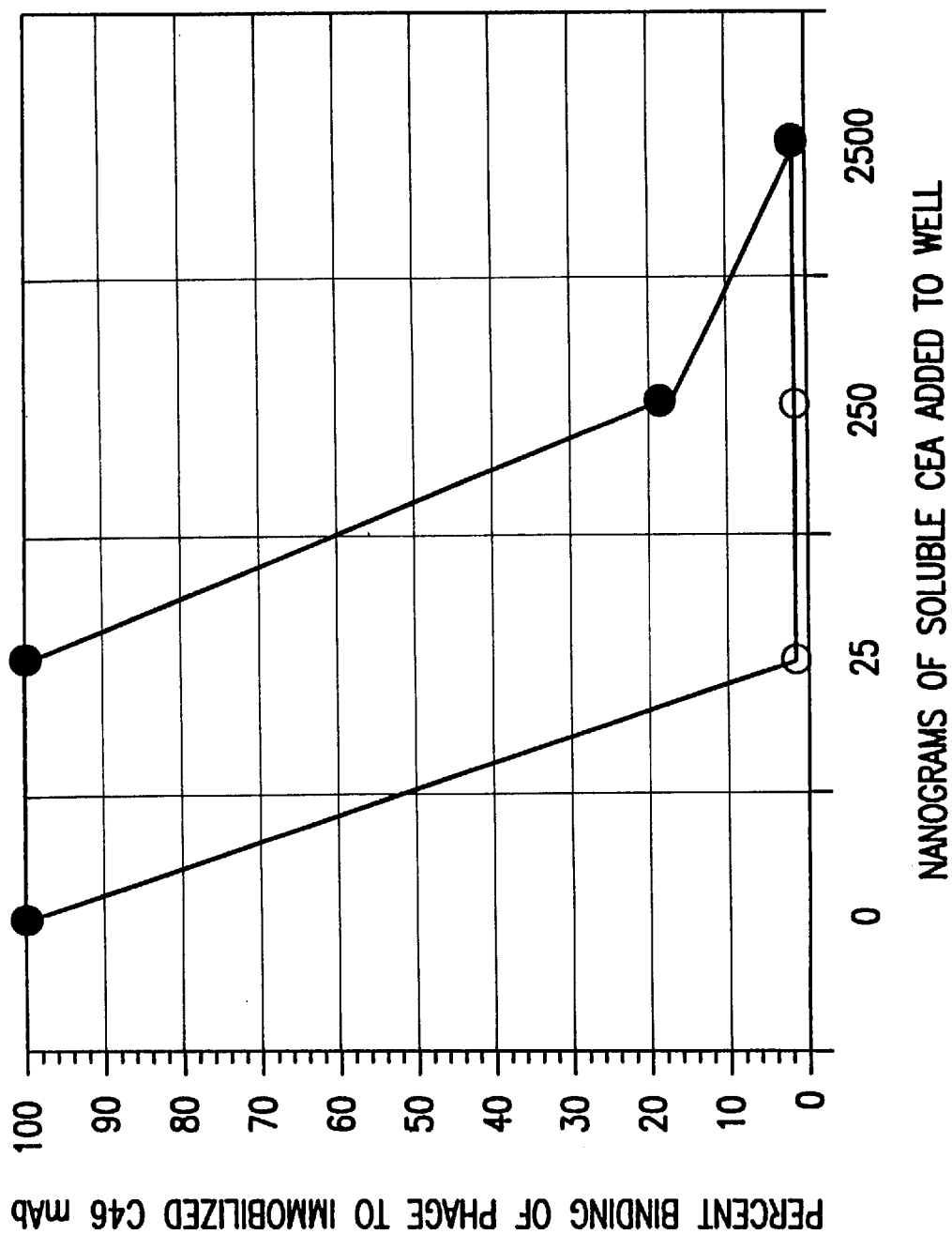

FIG. 15 demonstrates competitive binding of TSARs designated C46-9.1 (SEQ ID NO 68) (●) C46-9.2 (SEQ ID NO 69) (○) with carcinoembryonic antigen (CEA) for the C46 monoclonal antibody. See text Section 7.5 for details.

Figure 16:
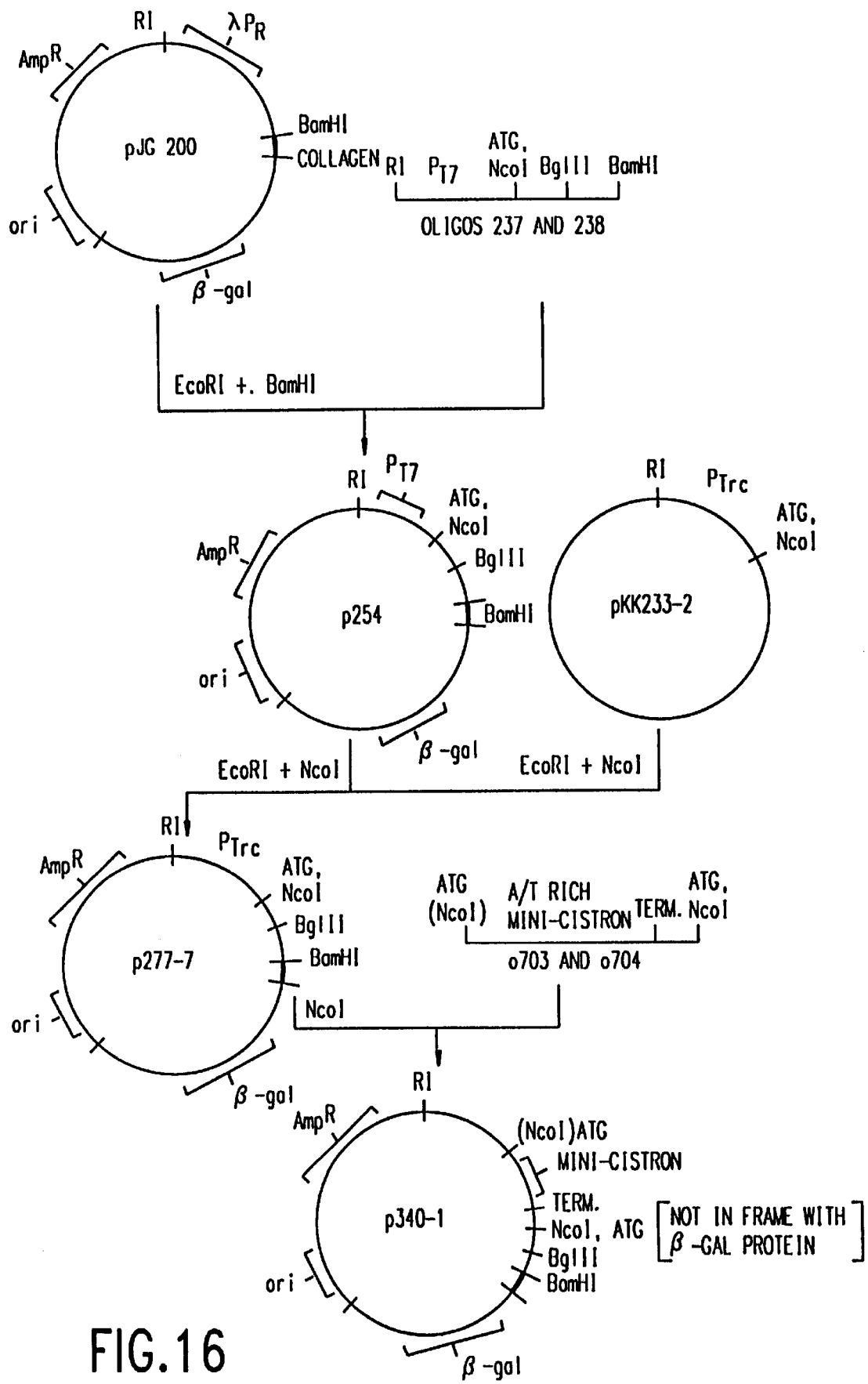

FIG. 16 depicts the steps in construction of the plasmid expression vector p340. See text Section 9 for details.

5. DETAILED DESCRIPTION OF THE INVENTION

The present invention provides methods and compositions for identifying proteins/polypeptides and/or peptides called TSARs which bind to a ligand of choice. As used in the present invention, a TSAR is intended to encompass a concatenated heterofunctional protein, polypeptide and/or peptide that includes at least two distinct functional regions. One region of the heterofunctional TSAR molecule is a binding domain with affinity for a ligand, that is characterized by 1) its strength of binding under specific conditions, 2) the stability of its binding under specific conditions, and 3) its selective specificity for the chosen ligand. A second region of the heterofunctional TSAR molecule is an effector domain that is biologically or chemically active to enhance expression and/or detection and/or purification of the TSAR. The effector domain is chosen from a number of biologically or chemically active proteins including a structural protein or fragment that is accessibly expressed as a surface protein of a vector, an enzyme or fragment thereof, a toxin or fragment thereof, a therapeutic protein or peptide, or a protein or peptide whose function is to provide a site for attachment of a substance such as a metal ion, etc., that is useful for enhancing expression and/or detection and/or purification of the expressed TSAR.

According to one embodiment of the invention, a TSAR can contain an optional additional linker domain or region between the binding domain and the effector domain. The linker region serves (1) as a structural spacer region between the binding and effector domains; (2) as an aid to uncouple or separate the binding and effector domains; or (3) as a structural aid for display of the binding domain and/or the TSAR by the expression vector. See Section 5.3 (infra) for a more detailed description of the optional linker region of the TSARs (also see FIG. 8).

As used in the present invention, a ligand is intended to encompass a substance, including a molecule or portion thereof, for which a proteinaceous receptor naturally exists or can be prepared according to the method of the invention. A TSAR which binds to a ligand can function as a receptor, i.e., a lock into which the ligand fits and binds; or a TSAR can function as a key which fits into and binds a ligand when the ligand is a larger protein molecule. In this invention, a ligand is a substance that specifically interacts with or binds to a TSAR and includes, but is not limited to, an organic chemical group, an ion, a metal or non-metal inorganic ion, a glycoprotein, a protein, a polypeptide, a peptide, a nucleic acid, a carbohydrate or carbohydrate polymer, a lipid, a fatty acid, a viral particle, a membrane vesicle, a cell wall component, a synthetic organic compound, a bioorganic compound and an inorganic compound or any portion of any of the above.

The present invention further provides novel TSAR reagents as well as compositions comprising a binding domain of a TSAR or a portion thereof which has specificity for a ligand of choice and methods for using TSARs and compositions comprising a binding domain of a TSAR or a portion thereof which retains the binding specificity of the TSAR binding domain.

Solely, for ease of explanation, the description of the invention may be divided into the following sections: (A) methods to identify TSARs including (i) construction and (ii) screening of libraries; (B) TSARs and compositions comprising a binding domain of a TSAR or portion thereof; and (C) applications of or uses for TSARs and TSAR compositions. The description of the methods for constructing TSAR libraries may be subdivided into: (a) synthesis and assembly of synthetic oligonucleotides; (b) insertion of the synthetic oligonucleotides into an appropriate expression vector; and (c) expression of the library of vectors. Methods for constructing linear, bimolecular and rigid libraries are described.

5.1. METHODS TO IDENTIFY TSARs: CONSTRUCTION OF LIBRARIES

In its most general embodiment, the process of the present method for rapidly and efficiently identifying novel binding reagents termed TSARs comprises two steps: (a) constructing a library of vectors expressing inserted synthetic oligonucleotide sequences encoding a plurality of proteins, polypeptides and/or peptides as fusion proteins, for example, attached to an accessible surface structural protein of a vector; and (b) screening the expressed library or plurality of recombinant vectors to isolate those members producing proteins, polypeptides and/or peptides that bind to a ligand of interest. The nucleic acid sequence of the inserted synthetic oligonucleotides of the isolated vector is determined and the amino acid sequence encoded is deduced to identify a TSAR binding domain that binds ligand of choice.

It is, of course, understood that once a library is constructed according to the present invention, said library can be screened any number of times with a number of different ligands of choice to identify TSARs binding the given ligand. Such screening methods are also encompassed within the present invention.

5.1.1. SYNTHESIS AND ASSEMBLY OF OLIGONUCLEOTIDES

In order to prepare a library of vectors expressing a plurality of protein, polypeptide and/or peptide TSARs according to the present invention, single stranded sets of nucleotides are synthesized and assembled in vitro according to the following scheme.

The synthesized nucleotide sequences are designed to have variant or unpredicted and invariant nucleotide positions. Pairs of variant nucleotides in which one individual member is represented by $5'(NNB)_n3'$ and the other member is represented by $3'(NNV)_m5'$ where N is A, C, G or T; B is G, T or C; V is G, A or C; n is an integer, such that $10 \leq n \leq 100$, and m is an integer, such that $10 \leq m \leq 100$, are synthesized for assembly into synthetic oligonucleotides. As assembled, according to the present invention, there are at least n+m variant codons in each inserted synthesized double stranded oligonucleotide sequence (FIG. 1A).

As would be understood by those of skill in the art, the variant nucleotide positions have the potential to encode all 20 naturally occurring amino acids and, when assembled as taught by the present method, encode only one stop codon, i.e., TAG. The sequence of amino acids encoded by the variant nucleotides of the present invention is unpredictable and substantially random in sequence. The terms "unpredicted", "unpredictable" and "substantially random" are used interchangeably in the present application with respect to the amino acids encoded and are intended to mean that at any given position within the binding domain of the TSARs encoded by the variant nucleotides which of the 20 naturally occurring amino acids will occur cannot be predicted.

The variant nucleotides, according to the present scheme, encode all twenty naturally occurring amino acids by use of 48 different codons. Although this affords somewhat less variability than found in nature, in which 64 different codons are used, the present scheme for designing the variant nucleotides advantageously provides greater variability than in conventional schemes such as those which use nucleotides of the formula NNK, in which K is G or T (see Dower, W091/19818, supra) or of the formula NNS, in which S is G or C (see Devlin, W091/18980), in which only 32 codons are employed.

Moreover, as discussed in Section 5.1.3 (infra), when the synthesized oligonucleotides are inserted into an expression vector, the single stop codon TAG can be suppressed by expressing the library of vectors in a mutant host, such as *E. coli* supE, [see generally, Sambrook, Fritsh and Maniatis, Molecular Cloning: A Laboratory Manual, 2d. ed. Cold Spring Harbor Laboratory Press, pp. 2.55, 2.57–0.59, 4.13–4.15 1989 (herein Maniatis)].

As would be understood by those of skill in the art, use of variant codons of the formula NNK or NNS would, like the presently employed NNB formula, encode only one type of stop codon, i.e., TAG. If the use of suppressors, such as SupE, were 100% efficient to suppress the single stop codon, there would be no difference or advantage in using the present NNB scheme over those schemes used by conventional methods.

On the other hand, if suppression were not 100% efficient or if there were no suppressions available for a particular vector/host system, then the presently taught NNB would be more advantageous than either the NNK or NNS systems because since it utilizes 47 rather than 31 amino acid encoding codons, the chance of having a stop codon in a sequence of a particular length of nucleotides is less. To illustrate, the probability of having a stop codon in a sequence of 36 codons using the presently taught NNB scheme is $[1-(47/48)^{36}]$ or about 53% whereas, using the NNK or NNS scheme, such probability would be $[1-(31/32)^{36}]$ or 68%. The NNN scheme could be used, but there would be a terrific increase in the number of recombinants with stop codons: e.g., $[1 -(61/64)^{36}]=0.82$ or 82%. Thus, use of the presently taught NNB scheme is particularly advantageous in minimizing the number of recombinants with internal stop codons. This difference becomes magnified when longer TSAR peptides are expressed. This becomes especially important where the size of the inserted oligonucleotides is large, e.g., greater than about 20 codons. For example, using the presently taught method, in an oligonucleotide of 100 codons, the probability of not having a stop codon, i.e. of having an open reading frame, would be $(47/48)^{100}$ or about 12% whereas using the NNS or NNK method, such probability would be $(31/32)^{100}$ or about only 4%.

Indeed, as explained more fully in Section 6.3 (infra), analysis of a large number of inserted synthesized oligonucleotides according to the present invention expressed by an M13 vector derivative in a supE *E. coli* mutant demonstrated that very few TAG stop codons were observed in the binding domain sequences expressed by the TSAR vectors. Thus, it appears that use of supE in this system is not very efficient and hence use of the present NNB scheme is particularly useful.

The NNB scheme offers additional flexibility when the TSAR peptides are expressed in hosts that lack suppressor tRNA genes. That is, the NNB scheme would not be restricted only to host organisms that have been subject to intense molecular genetic manipulation and thus offers greater flexibility in host selection.

One could avoid stop codons altogether by use of codon triplets, but then one would need to know codon preference ideally for each host. NNB offers greater flexibility in host range.

The invariant nucleotides are positioned at particular sites in the nucleotide sequences to aid in assembly and cloning of the synthesized oligonucleotides. At the 5' termini of the sets of variant nucleotides, the invariant nucleotides encode for efficient restriction enzyme cleavage sites. The invariant nucleotides at the 5' termini are chosen to encode pairs of sites for cleavage by restriction enzymes (1) which can function in the same buffer conditions; (2) are commercially available at high specific activity; (3) are not complementary to each other to prevent self-ligation of the synthesized double stranded oligonucleotides; and (4) which require either 6 or 8 nucleotides for a cleavage recognition site in order to lower the frequency of cleaving within the inserted double stranded synthesized oligonucleotide sequences. According to particular embodiments of peptide libraries exemplified in Section 6 (infra), the selected restriction site pairs are selected from Xho I and Xba I, and Sal I and Sp I. Other examples of useful restriction enzyme sites include, but are not limited to: Nco I, Nsi I, Pal I, Not I, Sfi I, Pme I, etc. Restriction sites at the 5' termini invariant positions function to promote proper orientation and efficient production of recombinant molecule formation during ligation when the oligonucleotides are inserted into an appropriate expression vector.

According to an alternate embodiment of the present invention, the variant nucleotides are synthesized using one or more methylated dNTP's and the 5' termini invariant nucleotides, encoding restriction sites for efficient cleavage, are synthesized using non-methylated dNTPs. This embodiment provides for efficient cleavage of long length synthesized oligonucleotides at the termini for insertion into an appropriate vector, while avoiding cleavage in the variant nucleotide sequences.

The 3' termini invariant nucleotide positions are complementary pairs of 6, 9 or 12 nucleotides to aid in annealing two synthesized single stranded sets of nucleotides together and conversion to double-stranded DNA, designated herein synthesized double stranded oligonucleotides.

In particular embodiments of peptide libraries exemplified in Section 6 (era), the 3' termini invariant nucleotides are selected from $^5$'GCGGTG$^3$' and $^3$'CGCCAC$^5$', and $^5$'CCAGGT$^3$' and $^3$'GGTCCA$^5$', which also encode either a particular amino acid, glycine, or dipeptide proline-glycine, which provides the flexibility of either a swivel or hinge type configuration to the expressed proteins, polypeptides and/or peptides, respectively.

In another embodiment, the complementary 3' termini also encode an amino acid sequence that provides a short charge cluster (for example, KKKK, DDDD or KDKD), or a sharp turn (for example, NPXY, YXRF where X is any amino acid). In another alternative embodiment, the complementary 3' termini also encode a short amino acid sequence that provides a peptide known to have a desirable binding or other biological activity. Specific examples include complementary pairs of sequences encoding peptides including but not limited to RGD, HAV, HPQ⊖ where ⊖ is a non-polar amino acid.

FIG. 1A generally illustrates the assembly process according to the method of the present invention. The oligonucleotide sequences are thus assembled by a process comprising: synthesis of pairs of single stranded nucleotides having a formula represented.

(a) 5'→3' Restriction site-(NNB)$_n$-Complementary site; and (b) 3'→5' Complementary site-(NNV)$_m$-Restriction site, where n is an integer, such that $10 \leq n \leq 100$ and m is an integer, such that $10 \leq m \leq 100$. More particularly, the single stranded nucleotides are represented as: pairs of nucleotide sequences of a first formula 5' X (NNB)$_n$ J Z 3' and a second nucleotide sequence of the formula

3'Z'O U (NNV)$_m$ Y 5' where X and Y are restriction enzyme recognition sites, such that X ≠ Y;

N is A, C, G or T;

B is G, T or C;

V is G, A or C;

n is an integer, such that $10 \leq n \leq 100$;

m is an integer, such that $10 \leq m \leq 100$;

Z and Z' are each a sequence of 6, 9 or 12 nucleotides, such that

Z and Z' are complementary to each other; and

J is A, C, G, T or nothing;

O is A, C, G, T or nothing; and

U is G, A, C or nothing; provided, however, if any one of J, O or U is nothing then J, O and U are all nothing.

Any method for synthesis of the single stranded sets of nucleotides is suitable, including such as use of an automatic nucleotide synthesizer. The synthesizer can be programmed so that the nucleotides can be incorporated, either in equimolar or non-equimolar ratios amounts at the variant positions, i.e., N, B, V, J, O or U. The nucleotide sequences of the desired length are purified, for example, by HPLC.

Pairs of the purified, single stranded nucleotides of the desired length are reacted together in appropriate buffers through repetitive cycles of annealing and DNA synthesis using an appropriate DNA polymerase, such as Taq, Vent™ or Bst DNA polymerase, and appropriate temperature cycling. Klenow fragment of *E. coli* DNA polymerase could be used but, as would be understood by those of skill in the art, such polymerase would need to be replenished at each cycle and thus is less preferred. The double stranded DNA reaction products, now greater than m+n in length, are isolated, for example, by phenol/chloroform extraction and precipitation with ethanol.

After resuspension in buffer, the double stranded synthetic oligonucleotides are cleaved with appropriate restriction enzymes to yield a plurality of synthesized oligonucleotides. The double-stranded synthesized oligonucleotides should be selected for those of the appropriate size by means of high resolution polyacrylamide gel electrophoresis, or NuSieve/MetaMorph (FMC Corp., Rockland, Mass.) agarose gel electrophoresis, or the like. Size selection of the oligonucleotides substantially eliminates abortive assembly products of inappropriate size and incomplete digestion products.

The scheme for synthesis and assembly of the unpredictable oligonucleotides used to construct the libraries of the present invention incorporates m+n variant, unpredicted nucleotide sequences of the formula (NNB)$_{n+m}$ where B is G, T or C and n and m are each an integer, such that $20 \leq n+m \leq 200$ into the synthesized double stranded oligonucleotides. Such a scheme provides a number of important advantages not available with conventional libraries. As assembled, the present synthesized oligonucleotides encode all twenty naturally occurring amino acids by use of 48 different amino acid encoding codons. Although this uses somewhat less variability than that found in nature where 64 different codons are used, the present scheme advantageously provides greater variability than other conventional schemes. For example, conventional schemes in which the variant nucleotides have the formula NNK, where K is G or T, or NNS, where S is C or G, use only 32 different amino acid encoding codons. The use of a larger number of amino acid encoding codons may make the present libraries less susceptible to codon preferences of the host when the libraries are expressed. Although both the present scheme and conventional schemes retain only 1 stop codon, use of NNB as presently taught advantageously provides synthesized oligonucleotides in which the probability of a stop codon is decreased compared to conventional NNS or NNK schemes.

Additionally, the present scheme avoids the use of synthesized oligonucleotides rich in GC nucleotides such as often found in libraries using an NNS formula for variant codons. As is well known to those of skill in the art, nucleotide sequences rich in GC residues are difficult to assemble properly and to sequence.

The present scheme for assembling the oligonucleotides using sets of nucleotides having variant and invariant regions comprising two different single stranded nucleotide sequences depicted:

(a) 5'→3' Restriction site-(NNB)$_n$-Complementary Site; and (b) 3'→5' Complementary Site-(NNV)$_m$-Restriction Site, advantageously provides for efficient annealing of the two single stranded sets of nucleotides. This assembly method works so effectively that relatively little DNA must be initially synthesized and the synthesized nucleotides can efficiently be converted to double stranded oligonucleotides using an appropriate polymerase, such as Taq DNA polymerase, in repetitive cycles of annealing and extending.

Perhaps most significantly, the present scheme for synthesis and assembly of the oligonucleotides provides sequences of oligonucleotides encoding unpredicted amino acid sequences which are larger in size than any prior conventional libraries. As constructed according to the present invention, the present synthesized double stranded oligonucleotides comprise at least about 77–631 nucleotides in length encoding the restriction enzyme sites, the complementary site and about 20–200 unpredicted amino acids in the TSAR binding domain. According to a preferred embodiment, n and m are greater than or equal to 10 and less than or equal to 50. Thus, the synthesized double stranded oligonucleotides comprise at least 77–331 nucleotides and encode about 20–100 unpredicted amino acids in the TSAR binding domain. In the specifically exemplified examples, the synthesized oligonucleotides encode respectively, 27 and 42 amino acids in the TSAR binding domain.

The conventional teaching in the art is that the length of inserted oligonucleotides should be kept small encoding preferably less than 15 and most preferably about 6–8 amino acids. Completely contrary, the present inventors have found that not only can libraries encoding greater than about 20 amino acids be constructed, but that such libraries can be advantageously screened to identify TSARs or proteins, polypeptides and/or proteins having binding specificity for a variety of ligands.

Among those interested in using computer modeling to identify binding molecules for drug development, the conventional wisdom has been that the peptides used as heads for developing non-peptide mimetics should be kept to a maximum of about 6–8 amino acids. Computer modeling of larger peptides has been deemed impractical or non-informative. Hence, the conventional wisdom has been that screening libraries of short peptide sequences is more productive. In complete contrast, the present invention, which provides methods to efficiently generate and screen libraries of much longer peptides to identify binding peptides, has quite successfully elucidated smaller motifs (i.e., 6–8 amino acids) that can be used later for drug development using such computer modeling techniques. Additionally, we believe that the longer peptides identified by the methods of the present invention afford a whole new vista of drug candidates.

As demonstrated in the examples in Section 7 (infra), the long length of the present inserted oligonucleotides affords the ability to identify TSARs in which a short sequence of amino acids is common or shared by a number of proteins/peptides binding a given ligand, i.e., TSARs having shared binding motifs, as well as to identify TSARs which do not have any shared sequences with other peptides (non-motif) having binding specificity for the same ligand. Thus, the present library provides for the ability to identify TSARs having affinity for a ligand, with either a simple or complex binding site.

In a particular application, i.e., the identification of a TSAR having binding specificity for an epitope of an antibody, the present libraries having large inserted oligonucleotide sequences provide the opportunity to identify or map epitopes which encompass not only a few contiguous amino acid residues, i.e., simple epitopes, but also those which encompass discontinuous amino acids, i.e., complex epitopes.

Additionally, the large size of the inserted synthesized oligonucleotides of the present libraries may provide the opportunity for the development of secondary and/or tertiary structure development in the potential binding proteins/peptides and in sequences flanking the actual binding portion of the binding domain of the peptide. Such complex structural developments are not feasible when only small length oligonucleotides are used.

Finally, as has been overlooked by the conventional wisdom, longer length peptide libraries provide a greatly enhanced complexity over shorter length peptide libraries which would not have been obvious to one of skill in the art. This greatly enhanced complexity is associated with the concept of sliding windows which must be counted inclusively, i.e., number of windows=[length of sequence] −[window size]+1. This concept can be illustrated by comparison of two libraries, as follows. Assume that a binding site to a ligand requires 5 contiguous amino acid residues (5 mer).

In two libraries composed of equal numbers of recombinants, one library expressing 5 mers and the second library, constructed according to the present invention, expressing the second library will be 26 times "richer" in binding sites relative to the first library. In other words, one would have to construct 26 5 mer libraries to achieve the same number of possible 5 mers as represented in a single 30 mer library according to the present invention. Of course, this difference increases as the length of the expressed peptides become longer.

Figure 1D:
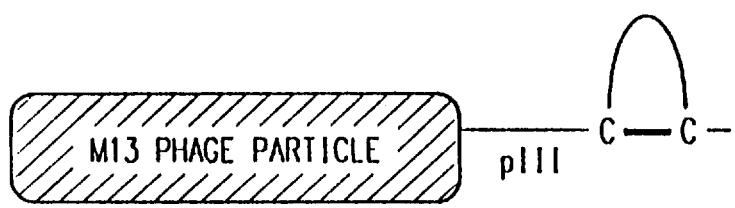
Figure 1E:
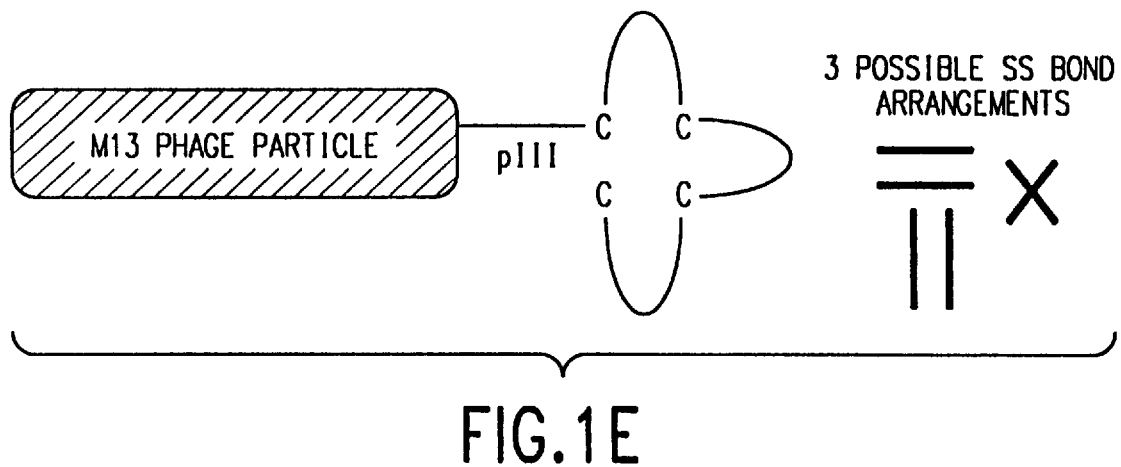
Figure 1F:
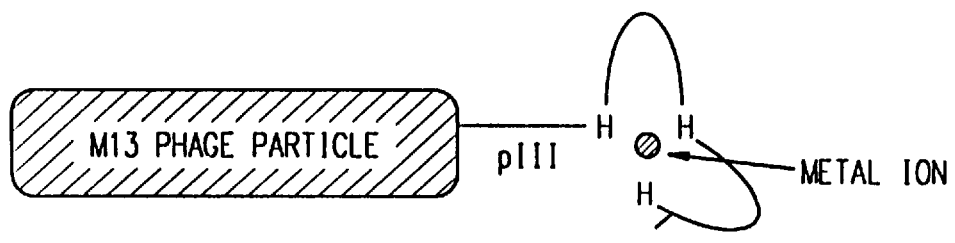

According to an alternative embodiment of the invention, illustrated in FIG. 1D–F, a library is constructed which expresses a plurality of TSAR proteins, polypeptides and/or peptides having some degree of conformational rigidity in their structure (semi-rigid peptide libraries). In a semi-rigid peptide library, the plurality of synthetic oligonucleotides express peptides that are able to adopt only one or a small number of different conformations that are constrained by the positioning of codons encoding certain amino acids in or flanking the synthesized variant or unpredicted oligonucleotides. Unlike the libraries constructed as described above in which the plurality of proteins expressed potentially adopt thousands of short-lived different conformations, in a semi-rigid peptide library, the plurality of proteins expressed can adopt only a single or a small number of conformations.

Four different methods can be used to engineer the libraries of the present invention so that the peptides are rigid. In the first method, the synthesized oligonucleotides are designed so that the expressed peptides have a pair of invariant cysteine residues positioned in, or flanking, the unpredicted or variant residues. When the library is expressed in an oxidizing environment, the cysteine residues should be in the oxidized state, most likely cross-linked by disulfide bonds to form cystines. Thus, the peptides would form rigid loops. The nucleotides encoding the cysteine residues should be placed from 6 to 27 amino acids apart within the variant nucleotide sequences.

The actual positions of the invariant residues can be modeled on the arrangement observed in a linear peptide library formed according to the present invention. For example, random isolation and sequencing of a number of TSAR peptides from the TSAR-9 or TSAR-12 libraries illustrated in Section 6. 1.1 (infra) has yielded TSARs in which two or four cysteines are encoded by the inserted synthesized oligonucleotides. See, e.g., peptides such as TSAR-9-6, 9, 9', 12', 13' (SEQ ID NOs. 1–5) Which can be encoded by oligonucleotides represented by the following general formulas:

(1) $X(NNB)_6(TGC)(NNB)_{11}Z(NNB)_{14}(TGC)(NNB)_3Y$ (TSARs-9-6 & 9);

(2) $X(NNB)_1(TGC)(NNB)_{10}(TGC)_2(NNB)_4Z(NNB)_8(TGC)(NNB)_9Y$ (TSAR-9-9');

(3) $X(NNB)_{16}(TGC)(NNB)_1Z(NNB)_{16}(TGC)(NNB)_1, Y$ (TSAR-9-12');

(4) $X(NNB)_{11}(TGC)(NNB)_6Z(NNB)_7(TGC)$ $(NNB)_{10}Y$ (TSAR-9-13') containing appropriate TAG codons coding for cysteine residues. The positions of the cysteines are well tolerated as these phage are stable and infectious.

In the second method, a double stranded oligonucleotide sequence providing a cloverleaf structure (see FIG. 1E) can be represented, for example, by the formula: $X(TGC)_1(NNB)_{10}(TGC)_1(NNB)_6Z(NNB)_2(TGC)_{14}(NNB)_{14}(TGC)_1Y$. When these peptides are expressed by the appropriate vectors, the cysteine residues may adopt three different disulfide bond arrangements, thereby generating three different patterns of "cloverleafs". The plurality of proteins, polypeptides and/or peptides expressed by this type of rigid library should form many different ligand binding pockets from which to select the best fit. It should be noted that when a semi-rigid library of the first or second type above is expressed in a viral vector in an oxidizing environment, there will likely be a selection against odd numbers of cysteines occurring within the unpredicted or random peptide regions expressed because one unpaired cysteine residue will likely cross-link the viral vectors and make them non-infectious. This potential problem might be minimized by the use of a reducing agent such as DTT or β-mercaptoethanol.

In the third method, the synthesized nucleotides are designed and assembled so that the plurality of proteins expressed have both invariant cysteine and histidine residues positioned within the variant nucleotide sequences (see FIG. 1F). The positions of the invariant residues can be modeled after the arrangement of cysteine and histidine residues seen in zinc-fingers proteins (i.e., —$CX_{2-4}CX_{,12}HX_{3-4}H$—, where X is any amino acid).

In the fourth method, (see FIG. 1F), the plurality of proteins are designed to have invariant histidine residues positioned within the variant nucleotide sequences. The actual positions of the invariant residues can be modeled after the arrangement observed in zinc-binding TSARs identified according to the present invention, such as zinc-binding TSARs illustrated, for example, in Section 7.3 (e.g., Zn1-B7, -B6, -A7, -A12; SEQ ID NOs. 36, 37, 41, 51), as these TSARs when expressed in phage vectors yield phage which are stable and infectious. To illustrate, the exemplary histidine containing TSARs can be represented by the following general formulas:

(1) $X(NNB)_4(CAC)(NNB)_4(CAC)(NNB)_8Z(NNB)_6(CAC)(NNB)8(CAC)_2(NNB)Y$ (TSAR-Zn1-B7);

(2) $X(NNB)_6(CAC)(NNB)_9(CAC)(NNB)Z(CAC)(NNB)_4(CAC)_2(NNB)_6(CAC)(NNB)(CAC)(NNB)_2Y$ (TSAR-Zn 1-B6);

(3) $X(NNB)I\ (CAC)(NNB)I\ I(CAC),\ (NNB)(CAC)(NNB)_2Z(NNB)_6(CAC)\ (NNB)_5(CAC)_2(NNB)_4Y$ (TSAR Zn1-A7); and (4) $X(CAC)(NNB)_2(CAC)(NNB)_9(CAC)(NNB)_2(CAC)(NNB)Z(CAC)\ (NNB)_6(CAC)(NNB)_4(CAC)(NNB)(CAC)(NNB)_3Y$ (TSAR Zn1-A12), where CAC represents the codon for histidine.

To maintain the rigid cloverleaf conformation of this plurality of proteins, the TSAR proteins are expressed and harvested in the presence of 1–1000 μM zinc chloride. The expressed proteins could also be saturated with other divalent metal cations, such as $Cu^{2+}$ and $Ni^{2+}$. The members of this type of rigid library may have advantageous chemical reactivity, since metal ions are often within the catalytic sites of enzymes.

An additional feature of these rigid libraries is the potential to control the binding properties of isolates by reversibly destroying or altering the rigidity of the peptide. For example, it should be possible to elute a TSAR bound to a particular ligand in a gentle manner with reducing agents (i.e., DTT, β-mercaptoethanol) or divalent cation chelators (i.e., EDTA, EGTA). Such reagents can be used, for example, to elute a TSAR library expressed on phage vectors from target ligands. EDTA or EGTA, at low concentrations does not appear to disrupt phage integrity or infectivity.

Once the phage have been recovered and it is deemed necessary to remove thiols from the solution, the reduced cysteine residues can be alkylated with iodoacetamide. This treatment prevents renewed disulfide bond formation and only diminishes phage infectivity 10–100 fold, which is tolerable since phage cultures usually attain titers of $10^{12}$ plaque forming units per milliliter. Alternatively, the elution reagents can be removed by dialysis (i.e., dialysis bag, Centricon/Amicon microconcentrators).

5.1.2. INSERTION OF SYNTHETIC OLIGONUCLEOTIDES INTO AN APPROPRIATE VECTOR

The plurality of oligonucleotides of appropriate size prepared as described above is inserted into an appropriate vector which when inserted into a suitable host expresses the plurality of proteins, polypeptides and/or proteins as heterofunctional fusion proteins with an expressed component of the vector which are screened to identify TSARs having affinity for a ligand of choice. According to an optional embodiment, the plurality of proteins, polypeptides and/or peptides further comprise a linking domain between the binding and effector domains. In a preferred mode of this embodiment, the linker domain is expressed as a fusion protein with the effector domain of the vector into which the plurality of oligonucleotides are inserted.

5.1.2.1. LINEAR LIBRARIES

The skilled artisan will recognize that to achieve transcription and translation of the plurality of oligonucleotides, the synthetic oligonucleotides must be placed under the control of a promoter compatible with the chosen vector-host system. A promoter is a region of DNA at which RNA polymerase attaches and initiates transcription. The promoter selected may be any one that has been synthesized or isolated that is functional in the vector-host system. For example, E. coli, a commonly used host system, has numerous promoters such as the lac or trp promoter or the promoters of its bacteriophages or its plasmids. Also synthetic or recombinantly produced promoters such as the $P_{TAC}$ promoter may be used to direct high level expression of the gene segments adjacent to it.

Signals are also necessary in order to attain efficient translation of the inserted oligonucleotides. For example in E. coli mRNA, a ribosome binding site includes the translational start codon AUG or GUG in addition to other sequences complementary to the bases of the 3' end of 16S ribosomal RNA. Several of these latter sequences such as the Shine/Dalgarno (S/D) sequence have been identified in E. coli and other suitable host cell types. Any S/D-ATG sequence which is compatible with the host cell system can be employed. These S/D-ATG sequences include, but are not limited to, the S/D-ATG sequences of the cro gene or N gene of bacteriophage lambda, the tryptophan E, D, C, B or A genes, a synthetic S/D sequence or other S/D-ATG sequences known and used in the art. Thus, regulatory elements control the expression of the polypeptide or proteins to allow directed synthesis of the reagents in cells and to prevent constitutive synthesis of products which might be toxic to host cells and thereby interfere with cell growth.

Any of a variety of vectors can be used according to the methods of the invention, including, but not limited to bacteriophage vectors such as ØX174, λ, M13 and its derivatives, f1, fd, Pf1, etc., phagemid vectors, plasmid vectors, insect viruses, such as baculovirus vectors, mammalian cell vectors, including such as parvovirus vectors, adenovirus vectors, vaccinia virus vectors, retrovirus vectors, etc., yeast vectors such as Ty1, killer particles, etc.

An appropriate vector contains or is engineered to contain a gene encoding an effector domain of a TSAR to aid expression and/or detection of the TSAR. The effector domain gene contains or is engineered to contain multiple cloning sites. At least two different restriction enzyme sites within such gene, comprising a polylinker, are preferred. The vector DNA is cleaved within the polylinker using two different restriction enzymes to generate termini complementary to the termini of the double stranded synthesized oligonucleotides assembled as described above. Preferably the vector termini after cleavage have or are modified, using DNA polymerase, to have non-compatible sticky ends that do not self-ligate, thus favoring insertion of the double-stranded synthesized oligonucleotides and hence formation of recombinants expressing the TSAR fusion proteins, polypeptides and/or peptides. The double stranded synthesized oligonucleotides are ligated to the appropriately cleaved vector using DNA ligase.

The present inventors have surprisingly discovered that it is particularly useful to include a "stuffer fragment" within the polylinker region of the vector when the vector (e.g. phage or plasmid) is intended to express the TSAR as a heterofunctional fusion protein that is expressed on the surface of the vector. As used in the present application, a "stuffer fragment" is intended to encompass a relatively short, i.e., about 24–45 nucleotides, known DNA sequence flanked by at least 2 restriction enzyme sites, useful for cloning, said DNA sequences coding for a binding site recognized by a known ligand, such as an epitope of a known monoclonal antibody. The restriction enzyme sites at the termini of the stuffer fragment are useful for insertion of the synthesized double stranded oligonucleotides, resulting in deletion of the stuffer fragment.

Because of the physical linkage between the expressed heterologous fusion protein and the phage or plasmid vector containing the stuffer fragment and because the stuffer fragment comprises a known DNA sequence encoding a protein that is easily detected, immunologically active (i.e., an immunological marker), the presence or absence of the stuffer fragment can be easily detected either at the nucleotide level, by DNA sequencing, PCR or hybridization, or at the amino acid level, e.g., using an immunological assay. Such determination allows rapid discrimination between recombinant (TSAR expressing) vectors generated by insertion of the synthesized double stranded oligonucleotides and non-recombinant vectors.

In one advantageous aspect, the use of a stuffer fragment avoids a problem often encountered with the use of a conventional polylinker in the vector—i.e., the restriction sites of the polylinker are too close so that adjacent sites cannot be cleaved independently and used at the same time.

According to a preferred embodiment of the invention, the stuffer fragment comprises the DNA fragment encoding the epitope of the human c-myc protein recognized by the murine monoclonal antibody 9E10 (Evan et al., 1985, Mol. Cell. Biol. 5: 3610–3616) with a short flanking sequence of amino acids at the 5' and 3' termini which serve as restriction enzyme sites so that the synthesized double stranded oligonucleotides can be inserted using the restriction sites. Thus, the preferred stuffer fragment comprises the DNA encoding the epitope of the c-myc protein recognized by the 9E10 monoclonal antibody having the amino acid sequence EQK-LISEEDLN (SEQ ID NO 6) plus a small number of flanking amino acids at the $NH_2$ and COOH termini which provide appropriate restriction enzyme sites for removal of the stuffer fragment and insertion of the synthesized double stranded oligonucleotides.

As has been surprisingly discovered by the present inventors, use of a "stuffer" fragment has provided TSAR libraries in which the number of non-recombinants found is surprisingly small. For example, in the TSAR-9 and TSAR-12 libraries exemplified in Section 6, infra, in which the stuffer fragment comprises the epitope of the c-myc protein, less than about 5% of the TSAR expressing vectors were found to be non-recombinants. This is particularly advantageous as it provides a larger number of candidates from which a desired TSAR binding protein can be identified.

Although not intending to be limited to any particular mechanism or theory to explain the advantageously low number of non-recombinants obtained when a stuffer fragment is incorporated into a vector employed in the methods of the invention, applicants offer the following theoretical explanation.

It is possible that insertion of a stuffer fragment may tolerably and comparably enfeeble the non-recombinant vectors so that there is a minimal difference in the growth of non-recombinant and recombinant vectors. Such minimization of growth differences thus prevents the non-recombinant vectors from overgrowing the recombinants. Further, it is postulated that such advantageous minimization may be particularly useful to yield an efficient production of recombinant vectors especially when the double stranded synthesized oligonucleotides are of large size as in the present TSAR libraries.

In another aspect, the stuffer fragment provides an efficient means to remove any non-recombinant vectors to enhance or enrich the population of TSAR expressing vectors, if necessary. Because the stuffer fragment would be expressed e.g., as an immunologically active surface protein on the surface of non-recombinant vectors, it provides an accessible target for binding e.g., to an immobilized antibody. The non-recombinants thus could be easily removed from a library for example by serial passage over a column having the antibody immobilized thereon to enrich the population of recombinant TSAR-expressing vectors in the library.

In a preferred embodiment the vector is or is derived from a filamentous bacteriophage, including but not limited to M13, f1, fd, Pf1, etc. vector encoding a phage structural protein, preferably a phage coat protein, such as pIII, pVIII, etc. In a more preferred embodiment, the filamentous phage is an M13-derived phage vector such as m655, m663 and m666 described in Fowlkes et al., 1992, BioTechniques, 13: 422–427 (Fowlkes) which encodes the structural coat protein pII (SEQ ID NO 7).

The phage vector is chosen to contain or is constructed to contain a cloning site located in the 5' region of a gene encoding a bacteriophage structural protein so that the plurality of synthesized double stranded oligonucleotides inserted are expressed as fusion proteins on the surface of the bacteriophage. This advantageously provides not only a plurality of accessible expressed proteins/peptides but also provides a physical link between the proteins/peptides and the inserted oligonucleotides to provide for easy screening and sequencing of the identified TSARs. Alternatively, the vector is chosen to contain or is constructed to contain a cloning site near the 3' region of a gene encoding structural protein so that the plurality of expressed proteins constitute C-terminal fusion proteins.

According to a preferred embodiment, the structural bacteriophage protein is pIII. The m663 vector described by Fowlkes, and illustrated in FIG. 4, containing the pIII gene having a c-myc-epitope comprising the "stuffer fragment" introduced at the N-terminal end, flanked by Xho I and Xba I restriction sites was used in examples exemplified in Section 6 (infra). The library is constructed by cloning the plurality of synthesized oligonucleotides into a cloning site near the N-terminus of the mature coat protein of the appropriate vector, preferably the pill protein, so that the oligonucleotides are expressed as coat protein-fusion proteins.

According to an alternative embodiment, the plurality of oligonucleotides is inserted into a phagemid vector. Phagemids are utilized in combination with a defective helper phage to supply missing viral proteins and replicative functions. Helper phage useful for propagation of M13 derived phagemids as viral particles include but are not limited to M13 phage K07, R408, VCS, etc. Suitable phagemid vectors are described in the specific examples in Section 8 (infra). Generally, according to a preferred mode of this embodiment (see, FIG. 5) the appropriate phagemid vector was constructed by engineering the Bluescript II SK+ vector (GenBank #52328) (Alting-Mees et al., 1989, Nucl. Acid Res. 17(22): p 9494); to contain (1) a truncated portion of the M13 pIII gene, i.e., nucleotides encoding amino acid residues 198–406 of the mature pIII, (2) the PelB signal leading with an upstream ribosome binding site and a short polylinker of Pst I, Xho I, Hind III, and Xba I restriction sites, in which the Xho I and Xba I sites are positioned so the synthesized double stranded oligonucleotides could be cloned and expressed in the same reading frame as the m663 phage vector; and (3) the linker sequence encoding gly-gly-gly-gly-ser between the polylinker and the pIII gene.

According to an alternative embodiment, the synthesized oligonucleotides are inserted into a plasmid vector. An illustrative suitable plasmid vector for expressing the TSAR libraries is a derivative of plasmid p340-1 (ATCC No. 40516) illustrated in FIG. 16.

In order to obtain the appropriate p340-1 derivative suitable as an expression vector, the Nco I-Bam HI fragment is removed from p340-1 plasmid and replaced by a double stranded sequence having Xho I and Xba I restriction sites in the correct reading frame. In practice, p340-1is cleaved using restriction enzymes at the BglII and Xba I sites and annealed with two oligonucleotides:
(1) 5'-CATGGCTCGAGGCTGAGTTCTAGA-3' (SEQ ID NO 8) and (2) 5'-GATCTCTAGAACTCAGCCTCGAGC-3' (SEQ ID NO 9) having Nco I and Bam HI sticky ends. After ligation and transformation of E. coli, recombinants containing the desired plasmid designated p340-1D are selected based on the inserted SEQ ID NOs. 8 and 9 and verified by sequencing. Like the parent p340-1, the desired p340-1D does not produce functional β-galactosidase because this gene is out of frame. Thus, when the synthesized double stranded oligonucleotides are inserted, using the Xho I and Xba I restriction sites, into the p340-1D vector the coding frame is restored and the TSAR binding domain is expressed as a fusion protein with the β-galactosidase. When exposed to IPTG, the vectors expressing the TSAR library would produce identifiable blue colonies.

Another illustrative plasmid vector useful to express a TSAR library according to the present invention is a plasmid derivative of plasmid pTrc99A designated plasmid pLamB which is constructed to contain the LamB protein gene of E. coli having a cloning site so that the plurality of oligonucleotides inserted are expressed as fusion proteins of the LamB protein.

The LamB protein is a trimeric, outer membrane protein of E. coli of about 47 k Daltons expressed at many thousand copies per cell. The subunit size is about 421 amino acids. The LamB gene has been sequenced (Clement and Hofnung, 1981, Cell 27: 507–514). Computer modeling of this protein has suggested that it contains potentially 16 transmembrane domains, with certain peptide loops exposed outside the cell and others facing the periplasm. In addition, a number of natural cDNA or gene fragments have been expressed on the surface of E. coli by insertion at amino acid residue 153 of LamB (Charbit et al., 1988, Gene 70: 181–189). Inserts encoding up to 60 amino acid residues in length have still allowed the LamB protein to remain functional.

Insertion of the present synthesized oligonucleotides into a plasmid containing a cloning site in the LamB gene should be useful for a number of reasons. First, recombinant bacteria expressing this plasmid would be like the useful phage vectors for expressing the TSAR libraries, in that each cell would have the unpredicted peptides expressed in an accessible way on the outside of the cell, and that each cell would harbor the DNA encoding the unpredicted peptide. This physical linkage between the peptide and its coding element would make the libraries amenable to a variety of screening schemes. Second, as the unpredicted peptides would be expressed in the middle of the LamB protein, they would be conformationally constrained within a loop anchored at its base by insertion into the outer E. coli membrane. This contrasts with having the unpredicted peptides at the N-terminus of the M13 pill molecule where they are more likely free to adopt many conformations. Third, as the transformation rates of E. coli are higher (i.e., >10×) with plasmids than with M13 phage DNA, it might be possible to generate larger TSAR libraries (i.e., more recombinants).

Plasmid pTrc99a described in Amann et al., 1988, Gene 69: 301–315, (Pharmacia, Piscataway, N.J.) which is ampicillin resistant, carries the gene (lacI$^Q$) for the lac repressor, and the inducible promoter known as P$_{tac}$ promoter and its transcription is induced by adding IPTG to a bacterial culture. Downstream of the promoter is a Shine-Dalgarno sequence, ATG initiating codon, restriction site polylinker, and a strong transcription terminator.

FIG. 6 (A–B) depicts the preparation of pLamB vector. To introduce the LamB gene into pTrc99a, the E. coli LamB gene was amplified by PCR. Oligonucleotides were designed that amplified the gene in two segments, from aa 1–153 and 152–421, and at the same time created Xho I and Xba I sites in between codons 153 and 154. The pTrc99a vector was cleaved with Nco I and Hind III and both fragments were introduced by simple ligation, yielding the vector designated pLamB. The pLamB vector contains the Xho I and Xba I sites positioned so that the c-myc stuffer fragment or the synthesized double stranded oligonucleotides could be cloned and expressed in the same reading frame as the m663 vector.

According to another alternate mode of this embodiment of the invention, the plurality of synthesized oligonucleotides can be expressed, in a modified pLamB plasmid, at the C-terminus of a truncated LamB gene. This can be easily accomplished by introducing a stop codon at the Xba I site of the LamB gene, to create a modified vector. Alternatively, the double stranded synthesized oligonucleotides assembled according to the present invention can be modified during synthesis to insert a stop codon between the last (NNV) and Y in the oligonucleotides. The LamB protein is truncated, and non-functional (i.e., no longer functioning in maltose uptake, or as a phage receptor), but since the protein is not essential, the cells remain viable. The TSAR-peptides expressed at the C-terminus are free to adopt a larger number of conformations than possible when expressed within the LamB protein.

5.1.2.2. BIMOLECULAR LIBRARIES

According to another embodiment of the invention, a library is constructed which expresses a plurality of proteins, polypeptides and/or peptides having a bimolecular conformation (bimolecular peptide libraries). Such libraries have a number of advantageous aspects. First, in the process of forming the bimolecular association a pocket is formed; this pocket may serve to create "locks" for "keys" i.e., various sized molecules. Second, by pairing off a particular variant, unpredicted peptide sequence with others in many combinations, a large number of pockets are generated from which to select the best fit. Third, combinational associations in a bimolecular library are a very effective means of increasing the "complexity" of the library. The complexity is increased by the square of the number of bimolecular pairs.

In order to prepare a bimolecular peptide library, oligonucleotides are synthesized and assembled according to the following scheme. The key feature of this scheme is the utilization of a pair of heterodimerization domains as a linker domain (see Section 5.3, infra, for a more detailed description of the linker domain) in an appropriate vector adjacent to the variant or unpredicted oligonucleotides encoding the expressed peptides. The heterodimerization domain is short, encoding less than about 31 amino acids, and does not readily form homodimers. Examples of heterodimerization domains include but are not limited to structures such as a helix or helical structures, found, e.g., in collagen, keratin, the yeast protein GCN4 helix-turn-helix motifs, leucine zipper motifs as well as c-fos and c-jun (see generally Kostelny et al., 1992, J. Immunol. 148: 1547–1553; O'Shea et al., 1992, Cell. 68: 699–708). Proteins containing helix-turn-helix motifs are reviewed in Pabo and Sauer; 1984, Ann. Rev. Biochem. 53: 293.

In 1985, Berg, 1986 Science 232: 485 noted that five classes of proteins involved in nucleic acid binding and gene regulation could form small, independently structured, metal-binding domains that were termed zinc-fingers. The five classes were 1) the small gag type nucleic acid binding proteins of retroviruses with-one copy of the sequence $Cys-X_2-Cys-X_4-His-X_4-Cys$ (SEQ ID NO 10).the adenovirus E1A gene products with $Cys-X_2-Cys-X_{13}-Cys-X_2-Cys$ (SEQ ID NO 11); 3) tRNA synthetases with $Cys-X_2-Cys-X_9-Cys-X_2-Cys$ (SEQ ID NO 12); 4) the large T antigens of SV40 and polyoma viruses of $Cys-X_2-Cys-X_{11-13}-His-X_2-His$ (SEQ ID NO 13); and 5) bacteriophage proteins with $Cys-X_3-His-X_5-Cys-X_2-Cys$, (SEQ ID NO 14) where X is any amino acid. These sequences are involved in metal binding domains. The "leucine zipper" is a periodic repetition of leucine residues at every seventh position over eight helical turns in the enhancer binding protein or EBP of rat liver nuclei (Landschultz et al., 1988, Science 240: 1759). Noting that the et helix within this region exhibits amphipathy wherein one side of the helix is composed of hydrophobic amino acids and the other helix side has charged side chains and uncharged polar side chains, the authors proposed that this structure had unusual helical stability and allowed interdigitation or "zippering" of helical protein domains, including both inter- and intra- protein domain interactions. More recently, Chakrabarrty et al., 1991, Nature 351: 586–588 have indicated that an a helical pattern is generated by an amino acid sequence $Leu-X-Leu-X_2-Leu-X_3$, etc. and not just every seventh position as indicated by Landschultz et al. In addition, a sequence having increased α helicity can be achieved using an amino acid sequence Glu-Ala-Ala-Ala-Arg-Ala-Ala-Glu-Ala-Ala-Ala-Arg (SEQ ID NO 15) (Merutka et al., 1991, Biochem. 30: 4245–4248). The scheme below is described in terms of the heterodimerization domains c-fos and c-jun, simply for the sake of ease of explanation. This is not intended to limit the scope of the embodiment to these examples. The above heterodimerization domains could be employed analogously in this embodiment of the invention.

After synthesis and assembly of double stranded synthetic oligonucleotide sequences as described above in Section 5.1. 1, the sequences are inserted into appropriate vectors. Two separate sublibraries are constructed: (1) one with the synthesized oligonucleotides positioned next to the nucleotide c-fos dimerization domain, i.e., amino acid residues 162–193 comprising amino acids TDTLQAETDQLED-KKSALQTEIANLLKEKEKL (SEQ ID NO 16); and (2) a second sublibrary with the synthesized oligonucleotides positioned next to the nucleotide sequence encoding the c-jun dimerization domain i.e., amino acid residues 286–317, comprising amino acids IARLEEKVK-TLKAQNSELASTANMLREQVAQL (SEQ ID NO 17) of the vectors. Conditions are determined to minimize the degree of homodimerization within each sublibrary. Conditions to minimize homodimerization include, for example, utilization of phagemid vectors, flanking the dimerization domains by a pair of cysteine residues, limited proteolysis, and/or altered pH conditions. The two sublibraries are then mixed together in a 1 to 1 proportion of viral particles and the mixture exposed to appropriate conditions to promote heterodimerizations. If each sublibrary has $10^8$ different members, then $10^{16}$ viral particles of each sublibrary can be mixed together to generate $10^{16}$ different bimolecular combinations. For example, ten liters of an overnight culture containing bacteria infected from phage (or bearing phagemids) from a sublibrary should yield $10^{16}$ particles which can be resuspended in a volume of <100 ml. This mixture of dimerized phage or phagemid particles constitutes the bimolecular peptide library.

Other types of the bimolecular libraries are constructed as follows. In one embodiment, the synthesized oligonucleotides are expressed as both soluble and pIII-fusion proteins within the same cell. When the infected bacterial cell expresses both types of molecules, the heterodimerization domain allows both types of molecules to associate in the periplasmic space and be transported to the surface of the M13 particle. This method is analogous to the assembly of heavy and light chain antibody molecules on the: surface of phage (Hoogengoom et al., 1991; Nucl. Acids. Res. 19: 4133–4137). In another embodiment,a single synthetic oligonucleotide pIII fusion protein includes both of the dimerization domains so that they interact in an intramolecular fashion. Again, this method is analogous to single chain antibody expression on the surface of phage (Barbas et al., 1992, Proc. Nat'l. Acad. Sci. USA, 89: 4457–4461).

5.1.3. EXPRESSION OF VECTORS

Once the appropriate expression vectors are prepared, they are inserted into an appropriate host, such as *E. coli. Bacillus subtilis*, insect cells, mammalian cells, yeast cells, etc., for example by electroporation, and the plurality of oligonucleotides is expressed by culturing the transfected host cells under appropriate culture conditions for colony or phage production. Preferably, the host cells are protease deficient, and may or may not carry suppressor tRNA genes.

A small aliquot of the electroporated cells are plated and the number of colonies or plaques are counted to determine the number of recombinants. The library of recombinant vectors in host cells is plated at high density for a single amplification of the recombinant vectors.

For example, recombinant M13 vector m666, m655 or m663, engineered to contain the synthesized double stranded oligonucleotides according to the invention, are transfected into DH5αF' *E. coli* cells by electroporation. TSARs are expressed on the outer surface of the viral capsid extruded from the host *E. coli* cells and are accessible for screening. The parent m666, m655 or m663 vectors contain the c-myc stuffer fragment. When the double stranded synthesized oligonucleotides are inserted between the Xho I and Xba I sites, the stuffer fragment is removed. The cloning efficiency of the expressed library is easily determined by filter blotting with the 9E10 antibody that recognizes the c-myc stuffer fragment.

Alternatively, when the double stranded synthesized oligonucleotides are cloned just at the Xho I or. Xba I site, the c-myc epitope is retained. Then the c-myc epitope is expressed in the pIII-fusion protein expressed by the vector. An advantage of the m663 vector is that it contains an intact LacZ+ gene, which can be easily seen as a blue dot when expressed in E. coli plated on Xgal and IPTG.

TSARs can be expressed in a plasmid vector contained in bacterial host cells such as E. coli. The TSAR proteins accumulate inside the E. coli cells and a cell lysate is prepared for screening. Use of plasmid p340-1D is described as an illustrative example. A TSAR library in p340-1D as described above, expressed the co-functional fusion protein with β-galactosidase. In the parent vector (without synthetic oligonucleotide) the β-galactosidase gene is out of frame and therefore nonfunctional. When plated on LB plates with ampicillin, IPTG and Xgal, the colonies that have TSAR oligonucleotides yield blue colonies, whereas colonies harboring non-recombinant p340-1D or p340-1D recombinants with oligonucleotides carrying unsuppressed stop codons will be white. The relative number of blue and white colonies reveals the percent recombinants, and is useful in estimating the total numbers of recombinants in the library, and is also useful in screening (see Section 5.2, infra).

The pLamB plasmid vector containing the synthesized double stranded oligonucleotides can be electroporated into E. coli cells and transformants are selected on LB plates with ampicillin. After an overnight incubation at 37° C., the plates are covered with LB and cells are collected and pooled from all the plates. Glycerol is added to 20%, to these cells and aliquots are stored at −70° C. and are used for screening for the TSAR proteins expressed in the E. coli outer membrane which is accessible for screening.

Phagemid vectors containing the synthesized double stranded oligonucleotides, expressed on the outer surface of the extruded phage, are propagated either as infected bacteria or as bacteriophage with helper phage.

The expressed pDAF2-3 phagemids have the added advantage that they include the c-myc gene which can serve as an "epitope tag" for the fusion. pIII proteins. Approximately 0.1–10% of the phage carrying the phagemid genome incorporate the fusion pIII molecule. The intactness of the chimeric pIII proteins is evaluated based on the expression of the c-myc epitope. By following the expression of the c-myc epitope using the 9E10 antibody, it is possible to monitor the successful incorporation of the fusion pIII molecule into the M13 viral particle.

Also when expressing pDAF2, the upstream c-myc peptide is detected immunologically using the 9E10 antibody, then it can be assumed that the downstream synthesized oligonucleotide, expressed TSAR peptide is appropriately expressed.

In addition, it may be of value to electroporate several different strains of E. coli and establish different versions of the same library. Of course, the same E. coli strain would need to be used for the entire set of screening experiments. This strategy is based on the consideration that there is likely an in vivo biological selection, both positive and negative, on the viral assembly, secretion, and infectivity rate of individual M13 recombinants due to the sequence nature of the peptide-pIII fusion proteins. Therefore, E. coli with different genotypes (i.e., chaperone overexpressing, or secretion enhanced) will serve as bacterial hosts, because they will yield libraries that differ in subtle, unpredictable ways.

5.2. METHODS TO IDENTIFY TSARs: SCREENING LIBRARIES

Once a library has been constructed according to the methods of the invention, the library is screened to identify TSARs having binding affinity for a ligand of choice. As stated above, in the present invention, a ligand is intended to encompass a substance, including a molecule or portion thereof, for which a proteinaceous receptor naturally exists or can be prepared according to the method of the invention. Thus in this invention, a ligand is a substance that specifically interacts with the binding domain of a TSAR and includes, but is not limited to, a chemical group, an ion, a metal, a protein, glycoprotein or any portion thereof, a peptide or any portion of a peptide, a nucleic acid or any portion of a nucleic acid, a sugar, a carbohydrate or carbohydrate polymer, a lipid, a fatty acid, a viral particle or portion thereof, a membrane vesicle or portion thereof, a cell wall component, a synthetic organic compound, a bioorganic compound and an inorganic compound.

Screening the TSAR libraries of the invention can be accomplished by any of a variety of methods known to those of skill in the art.

If the TSARs are expressed as fusion proteins with a cell surface molecule, then screening is advantageously achieved by contacting the vectors with an immobilized target ligand and harvesting those vectors that bind to said ligand. Such useful screening methods designated "panning" techniques are described in Fowlkes et al., 1992, BioTechniques 13(3): 422–27. In panning methods useful to screen the present libraries, the target ligand can be immobilized on plates, beads, such as magnetic beads, sepharose, etc., beads used in columns. In particular embodiments, the immobilized target ligand can be "tagged", e.g., using such as biotin, 2-fluorochrome, e.g. for FACS sorting.

Screening a library of phage expressing TSARs, i.e., phage and phagemid vectors can be achieved as follows using magnetic beads. Target ligands are conjugated to magnetic beads, according to the instructions of the manufacturers. To block non-specific binding to the beads, and any unreacted groups, the beads are incubated with excess BSA. The beads are then washed with numerous cycles of suspension in PBS-0.5% Tween 20 and recovered with a strong magnet along the sides of a plastic tube. The beads are then stored with refrigeration, until needed.

In the screening experiments, an aliquot of the library is mixed with a sample of resuspended beads. The tube contents are tumbled at 4° C. for 1–2 hrs. The magnetic beads are then recovered with a strong magnet and the liquid is removed by aspiration. The beads are then washed by adding PBS-0.5% Tween 20, inverting the tube several times to resuspend the beads, and then drawing the beads to the tube wall with the magnet. The contents are then removed and washing is repeated 5–10 additional times. 50 mM glycine-HCl (pH 2.2), 100 mg/ml BSA solution are added to the washed is beads to denature proteins and release bound phage. After a short incubation time, the beads are pulled to the side of the tubes with a strong magnet and the liquid contents are then transferred to clean tubes. 1M Tris-CHl (pH 7.5) or 1M $NaH_2PO_4$ (pH 7) is added to the tubes to neutralize the pH of the phage sample. The phage are then diluted, e.g., $10^{-3}$ to $10^{-6}$, and aliquots plated with E. coli DH5α F' cells to determine the number of plaque forming units of the sample. In certain cases, the platings are done in the presence of XGal and IPTG for color discrimination of plaques (i.e., lacZ+ plaques are blue, lacZ− plaques are white). The titer of the input samples is also determined for comparison (dilutions are generally $10^{-6}$ to $10^{-9}$). See Section 7.1, infra, for additional details.

Alternatively, screening a library of phage expressing TSARs can be achieved as follows using microtiter plates. Target ligand is diluted, e.g., in 100 mM $NaHCO_3$, pH 8.5 and a small aliquot of ligand solution is adsorbed onto wells of microtiter plates (by incubation overnight at 4° C. An aliquot of BSA solution (1 mg/ml, in 100 mM $NaHCO_3$, pH 8.5) is added and the plate incubated at room temperature for 1 hr. The contents of the microtiter plate are flicked out and the wells washed carefully with PBS-0.5% Tween 20. The plates are washed free of unbound targets repeatedly. A small aliquot of phage solution is introduced into each well and the wells are incubated at room temperature for 1–2 hrs. The contents of microtiter plates are flicked out and washed repeatedly. The plates are incubated with wash solution in each well for 20 minutes at room temperature to allow bound phage with rapid dissociation constants to be released. The wells are then washed five more times to remove all unbound phage.

To recover the phage bound to the wells, a pH change is used. An aliquot of 50 mM glycine-HCl (pH 2.2), 100 mg/ml BSA solution is added to washed wells to denature proteins and release bound phage. After 5–10 minutes, the contents are then transferred into clean tubes, and a small aliquot of 1M Tris-HCl (pH 7.5) or 1M $NaH_2PO_4$ (pH 7) is added to neutralize the pH of the phage sample. The phage are then diluted, e.g., $10^{-3}$ to $10^{-6}$ and aliquots plated with $E.\ coli$ DH5αF' cells to determine the number of the plaque forming units of the sample. In certain cases, the platings are done in the presence of XGal and IPTG for color discrimination of plaques (i.e., lacZ+ plaques are blue, lacZ– plaques are white). The titer of the input samples is also determined for comparison (dilutions are generally $10^{-6}$ to $10^{-9}$).

Screening a library of plasmid vectors expressing TSARs on the outer surface of bacterial cells can be achieved using magnetic beads as follows. Target ligands are conjugated to magnetic beads essentially as described above for screening phage vectors.

A sample of bacterial cells containing recombinant plasmid vectors expressing a plurality of TSAR proteins expressed on the surface of the bacterial cells is mixed with a small aliquot of resuspended beads. The tube contents are tumbled at 4° C. for 1–2 hrs. The magnetic beads are then recovered with a strong magnet and the liquid is removed by aspiration. The beads are then washed, e.g., by adding 1 ml of PBS-0.5% Tween 20, inverting the tube several times to resuspend the beads, and drawing the beads to the tube wall with the magnet and removing the liquid contents. The beads are washed repeatedly 5–10 additional times. The beads are then transferred to a culture flask that contains a sample of culture medium, e.g. LB+ ampicillin. The bound cells undergo cell division in the rich culture medium and the daughter cells will detach from the immobilized targets. When the cells are at log-phase, inducer is added again to the culture to generate more TSAR proteins. These cells are then harvested by centrifugation and rescreened.

Successful screening experiments are optimally conducted using 3 rounds of serial screening. The recovered cells are then plated at a low density to yield isolated colonies for individual analysis. The individual colonies are selected and used to inoculate LB culture medium containing ampicillin. After overnight culture at 37° C., the cultures are then spun down by centrifugation. Individual cell aliquots are then retested for binding to the target ligand attached to the beads. Binding to other beads, having attached thereto, a non-relevant ligand can be used as a negative control.

Alternatively, screening a library of plasmid vectors expressing TSARs on the surface of bacterial cells can be achieved as follows. Target ligand is adsorbed to microtiter plates as described above for screening phage vectors. After the wells are washed free of unbound target ligand, a sample of bacterial cells is added to a small volume of culture medium and placed in the microtiter wells. After sufficient incubation, the plates are washed repeatedly free of unbound bacteria. A large volume, approximately 100 ml of LB+ ampicillin is added to each well and the plate is incubated at 37° C. for 2 hrs. The bound cells undergo cell division in the rich culture medium and the daughter cells detach from the immobilized targets. The contents of the wells are then transferred to a culture flask that contains ~10 ml LB+ ampicillin. When the cells are at log-phase, inducer is added again to the culture to generate more TSAR proteins. These cells are then harvested by centrifugation and rescreened.

Screening can be conducted using rounds of serial screening as described above, with respect to screening using magnetic beads.

According to another embodiment, the libraries expressing TSARs as a surface protein of either a vector or a host cell, e.g., phage or bacterial cell can be screened by passing a solution of the library over a column of a ligand immobilized to a solid matrix, such as sepharose, silica, etc., and recovering those phage that bind to the column after extensive washing and elution.

According to yet another embodiment, weak binding library members can be isolated based on a retarded chromatographic properties. According to one mode of this embodiment for screening, fractions are collected as they come off the column, saving the trailing fractions (i.e., those members that are retarded in mobility, relative to the peak fraction are saved). These members are then concentrated and passed over the column a second time, again saving the retarded fractions. Through successive rounds of chromatography, it is possible to isolate those that have some affinity, albeit weak, to the immobilized ligand. These library members are retarded in their mobility because of the millions of possible ligand interactions as the member passes down the column. In addition, this methodology selects those members that have modest affinity to the target, and which also have a rapid dissociation time. If desired, the oligonucleotides encoding the TSAR binding domain selected in this manner can be mutagenized, expressed and rechromatographed (or screened by another method) to discover improved binding activity.

Alternatively, the libraries can be screened to recover members that are retained on plastic plates (e.g., ELISA plates) or magnetic beads (covalent or non-specific linkage) that have an immobilized ligand. According to another embodiment, homobifunctional (e.g., DSP, DST, BSOCOES, EGS, DMS) or heterobifunctional (e.g., SPDP) cross-linking agents can be used in combination with any of the above methods, to promote capture of weak binding members; these cross-linkers should be reversible, with a treatment (i.e., exposure to thiols, base, periodate, hydroxylamine) gentle enough not to disrupt members structure or infectivity, to allow recovery of the library member. The elution reagents can be removed by dialysis (i.e., dialysis bag, Centricon/Amicon microconcentrators).

One important aspect of screening the libraries is that of elution. For clarity of explanation, the following is discussed in terms of TSAR expression by phage; however, it is readily understood that such discussion is applicable to any system where the TSAR is expressed on a surface fusion molecule. It is conceivable that from a plurality of proteins expressed on phage, that the conditions that disrupt the peptide-target interactions during recovery of the phage are specific for every given peptide sequence. For example, certain interactions may be disrupted by acid pH's but not by basic pH's, and vice versa. Thus, it is important to test a variety of elution conditions (including but not limited to pH 2–3, pH 12–13, excess target in competition, detergents, mild protein denaturants, urea, varying temperature, light, presence or absence of metal ions, chelators, etc.) and compare the primary structures of the TSAR proteins expressed on the phage recovered for each set of conditions to determine the appropriate elution conditions for each ligand/TSAR combination. Some of these elution conditions may be incompatible with phage infection because they are bactericidal and will need to be removed by dialysis (i.e., dialysis bag, Centricon/Amicon microconcentrators).

The ability of different expressed proteins to be eluted under different conditions may not only be due to the denaturation of the specific peptide region involved in binding to the target but also may be due to conformational changes in the flanking regions. These flanking sequences may also be denatured in combination with the actual binding sequence; these flanking regions may also change their secondary or tertiary structure in response to exposure to the elution conditions (i.e., pH 2–3, pH 12–13, excess target in competition, detergents, mild protein denaturants, urea, heat, cold, light, metal ions, chelators, etc.) which in turn leads to the conformational deformation of the peptide responsible for binding to the target.

According to another alternative embodiment in which the TSARs contain a linker region between the binding domain and the effector domain, particular TSAR libraries can be prepared and screened by: (1) engineering a vector, preferably a phage vector, so that a DNA sequence encodes a segment of collagen (or collagenase cleavable peptide) and is present adjacent to the gene encoding the effector domain, e.g., the pIII coat protein gene, flanked by a DNA fragment encoding a pair of cysteine residues that cross-bridge reproducibly in a manner such that the collagen segment is still cleavable by collagenase; (2) construct and assemble the double stranded synthetic oligonucleotides as described above and insert into the engineered vector; (3) express the plurality of vectors in a suitable host to form a library of vectors; (4) treat the entire library with collagenase once; (5) screen for binding to an immobilized ligand; (6) wash away excess phage; and (7) elute all bound phage with excess DTT (i.e., 1 mM). Because DTT is such a small molecule (M.W. 154.3), it can easily be in a high molar excess relative to the phage and should be very effective in reaching the cross-bridged bond of the tethered phage. After reduction of the disulfide bond, the particle will be uncoupled from the peptide-ligand complex and can then be used to infect bacteria to regenerate the particle with its full-length pIII molecule for additional rounds of screening. This alternative embodiment advantageously allows the use of universally effective elution conditions and thus allows identification of phage expressing TSARs that otherwise might not be recovered using other known methods for elution. To illustrate, using this embodiment, exceptionally tight binding TSARs could be recovered.

FIG. 7 schematically depicts a method for screening a library to identify ligand-binding TSARs expressed in a plasmid vector as a secreted protein which accumulates inside the host cell. Use of plasmid p340-1D is described as an illustrative example. A TSAR library constructed in p340-1D after introducing Xho I and Xba I sites, as described above in Section 5.1.2 see also Section 9, infra) can be screened as follows. The Xho I+ Xba I cleaved oligonucleotides are ligated with T4 DNA ligase to Xba I+ Xho I cleaved p340-1D, and transfected into $E.\ coli$ that is lacZ–, supE+. To select for successful transformations, the preparation is plated onto 100 separate petri plates containing Luria Broth (LB) and ampicillin (100 $\mu$g/ml). After an overnight incubation at 37° C., the colonies are pooled from each plate by adding 5 ml liquid LB medium and scraping with a glass bar. The cells are then washed by centrifugation and suspension with the final resuspension in 20% glycerol. The pool is divided into 100 individual aliquots and frozen (–70° C.).

A small aliquot of the transfected cells is plated out on LB plates with ampicillin and IPTG and XGal at a low density to yield individual colonies. Colonies that have TSAR oligonucleotides with an open reading frame yield blue colonies, whereas colonies harboring non-recombinant p340-1D or p340-1D recombinants with oligonucleotides carrying non-suppressed stop codons are white. The relative numbers of blue and white colonies reveal the percent recombinants; this number is useful in estimating the total number of recombinants in the library. For screening purposes, the 100 frozen aliquots can be thawed and a small volume (~100 $\mu$l) removed from each to start cultures (25 ml) in LB+ ampicillin. When the cells are in log phase growth, IPTG is added to the cultures (final concentration of 200 $\mu$M) to induce expression of a plurality or proteins encoded by the TSAR peptide-$\beta$ galactosidase gene fusions. After approximately 2 hour of induction, the cells are harvested by centrifugation and the TSAR peptide-$\beta$ galactosidase fusion proteins purified as described in application Ser. No. 07/480,420 at Section 11 (parent application). The purified proteins are concentrated with an Amicon microconcentrator. The 100 samples of fusion proteins are then screened for binding to immobilized targets. These targets can either be pure or part of a complex mixture. Furthermore, the targets can be affixed to microtiter dish wells, spotted on nitrocellulose or nylon filters, or linked to matrix beads.

Typically screening consists of incubating the plurality of TSAR peptide-$\beta$ galactosidase fusion proteins with the immobilized target. For the sake of clarity, the targets are described below as being affixed to a microtiter dish well. A small amount (5–50 $\mu$l) of each aliquot is added to microtiter dish wells that have the same target immobilized in each well. After a 1–2 hour incubation, the contents of the wells are flicked out, and the wells are washed with PBS-5% Tween 20 approximately ten times. To determine which wells have retained TSAR peptide-$\beta$ galactosidase fusion proteins, ONPG reagents are added to the wells for color development. The optical density of the wells is determined with a plate reader.

Those wells that have a positive color reaction are then correlated with the aliquots tested. Cells corresponding to those aliquots are thawed again, diluted with fresh LB liquid (~$10^6$ fold) and distributed onto 20 petri plates (LB+amp). The colonies that form on each plate are pooled from each plate by adding 5 ml liquid LB medium and scraping with a glass bar. The cells are then washed by centrifugation and resuspension with the final resuspension in 20% glycerol. The pool is then divided into 20 individual aliquots and frozen at –70° C. Each aliquot is next grown up as a liquid culture and when the cells are in log phase growth, IPTG is added to the cultures (final concentration of 200 $\mu$M) to induce expression of a plurality of proteins encoded by the TSAR peptide-β galactosidase fusion proteins purified as described in the parent application at Section 11. The purified proteins are then concentrated with an Amicon microconcentrator.

As can be seen, screening, identification of positive wells, subdividing the appropriate frozen cell aliquots onto petri plates, and preparation of fusion proteins constitute a screening cycle. The cycle can be reiterated in a winnowing manner to finally identify single isolates that carry a TSAR peptide-β galactosidase fusion protein that has binding activity. This method of recombinant DNA isolation is analogous to current methodologies for isolating recombinants from libraries based on hybridization or immunological detection (see Maniatis) or identification of hybridomas (see FIG. 7).

This methodology has several advantages. First, the TSAR peptide is not expressed until the time of induction, and there may be less opportunity for biological selection on the library. Second, enzymes like β-galactosidase provide powerful effector domains since they are catalytic. Third, the method of screening lends itself well to current expertise available in most molecular biology and immunology laboratories. Fourth, very large proteins have been fused to β-galactosidase without inactivating the enzyme. β-galactosidase appears to be very tolerant of insertions/fusion at its N-terminus, a characteristic that is useful in expressing large TSARs.

5.3. TSARs AND COMPOSITIONS COMPRISING A TSAR BINDING DOMAIN

In the present invention, novel totally synthetic affinity reagents called TSARs are identified which can be produced as soluble, easily purified proteins/polypeptides and/or peptides that can be made and isolated in commercial quantities. These TSAR reagents are concatenated heterofunctional proteins, polypeptides and/or peptides that include at least two distinct functional regions. One region of the heterofunctional TSAR molecule is a binding domain with affinity for a ligand that is characterized by 1) its strength of binding under specific conditions, 2) the stability of its binding under specific conditions, and 3) its selective specificity for the chosen ligand. A second region of the heterofunctional TSAR molecule is an effector domain that is biologically or chemically active to enhance expression and/or detection of the TSAR. The effector domain is chosen from a number of biologically or chemically active proteins including a structural protein that is accessibly expressed as a surface protein of a vector, an enzyme or fragment thereof, a toxin or fragment thereof, a therapeutic protein or peptide or a protein or a peptide whose function is to provide a site for attachment of a substance such as a metal ion, etc., that is useful for enhancing expression and/or detection of the expressed TSAR.

According to one embodiment of the invention, a TSAR can contain an optional additional region, i.e., a linker domain between the binding domain and the effector domain. FIG. 8 schematically represents a TSAR according to this embodiment of the invention. The presence or absence of the peptide linker domain is optional as is the type of linker that may be used.

The linker region serves (1) as a structural spacer region between the binding and effector domains; (2) as an aid to uncouple or separate the binding and effector domains; or (3) as a structural aid for display of the binding domain and/or the TSAR by the expression vector. The linker sequence can be stable and provide for separation of the TSAR regions or it can be susceptible to cleavage by chemical, biological, physical or enzymatic means. If a cleavable linker is used, the sequence employed is one that allows the binding domain portion of the TSAR to be released from the effector domain of the TSAR protein. Thus when a linker is used that is susceptible to cleavage, the heterofunctional TSAR protein can be an intermediate in the production of a unifunctional binding protein, polypeptide or peptide having the same binding specificity as the TSAR.

In a particular embodiment, the cleavable sequence is one that is enzymatically degradable. A collagenase susceptible sequence is but one example (see, for example, Section 9, infra). Other useful sequences that can be used as an enzymatically cleavable linker domain are those which are susceptible to enterokinase or Factor Xa cleavage. For example, enterokinase cleaves after the lysine in the sequence Asp-Asp-Asp-Lys (SEQ ID NO 18). Factor Xa is specific to a site having the sequence Ile-Glu-Gly-Arg, (SEQ ID NO 19) and cleaves after arginine. Another useful sequence is Leu-Val-Pro-Arg-Gly-Ser-Pro (SEQ ID NO 20) which is cleaved by thrombin between the Arg and Gly residues. Other enzyme cleavable sequences that can be used are those encoding sites recognized by microbial proteases, peptidases, viral proteases, the complement cascade enzymes and enzymes of the blood coagulation/clot dissolution pathway. Other enzyme cleavable sequences will also be recognized by those skilled in the art and are intended to be included in this embodiment of the invention. Alternatively, the sequence may be selected so as to contain a site cleavable by chemical means, such as cyanogen bromide, which attacks methionine residues in a peptide sequence. Another chemical means of cleavage includes the use of formic acid which cleaves at proline residues in a peptide sequence. The invention is not to be limited to the specific examples of chemical cleavage provided here but includes the use of any chemical cleavage method known to those with skill in the art. TSARs having a cleavable linker portion, thus, can serve as intermediates in the production of unifunctional proteins, polypeptides or peptides having a binding function and specificity for a ligand of choice.

Alternatively, the linker portion can be stable or impervious to chemical and/or enzymatic cleavage and serve as a link between the binding domain and the other peptide portion(s) of the TSAR. For example, the linker domain can be a deformable protein moiety which can serve as a shape-controllable aid for recovery of the binding domain during elution. As another example, the linker domain can provide a (a) hinge or link region, such as provided by one or more proline residues; (b) a swivel region, such as provided by one or more glycine residues; or (c) a heterodimerization domain such as provided by a c-fos or c-jun sequence which aid in displaying the TSAR binding domains in the form of bimolecular pockets (see FIG. 1C).

The chemically or biologically active effector domain of the TSAR imparts detectable, diagnostic, enzymatic or therapeutic characteristics to the TSAR. The enzymatic activity or therapeutic activity may be useful in identifying or detecting the TSAR during the screening process as well as being useful, e.g., for therapeutic effects where the TSAR is employed in an in vivo application. For example, a therapeutic group with a proteolytic activity attached to a binding domain with affinity for fibrin results in a TSAR that binds to fibrin components in blood clots and dissolves them.

Alternatively, the effector domain can be a protein moiety that binds a metal, including but not limited to radioactive, magnetic, paramagnetic, etc. metals, and allows detection of the TSAR. Other examples of biologically or chemically active effector peptides that can be used in TSARs include but are not limited to toxins or fragments thereof, peptides that have a detectable enzymatic activity, peptides that bind metals, peptides that bind specific cellular or extracellular components, peptides that enhance expression of the TSAR molecule, peptides that interact with fluorescent molecules, and peptides that provide a convenient means for identifying the TSAR.

In a particular embodiment found in the example in Section 9 infra, the full sequence of the enzyme β-galactosidase was used as the effector domain of the TSAR. This protein provides a visual means of detection upon addition of the proper substrate, e.g., X-gal or ONPG. However, the effector domain of the TSAR need not be the complete coding sequence of a protein. A fraction of a protein that is readily expressed by the host cell and that has the desired activity or function may be used.

According to the most general embodiment of the invention, there is no intended specified order for the two or more regions of the TSAR relative to each other except that the linker domain, if present, must be between the binding domain and the effector domain of the TSAR. The positions of the regions of the TSAR are otherwise interchangeable. According to a more preferred embodiment, the binding domain is located at the N-terminal end of the heterofunctional protein, polypeptide or peptide and the effector domain is located at the carboxyl terminal end.

According to another embodiment of the invention, the TSAR can include multiple binding domains or multiple active effector portions or combinations of multiples of each.

Once a TSAR binding a ligand of choice has been identified by the method of the invention, the amino acid sequence of the binding domain of the TSAR can be deduced from the nucleotide sequence of the inserted oligonucleotide sequence in the vector identified as expressing the TSAR. The protein/peptide comprising the binding domain of the TSAR can be produced either by recombinant DNA techniques or synthesized by standard chemical methods known in the art (e.g., see Hunkapiller et al., 1984, Nature 310: 105–111). Whether produced by recombinant or chemical synthetic techniques, the proteins/peptides comprising the binding domain of the identified TSAR include those having an amino acid sequence identical to the TSAR binding domain as well as those in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the non-polar (hydrophobic) amino acids include glycine, alanine, leucine, isoleucine, valine, proline, phenylalanine, tryptophan and methionine. The polar neutral amino acids include serine, threonine, cysteine, tyrosine, asparagine and glutamine. The positively charged (basic) amino acids include arginine, lysine and histidine. The negatively charged (acidic) amino acids include aspartic and glutamic acid.

When a TSAR has been identified as a binder for a particular target ligand of interest according to the method of the invention, it may be useful to determine what region(s) of the expressed TSAR peptide sequence is (are) responsible for binding to the target ligand. Such analysis can be conducted at two different levels, i.e., the nucleotide sequence and amino acid sequence levels.

By molecular biological techniques it is possible to verify and further analyze a ligand binding TSAR at the level of the oligonucleotides. First, the inserted oligonucleotides can be cleaved using appropriate restriction enzymes and religated into the original expression vector and the expression product of such vector screened for ligand binding to verify that the TSAR oligonucleotides encode the binding peptide. Second, the oligonucleotides can be transferred into another vector, e.g., from phage to phagemid or to p340-1D or to pLamB plasmid. The newly expressed fusion proteins should acquire the same binding activity if the domain is necessary and sufficient for binding to the ligand. This last approach also assesses whether or not flanking amino add residues encoded by the original vector (i.e., fusion partner) influence TSAR peptide in any fashion. Third, the oligonucleotides can be synthesized, based on the nucleotide sequence determined for the TSAR, amplified by cloning or PCR amplification using internal and flanking primers cleaved into two pieces and cloned as two half-TSAR fragments. In this manner, the inserted oligonucleotides are subdivided into two equal halves. If the TSAR domain important for binding is small, then one recombinant clone would demonstrate binding and the other would not. If neither have binding, then either both are important or the essential portion of the domain spans the middle (which can be tested by expressing just the central region).

Alternatively, by synthesizing peptides corresponding to the predicted TSAR peptide, the binding domains can be analyzed. First, the entire peptide should be synthesized and assessed for binding to the target ligand to verify that the TSAR peptide is necessary and sufficient for binding. Second, short peptide fragments, for example, overlapping 10 mers, can by synthesized, based on the amino acid sequence of the TSAR binding domain, and tested to identify those binding the ligand.

In addition, in certain instances, linear motifs may become apparent after comparing the primary structures of different TSARs having binding affinity for a target ligand. The contribution of these motifs to binding can be verified with synthesized peptides in competition experiments (i.e., determine the concentration of peptide capable of inhibiting 50% of the binding of the phage to its target; $IC_{50}$). See, for example, Section 7.2, infra. Conversely, the motif or any region suspected to be important for binding can be removed or mutated from the DNA encoding the TSAR insert and the altered displaced peptide can be retested for binding.

These protein/peptide compositions comprising a binding domain of a TSAR or a portion thereof having the same binding specificity as said binding domain, designated herein as "TSAR compositions" are encompassed within the invention and are useful for the applications described in Section 5.4 (infra).

Furthermore, once the binding domain of a TSAR has been identified, new TSARs can be created by isolating and fusing the binding domain of one TSAR to a different effector domain. The biologically or chemically active effector domain of the TSAR can thus be varied. Alternatively, the binding characteristics of an individual TSAR can be modified by varying the TSAR binding domain sequence to produce a related family of TSARs with differing properties for a specific ligand.

Moreover, in a method of directed evolution, the identified TSAR proteins/peptides can be improved by additional rounds of mutagenesis, selection, and amplification of the nucleotide sequences encoding the TSAR binding domains. Mutagenesis can be accomplished by creating and cloning a new set of oligonucleotides that differ slightly from the parent sequence, ee, 1–10%. Selection and amplification are achieved as described above. To verify that the isolated peptides have improved binding characteristics, mutants and the parent phage, differing in their LacZ expression, can be processed together during the screening experiments. Alteration of the original blue-white color ratios during the course of the screening experiment will serve as a visual means to assess the successful selection of enhanced binders. This process can go through numerous cycles.

5.4. APPLICATIONS AND USES OF TSARs AND TSAR COMPOSITIONS

TSARs and TSAR compositions comprising a binding domain of a TSAR or a portion thereof having the same binding specificity as the TSAR identified according to the novel methods of the invention are useful for in vitro and in vivo applications which heretofore have been performed by binding regions of antibodies, DNA binding proteins, RNA binding proteins, metal binding proteins, nucleotide fold and GTP binding proteins, calcium binding proteins, adhesive proteins such as integrins, adhesins, lectins, enzymes, or any other small peptide or portion of a macromolecule that has binding affinity for a ligand.

The TSAR products c an be used in any industrial or pharmaceutical application that uses a peptide binding moiety specific for any given ligand. The TSARs can also be intermediates in the production of unifunctional binding peptides that are produced and selected by the method of the invention to have a binding affinity, specificity and avidity for a given ligand. Thus, according to the present invention, TSARs and TSAR compositions are used in a wide variety of applications, including but not limited to, uses in the field of biomedicine; biologic control and pest regulation; agriculture; cosmetics; environmental control and waste management; chemistry; catalysis; nutrition and food industries; military uses; climate control; pharmaceuticals; etc. The applications described below are intended as illustrative examples of the uses of TSARs and compositions comprising the binding domain of a TSAR and are in no way intended as a limitation thereon. Other applications will be readily apparent to those of skill in the art and are intended to be encompassed by the present invention.

The TSARs and TSAR compositions are useful in a wide variety of in vivo applications in the fields of biomedicine, bioregulation, and control. In certain of these applications, the TSARs are employed as mimetic replacements for compositions such as enzymes, hormone receptors, immunoglobulins, metal binding proteins, calcium binding proteins, nucleic acid binding proteins, nucleotide binding proteins, adhesive proteins such as integrins, adhesins, lectins, etc. In others of these applications, the TSARs are employed as mimetic replacements of proteins/peptides, sugars or other molecules that bind to receptor molecules, such as for example, mimetics for molecules that bind to streptavadin, immunoglobulins, cellular receptors, etc.

Other in vivo uses include administration of TSARs and TSAR compositions as immunogens for vaccines, useful for active immunization procedures. TSARs can also be used to develop immunogens for vaccines by generating a first series of TSARs specific for a given cellular or viral macromolecular ligand and then developing a second series of TSARs that bind to the first TSARs i.e., the first TSAR is used as a ligand to identify the second series of TSARs. The second series of TSARs will mimic the initial cellular or viral macromolecular ligand site but will contain only relevant peptide binding sequences, eliminating irrelevant peptide sequences. Either the entire TSAR developed in the second series, or the binding domain, or a portion thereof, can be used as an immunogen for an active vaccination program.

In in vivo applications TSARs and TSAR compositions can be administered to animals and/or humans by a number of routes including injection (e, intravenous, intraperitoneal, intramuscular, subcutaneous, intraauricular, intramammary, intraurethrally, etc.), topical application, or by absorption through epithelial or mucocutaneous linings. Delivery to plants, insects and protists for bioregulation and/or control can be achieved by direct application to the organism, dispersion in the habitat, addition to the surrounding environment or surrounding water, etc.

In the chemical industry, TSARs can be employed for use in separations, purifications, preparative methods, and catalysis.

In the field of diagnostics, TSARs can be used to detect ligands occurring in lymph, blood, urine, feces, saliva, sweat, tears, mucus, or any other physiological liquid or solid. In the area of histology and pathology, TSARs can be used to detect ligands in tissue sections, organ sections, smears, or in other specimens examined macroscopically or microscopically. TSARs can also be used in other diagnostics as replacements for antibodies, as for example in hormone detection kits, or in pathogen detection kits, etc., where a pathogen can be any pathogen including bacteria, viruses, mycoplasma, fungi, protozoans, etc. TSARs may also be used to define the epitopes that monoclonal antibodies bind to by using monoclonal antibodies as ligands for TSAR binding, thereby providing a method to define the epitope of the original immunogen used to develop the monoclonal antibody. TSARs or the binding domain or a portion thereof can thus serve as epitope mimetics and/or mimotopes.

The following examples are presented for purposes of illustration only and are not intended to limit the scope of the invention in any way.

6. EXAMPLE

PREPARATION OF TSAR LIBRARIES

TSAR libraries were prepared according to the present invention as set forth below.

6.1. PREPARATION OF THE TSAR-9 LIBRARY

6.1.1. SYNTHESIS AND ASSEMBLY OF OLIGONUCLEOTIDES

FIG. 2 shows the formula of the oligonucleotides and the assembly scheme used in construction of the TSAR-9 library. The oligonucleotides were synthesized with an applied Biosystems 380a synthesizer (Foster City, Calif.), and the full-length oligonucleotides were purified by HPLC.

Five micrograms of each of the pair of oligonucleotides were mixed together in buffer (67 mM Tris-HCl, pH 8.8, 10 mM β-mercaptoethanol, 16.6 mM ammonium sulfate, 6.7 mM EDTA and 50 µg/ml BSA), with 0.1% Triton X-100, 2 mM dNTP's, and 20 units of Taq DNA polymerase. The assembly reaction mixtures were incubated at 72° C. for 30 seconds and then 30° C. for 30 seconds; this cycle was repeated 60 times. It should be noted that the assembly reaction is not PCR, since a denaturation step was not used. Fill-in reactions were carried out in a thermal cycling device (Ericomp, LaJolla, Calif.) with the following protocol: 30 seconds at 72° C., 30 seconds at 30° C., repeated for 60 cycles. The lower temperature allows for annealing of the six base complementary region between the two sets of the oligonucleotide pairs. The reaction products were phenol/chloroform extracted and ethanol precipitated. Greater than 90% of the nucleotides were found to have been converted to double stranded synthetic oligonucleotides.

After resuspension in 300 µl of buffer containing 10 mM Tris-HCl, pH 7.5, 1 mM EDTA (TE buffer), the ends of the oligonucleotide fragments were cleaved with Xba I and Xho I (New England BioLabs, Beverly, Mass.) according to the supplier's recommendations. The fragments were purified by 4% agarose gel electrophoresis. The band of correct size was removed and electroeluted, concentrated by ethanol precipitation and resuspended in 100 µl TE buffer. Approximately 5% of the assembled oligonucleotides can be expected to have internal Xho I or Xba I sites; however, only the full-length molecules were used in the ligation step of the assembly scheme. The concentration of the synthetic oligonucleotide fragments was estimated by comparing the intensity on an ethidium bromide stained gel run along with appropriate quantitated markers. All DNA manipulations not described in detail were performed according to Maniatis, supra.

To demonstrate that the assembled enzyme digested oligonucleotides could be ligated, the synthesized DNA fragments were examined for their ability to self-ligate. The digested fragments were incubated overnight at 18° C. in ligation buffer with T4 DNA ligase. When the ligation products were examined by agarose gel electrophoresis, a concatamer of bands was visible upon ethidium bromide staining. As many as five different unit length concatamer bands (i.e., dimer, trimer, tetramer, pentamer, hexamer) were evident, suggesting that the synthesized DNA fragments were efficient substrates for ligation.

6.1.2. CONSTRUCTION OF VECTORS

The construction of the M13 derived phage vectors useful for expressing a TSAR library has been recently described (Fowlkes et al., 1992, BioTechniques, 13: 422–427). To express the TSAR-9 library, an M13 derived vector, m663, was constructed as described in Fowlkes. FIG. 4 illustrates the m663 vector containing the pIII gene having a c-myc-epitope, i.e., as a stuffer fragment, introduced at the mature N-terminal end, flanked by Xho I and Xba I restriction sites (see also, FIG. 1 of Fowlkes).

6.1.3. EXPRESSION OF THE TSAR-9 LIBRARY

The synthesized oligonucleotides were then ligated to Xho I and Xba I double-digested m663 RF DNA containing the pIII gene (Fowlkes) by incubation with ligase overnight at 12° C. More particularly, 50 ng of vector DNA and 5 ng of the digested synthesized DNA and was mixed together in 50 µl ligation buffer (50 mM Tris, pH 8.0, 10 mM $MgCl_2$, 20 mM DTT, 0.1 mM ATP) with T4 DNA ligase. After overnight ligation at 12° C., the DNA was concentrated by ethanol precipitation and washed with 70% ethanol. The ligated DNA was then introduced into E. coli (DH5αF'; GIBCO BRL, Gaithersburg, Md.) by electroporation.

A small aliquot of the electroporated cells was plated and the number of plaques counted to determine that $10^8$ recombinants were generated. The library of E. coli cells containing recombinant vectors was plated at a high density (~400, 000 per 150 mM petri plate) for a single amplification of the recombinant phage. After 8 hr, the recombinant bacteriophage were recovered by washing each plate for 18 hr with SMG buffer (100 mM NaCl, 10 mM Tris-HCl, pH 7.5, 10 mM $MgCl_2$, 0.05% gelatin) and after the addition of glycerol to 50% were frozen at −80° C. The TSAR-9 library thus formed had a working titer of $~2 \times 10^{11}$ pfu/ml.

6.2. PREPARATION OF TSAR-12 LIBRARY

FIG. 3 shows the formula for the synthetic oligonucleotides and the assembly scheme used in the construction of the TSAR-12 library. As shown in FIG. 3, the TSAR-12 library was prepared substantially the same as the TSAR-9 library described in Section 6.1 above with the following exceptions: (1) each of the variant non-predicted oligonucleotide sequences, i.e., NNB, was 30 nucleotides in length, rather than 54 nucleotides; (2) the restriction sites included at the 5' termini of the variant, non-predicted sequences were Sal I and Sp I, rather than Xho I and Xba I; and (3) the invariant sequence at the 3' termini to aid annealing of the two strands was GCGGTG rather than CCAGGT (5' to 3').

After synthesis including numerous rounds of annealing and chain extension in the presence of dNTP's and Taq DNA polymerase, and purification as described above in Section 6.1. 1, the synthetic double stranded oligonucleotide fragments were digested with Sal I and Spe I restriction enzymes and ligated with T4 DNA ligase to the nucleotide sequence encoding the M13 pIII gene contained in the m663 vector to yield a library of TSAR-12 expression vectors as described in Sections 6.1.2 and 6.1.3. The ligated DNA was then introduced into E. coli (DH5αF'; GIBCO BRL, Gaithersburg, Md.) by electroporation. The library of E. coli cells were plated at high density (~400,000 per 150 mm petri plate) for amplification of the recombinant phage. After about 8 hr. the recombinant bacteriophage were recovered by washing for 18 hr with SMG buffer and after the addition of glycerol to 50% were frozen at −80° C.

The TSAR-12 library thus formed had a working titer of $~2 \times 10^{11}$ pfu/ml.

6.3. CHARACTERIZATION OF THE TSAR-9 AND -12 LIBRARIES

The inserted synthetic oligonucleotides for each of the TSAR libraries, described in Sections 6.1 and 6.2 above, had a potential coding complexity of $20^{36}$ ($~10^{47}$) and since $~10^{14}$ molecules were used in each transformation experiment, each member of these TSAR libraries should be unique. After plate amplification the library solution or stock has $10^4$ copies of each member/ml.

It was observed that very few (<10%) of the inserted oligonucleotide sequences characterized so far in both of the libraries have exhibited deletions or insertions. This is likely a reflection of the accuracy in assembling the oligonucleotides under the conditions used and the fact that certain types of mutations (i.e., frame-shifts) would not be tolerated as pIII is an essential protein for phage propagation.

In order to determine whether any coding bias existed in the variant non-predicted peptides expressed by these libraries, perhaps due to biases imposed in vitro during synthesis of the oligonucleotides or in vivo during expression by the reproducing phage, inserts were sequenced as set forth below.

6.3.1. CHARACTERIZATION OF TSAR-9 LIBRARY

Inserted synthetic oligonucleotide fragments of 23 randomly chosen isolates were examined from the TSAR-9 library. Individual plaques were used to inoculate 1 ml of 2XYT broth containing E. coli (DH5αF') cells and the cultures were allowed to grow overnight at 37° C. with aeration. DNA was isolated from the culture supernatants according to Maniatis, supra. Twenty-three individual isolates were sequenced according to the method of Sanger (1979, Proc. Nat'l. Acad. Sci. USA 74: 5463–5467) using as a primer the oligonucleotide 5'-AGCGTAACGATCTCCCG (SEQ ID NO 21), which is 89 nucleotides downstream of the pIII gene cloning site of the m663 vector used to express the TSARs.

Nucleotide sequences and their encoded amino acid sequences were analyzed with the MacVector computer program (IBI, New Haven, Conn.). The Microsoft EXCEL program was used to evaluate amino acid frequencies. Such analyses showed that the nucleotide codons coding for and hence most amino acids, occurred at the expected frequency in the TSAR-9 library of expressed proteins. The notable exceptions were glutamine and tryptophan, which were over- and under-represented, respectively.

It is of interest to note the paucity of TAG stop codons in the inserts, i.e., only 2 of ~200 isolates characterized contained a TAG stop codon. About half [1-(47/48)[36]] of the phage inserts were expected to have at least one TAG codon in view of the assembly scheme used. However, most of the TAG-bearing phage appear to have been lost from the library, even though the bacterial host was supE. This may be a consequence of suppression being less than 100% effective.

The amino acids encoded by the inserted double stranded synthesized oligonucleotide sequences, excluding the fixed PG-encoding centers, were concatenated into a single sequence and the usage frequency determined for each amino acid using the Microsoft EXCEL program. The results are illustrated in FIG. 9. As shown in FIG. 9, these frequencies were compared to that expected from the assembly scheme of the oligonucleotides, and the divergence from expected values represented by the size of the bars above and below the baseline. Chi square analysis was used to determine the significance of the deviations; ■, ▨ and □ bars represent probability values of >93%, 75–93%, and <75%, respectively. As indicated in FIG. 9, the majority of amino acids were found to occur at the expected frequency, with the notable exceptions that glutamine and tryptophan were somewhat over- and under-represented, respectively. Thus, except for the invariant Pro-Gly, any position could have any amino acid; hence, the sequences are unpredicted or random.

6.3.2. CHARACTERIZATION OF TSAR-12 LIBRARY

Approximately 10 randomly chosen inserted oligonucleotides from the TSAR-12 library were examined by DNA sequencing as described above in Section 6.3.1. The isolates were chosen at random from the TSAR-12 library and prepared for sequencing as were the TSAR-9 isolates. Analysis showed that except for the invariant Gly any position could have any amino acid; hence, the sequences are unpredicted or random.

7. IDENTIFICATION OF LIGAND BINDING TSARS

In several series of experiments, the TSAR-9 and TSAR-12 libraries described in Section 6 above were screened, according to the present invention, for expressed proteins/peptides having binding specificity for a variety of different ligands of choice.

7.1. METHODS FOR SCREENING

The following methods were employed to screen the TSAR-9 and TSAR-12 libraries, except as otherwise noted.

The ligand of choice was conjugated to magnetic beads, obtained from one of two sources: Amine Terminated particulate supports, #8–4100B (Advanced Magnetics, Cambridge, Mass.) and Dynabeads M-450, tosylactivated (Dynal, Great Neck, N.Y.), according to the instructions of the manufacturer. To block any unreacted groups and non-specific binding to the beads, the beads were incubated with excess bovine serum albumin (BSA). The beads were then washed with numerous cycles of suspension in PBS-0.5% Tween 20, and recovered with a strong magnet. The beads were then stored at 4° C. until needed.

In the screening experiments, 1 ml of library was mixed with 100 µl of resuspended beads (1–5 mg/ml). The tube contents were tumbled at 4° C. for 1–2 hrs. The magnetic beads were then recovered with a strong magnet and the liquid was removed by aspiration. The beads were then washed by adding 1 ml of PBS-0.5% Tween 20, inverting the tube several times to resuspend the beads, drawing the beads to the tube wall with the magnet and removing the liquid contents. The beads were washed repeatedly 5–10 additional times. Fifty µl of 50 mM glycine-HCl (pH 2.2), 100 mg/ml BSA solution were added to the washed beads to denature proteins and release bound phage. After 5–10 minutes, the beads were pulled to the side of the tubes with a strong magnet and the liquid contents then transferred to clean tubes. To the tubes, 100 µl 1M Tris-HCl (pH 7.5) or 1M NaH$_2$PO$_4$ (pH 7) was added to neutralize the pH of the phage sample. The phage were then serially diluted from $10^{-3}$ to $10^{-6}$ and aliquots plated with E. coli DH5αF' cells to determine the number of plaque forming units of the sample. In certain cases, the platings were done in the presence of XGal and IPTG for color discrimination of plaques (i.e., lacZ$^+$ plaques are blue, lacZ$^-$ plaques are white). The titer of the input samples was also determined for comparison (dilutions were generally $10^{-6}$ to $10^{-9}$).

Successful screening experiments have generally involved 3 rounds of serial screening conducted in the following manner. First, the library was screened and the recovered phage rescreened immediately. Second, the phage that were recovered after the second round were plate amplified, according to Maniatis. The phage were eluted into SMG, by overlaying the plates with ~5 ml of SMG and incubating the plates at 4° C. overnight. Third, a small aliquot was then taken from the plate and rescreened. The recovered phage were then plated at a low density to yield isolated plaques for individual analysis.

The individual plaques were picked with a toothpick and used to inoculate cultures of E. coli F cells in 2XYT. After overnight culture at 37° C., the cultures were then spun down by centrifugation. The liquid supernatant was then transferred to a clean tube and served as the phage stock. Generally, it has a titer of $10^{12}$ pfu/ml which is stable at 4° C. Individual phage aliquots were then retested for their binding to the ligand coated beads and their lack of binding to other control beads (i.e., BSA coated beads, or beads conjugated with other ligand).

7.2. IDENTIFICATION OF 7E11-C5 BINDING TSARS

In one series of experiments, the TSAR-9 and TSAR-12 libraries were screened for expressed proteins/peptides having binding specificity for an anti-prostate carcinoma monoclonal antibody, i.e., the 7E11-C5 antibody. The 7E11-C5 monoclonal antibody is described in U.S. Pat. No. 5,162,504 issued Nov. 10, 1992.

The TSAR-9 or TSAR-12 library was screened as described above in Section 7.1 in serial fashion twice by contacting the expressed phage particles with Dynal magnetic beads (Great Neck, N.Y.) having the 7E11-C5 monoclonal antibody covalently attached according to the directions supplied by the manufacturer of the beads. The phage binding the 7E11-C5 monoclonal antibody were recovered using a strong magnet, and were plate amplified. The amplified phage were then rescreened with the magnetic beads and plated out. Fourteen phage, comprising 9 different nucleotide sequences, were isolated based on their high affinity to the 7E11-C5 monoclonal antibody.

The amino acid sequences of the binding domains of TSARs encoded by the 7E11-C5 binding phage are presented in Table 1.

prediction was that the TSAR with the highest affinity for the antibody would still bind effectively to wells coated with lower amounts of antibody. The TSARs that bound the best were 9-1, 9-3, 9-5, and 12-1. These TSARs all have Y as the second amino acid in the motif. The next class of TSARs bound ~2-fold less well; as represented by 12-2, which also had Y as the second amino acid. Three TSARs bound 5–10 fold less well than the best binders as represented by 9-2, 9-4, and 12-4; their inserts had W or H at the second position of the motif. Finally, TSAR 12-3 bound 50-fold less well than the best binders; this TSAR has I and R in the second and sixth positions, respectively. Thus, it seems that the 7E11-C5 epitope can be mimicked by a linear peptide sequence that has both variant and invariant residues.

The antigen recognized by the 7E11-C5 monoclonal antibody is highly expressed in the LNCaP human prostate carcinoma cell line (ATCC # CRL 1740). The ability of three of the TSARs peptides illustrated in Table 1, i.e., TSARs

TABLE 1

TSARS BINDING 7E11-C5 ANTIBODY

| No. Isolated | Amino Acid Sequence[1] | | | Designation Name | SEQ ID NO |
|---|---|---|---|---|---|
| 1 | SSCAYARYVPLLLLLYANPG | MYSRLH | SPAVRPLTQSSA | 7E11.9-1 | 22 |
| 1 | SVQFKSISSRSMDDVVKDPGPKPA | MWKMLH | SKNPFTLS | 7E11.9-2 | 23 |
| 1 | FDHTYSGPVCVKNGGLVSPGVLS | MYNRLH | SDGGPSLAS | 7E11.9-3 | 24 |
| 3 | TVAT | MHDTLH | SAPGSGNLPGSYDIKPIFKASGALHSTX[2] | 7E11.9-4 | 25 |
| 1 | IDMPETAST | MYNMLH | RNEPGGRKLSPPANDMPPALLKR | 7E11.9-5 | 26 |
| 1 | RLGNVWRVEGGG | MYQQLH | HNFPX[2] | 7E11.12-1 | 27 |
| 3 | RDSAVENPSVGGEIP | MYRYLH | QR | 7311.12-2 | 28 |
| 1 | PVQKEYGFFMSGAS | MIRLLR | ETP | 7E11.12-3 | 29 |
| 2 | QKGGPGLLLYGGDS | MWITLH | EPG | 7E11.12-4 | 30 |

[1]The non-variable amino acids at the $NH_2$ and COOH terminal residues are not shown.
[2]X represents any amino acid due to an ambiguity in the nucleotide sequence.

All nine 7E11-C5 binding TSARs identified bound to the 7E11-C5 monoclonal antibody at least 1,000–10,000 times more strongly than to an irrelevant mouse monoclonal antibody of the same isotype, i.e., the B72.3 monoclonal antibody described in U.S. Pat. Nos. 4,522,918 and 4,612,282 or to bovine serum albumin (BSA). In fact, none of the 7E11-C5 binding TSARs bound to any other monoclonal antibody tested including the C46 monoclonal antibody which recognizes CEA antigen (see, Rosenstraus et al., 1990, Cancer Immunol. Immunother. 32: 207–213).

As shown in Table 1, the nine 7E11-C5 binding TSARs appear to share a linear consensus motif of six amino acids, i.e., M(Y/W/H/I)XXL(H/R) where X is apparently any amino acid. Recently, the sequence of a protein expressed in prostate carcinoma cells, recognized by the 7E11-C5 MAb has been published (Israeli et al., 1993, Cancer Res. 53: 227–230). There are two places in the sequence of the protein, i.e., residues x–x' and y–y', where the sequence matches the linear consensus motif identified in the 7E11-C5 binding TSARs. Thus, the method of the present invention has identified a linear consensus motif that can be used to identify the epitope recognized by 7E11-C5 in the naturally occurring protein. Confirmation of the epitope will involve synthesis of the exact sequences from the protein and showing that either or both bind to 7E11-C5 or inhibit the binding of 7E11-C5 to the antigen.

The relative affinity of the different 7E11-C5 binding TSARs for the 7E11-C5 antibody was compared. Microtiter plates were coated with differing amounts of the antibody (i.e., 0, 4, 20, 100 and 500 ng) prior to phage binding. Our designated 7E11.9-1 (SEQ ID NO 22), 7E11.9-5 (SEQ ID NO 26) and 7E11.12-2 (SEQ ID NO 28) to recognize the antigen binding site of the 7E11-C5 monoclonal antibody was evaluated in a competitive binding ELISA assay using an LNCaP cell lysate as "capture" antigen as follows:

Each well of a polyvinylchloride 96-well ELISA plate (Cooke, Alexandria, Va.) was coated with an LNCaP human prostate carcinoma cell (ATCC # CRL 1740) lysate. Lysates were prepared by harvesting confluent LNCaP cell cultures, resuspending cells in 4 volumes of 1 mM $MgCl_2$ for 5 minutes, mixing with 2 μg of DNase (Boehringer Mannheim, Indianapolis, Ind.) and homogenizing using 40 strokes in a Dounce homogenizer (Wheaton, Millville, N.J.). LNCaP lysate (50 μl per well of a 1:50 dilution in 0.1×PBS [Dulbecco's pH 7.2, JRH, Denver, Pa.]) was air dried overnight at 37° C. onto wells of the ELISA plate. ELISA plates were blocked with 150 μl/well of 1% BSA (Pentex Fraction V, Miles, Kankakee, Ill.) in PBS for 60 minutes at room temperature.

The competitive assays were performed by pre-incubating the highly concentrated TSAR producing phage ($6.3 \times 10^7$ to $6.3 \times 10^{11}$ pfu) with the 7E11-C5 monoclonal antibody (30 ng/ml) (1:1) for 1 hr at room temperature, prior to addition to the LNCaP antigen-coated ELISA plate for 1 hr at room temperature. The blank control consisted of blocking solution in the absence of primary antibody. 7E11-C5 monoclonal antibody pre-incubated with buffer without any phage (MAb) was the positive control. The expression vector m663 phage was also employed as a non-specific phage control.

Plates were washed 4 times with 0.05% Tween-20 in PBS. Bound monoclonal antibody 7E11-C5 was detected by: (1)

incubating with 50 μl/well of anti-mouse IgG₁-HRP (Fisher Biotech, Orangeburg, N.Y.) diluted to 0.4 ng/ml in 1% BSA-PBS, for 60 minutes at room temperature; (2) washing plates 6 times with 0.05% Tween-20 in PBS; and (3) adding 100 μl/well ABTS substrate [200 μl ABTS, (Boehringer Mannheim), 10 ml citrate buffer (pH 4), 10 μl $H_2O_2$]. Optical density of the reactions products was determined by endpoint analysis on a Multiscan plate reader (Molecular Devices, Menlo Park, Calif.). The competitive inhibition (%) was determined by comparing the reactivity of the positive control to the test samples. The results obtained using the 7E11.9-5 and 7E11.12-3 phages are presented in FIG. 10.

As shown in FIG. 10, phage producing TSARs designated 7E11.9-5 and 7E11.12-1 inhibited the binding of 7E11-C5 monoclonal antibody to its antigen, in a dose dependent fashion. The phage producing the TSAR designated 7E11.9-1 also inhibited 7E11-C5 monoclonal antibody binding (data not shown). The TSAR 7E11.12-3 phage has approximately a 50-fold lower relative affinity for the 7E11-C5 monoclonal antibody than the TSAR 7E11.9-5 phage, and this is reflected in a higher phage concentration necessary to inhibit 50% of the antibody binding: $IC_{50}$ of $3.5 \times 10^{11}$ compared to $IC_{50}$ of $1.7 \times 10^{10}$. M663 phage, containing the c-myc epitope recognized by MAb 9E10, did not inhibit binding: which demonstrates that inhibition occurs only in the presence of the correct peptide on the phage surface.

In addition, a peptide corresponding to a portion of one of the 7E11-C5 binding TSARs, i.e., TSAR 7E11.9-1 (SEQ ID NO 22) having the amino acid sequence LYANPGMYSR-LHSPA (SEQ ID NO 31) was synthesized using an Applied Biosystems synthesizer (Foster City, Calif.) and purified by HPLC. In another series of experiments, it was demonstrated that the peptide having SEQ ID NO 31 retains substantially the same activity as the original TSAR, expressed as a pill fusion protein, from which it was derived.

For the experiments described below, the synthetic TSAR-based peptide designated SEQ ID NO 31 was prepared as the purified (reverse phase HPLC) amide form.

In one set of experiments, the ability of SEQ ID NO 31 (amide form) to recognize the antigen binding site of the 7E11-C5 monoclonal antibody was evaluated in a competitive binding ELISA using a LNCaP extract as immobilized antigen essentially as described above herein. The TSAR-based peptide (SEQ ID NO 31) concentration ranged from 1.75 to 1130 nM. The concentration of the 7E11-C5 monoclonal antibody was kept at 30 ng/ml (0.2 nM). The peptides were pre-incubated with the 7E11-C5 monoclonal antibody for 1 hr at room temperature prior to the addition to the antigen coated ELISA plate. Two additional control peptides (amide form) having the following amino acid sequences: RGD-21: $NH_2$-PSYYRGDAGPSYYRGDAG-$CONH_2$ (SEQ ID NO 32) and CYT-379: $NH_2$-SYGRGDVRGDFKCTCCA-$CONH_2$ (SEQ ID NO 33) were also evaluated. Herein these control peptides are referred to as Control Peptide 1 and Control Peptide 2. The ability of SEQ ID NO 31 (amide form) and the two control peptides, Control Peptide 1 and Control Peptide 2, to competitively inhibit another monoclonal antibody, i.e., B139 obtained from Jeffrey Schlom, National Cancer Institute, NIH, Bethesda, Md., was also evaluated. The B139 monoclonal antibody, which is a murine $IgG_1$ monoclonal antibody that reacts with all human epithelial cells, recognizes a different antigen in the LNCaP extract from that recognized by the 7E11-C5 antibody. The control B139 monoclonal antibody was used at a concentration of 9 ng/ml. The results obtained are illustrated in FIG. 11.

As shown in FIG. 11, SEQ ID NO 31 (amide form) effectively competitively inhibited the binding of the 7E11-C5 monoclonal antibody to LNCaP extract with an $IC_{50}$ of about 160 nM, corresponding to a molar ratio of about 400:1 of peptide to monovalent binding site on the antibody. Both the two control peptides, Control Peptide 1 and Control Peptide 2, did not effectively compete with the 7E11-C5 antibody. Moreover, neither SEQ ID NO 31 (amide form) nor either of Control Peptide 1 and Control Peptide 2 competitively inhibited the binding of the isotype-matched control B139 monoclonal antibody. Based on the results presented, it is clear that SEQ ID NO 31 (amide form) specifically recognizes the antigen binding site, and in fact, mimics the epitope, of the 7E11-C5 monoclonal antibody.

In still another set of experiments, the ability of SEQ ID NO 31 (amide form) to specifically bind to the 7E11-C5 monoclonal antibody, when its conformation was constrained by immobilization was evaluated as follows:

Peptides, diluted in 10% PBS (Dulbecco's, pH 7.2, Hazelton), were immobilized by adsorption on polyvinylchloride plates. SEQ ID NO 31 (amide form) was diluted in 10% PBS at 0.5, 5, 50 or 500 /μg/ml. Control peptide 2 in 10% PBS at the same range of concentrations served as the control. A 50 μl volume of the test or control peptide solution was added to each well and incubated overnight at 4° C. The peptide solution was removed and 10% BSA-PBS was added as blocking solution. Either the 7E11-C5 monoclonal antibody or control B139 monoclonal antibody was added at concentrations ranging from 1.7 to 10,000 ng/ml and the plates were incubated for 1 hr at room temperature. Bound 7E11-C5 monoclonal antibody was detected with anti-mouse $IgG_1$-HRP as described above herein.

Results of the binding assay obtained when the concentration of immobilized SEQ ID NO 31 (amide form) was varied from 0.5 μg/ml to 500 μg/ml are illustrated in FIG. 12. Dose dependent binding of 7E11-C5 was observed at all peptide concentrations tested (FIG. 12). As also shown in FIG. 12, optimal antibody binding to SEQ ID NO 31 (amide form) occurred on plates coated with a 5 μg/ml solution of SEQ ID NO 31 (amide form).

Specificity of the immobilized SEQ ID NO 31 (amide form) for the 7E11-C5 monoclonal antibody was also evaluated by contacting the wells of ELISA plates having SEQ ID NO 31 (amide form) immobilized thereon, by incubation with 50 μl of peptide at 5 μg/ml overnight at 40° C. with either the 7E11-C5 antibody or the non-relevant B139 antibody (control antibody). Results presented in FIG. 13, demonstrate that 7E11-C5 antibody specifically bound to the SEQ ID NO 31 (amide form) coated plates, whereas, the B139 antibody failed to bind to the SEQ ID NO 31 (amide form)-coated plates.

Additionally, when immobilized on ELISA plates the irrelevant Control 1 and Control 2 peptides did not bind to either of the tested antibodies (data not shown).

Based on the results obtained, the 7E11-C5 binding TSARs and peptides comprising portions of such TSARs such as SEQ ID NO 31, for example, should be useful for the development of immunoreactivity assays and affinity chromatography of the 7E11-C5 antibody. As explained above, such TSAR compositions have been useful to elucidate the epitope, of the 7E11-C5 antigen and may also be useful to prepare mimetopes of such epitope useful, for example, in preparing a vaccine against prostate cancer for patients undergoing prostectomy or post-prostectomy since the relevant antigen is highly restricted to prostatic carcinoma and normal prostate.

7.3. IDENTIFICATION OF METAL BINDING TSARS

In another series of experiments, the TSAR-9 library was screened for expressed proteins/peptides having binding specificity for a metal ion as the ligand of choice including such as zinc, copper, nickel, etc.

In a particular group of experiments, a form of immobilized metal affinity chromatography (IMAC) was used in which iminodiacetic acid-sepharose serves to coordinate and immobilize $Zn^{+2}$ in a tridentate fashion and to present the remaining coordination sites for interaction with other ligands.

The TSAR-9 random peptide library was subjected to IMAC chromatography as follows: 0.5 ml bed volume iminodiacetic acid (IDA) Sepharose (Sigma Chemical Co.) columns were washed with 1 ml of sterile doubly distilled (dd) $H_2O$ charged with 5 ml of 10 mM $ZnCl_2$ in dd $H_2O$ followed by 3 ml sterile dd $H_2O$ and equilibrated with 10 ml 10 mM Tris-HCl, 150 mM NaCl, 0.1 % Tween-20, pH 7.5 (TI0NT) to prepare the Zn(II) IDA column. $10^{12}$ pfu of the TSAR-9 random peptide library were passed over the Zn(II) IDA column and washed with 10 ml T10NT. Bound phage were eluted with 500 µl 200 mM glycine-HCl, pH 2.2 and the pH was then neutralized with 500 µl 1M phosphate buffer, pH 7.5+1 ml T10NT. Eluted phage were subjected to two further rounds of selection and the resulting population was amplified by overnight growth on a lawn of *E. coli* DH5αF'.

Isolated phage expressing a Zn-binding TSAR were selected without bias, amplified overnight and the DNA-encoding the TSARs were sequenced.

The amino acid sequences of the binding domains of TSARs encoded by the zinc binding phage are presented in Table 2.

compositions, when considered without regard for position, exhibit striking biases. When compared to the amino acid composition of the input TSAR-9 library, the clones share a statistically significant abundance of histidine ($p<2\times10^{-17}$) and proline ($p<0.05$) residues, as well as a dearth of alanine ($p<0.008$), valine ($p<0.009$), leucine ($p<0.0003$), and cysteine ($p<0.00008$) residues. These biases must be attributed to the Zn(II)-IDA selection process, as the amino acid composition observed in the input TSAR-9 library served as the baseline for these calculations.

The most dramatic biases associated with the Zn(II)-IDA selected peptides are the 3.6-fold enrichment for histidine and 8.5-fold suppression of cysteine residues. While peptides displayed on randomly selected TSAR-9 clones contain an average of 1.73±1.44 (mean±standard deviation) histidine and 1.23±1.19 cysteine residues, those displayed on Zn(II)-IDA selected phage contain an average of 6.21±1.13 histidines and 0.16±0.50 cysteines. The importance of histidyl residues in metal coordination, both in vivo [Berg, 1988, Proc. Nat'l Acad. Sci. USA 85: 99–102 (Berg 1988)] and in the context of IMAC [Yip, et al., 1989, Anal. Biochem. 183: 159–171 (Yip)], has been well documented. Although cysteine residues participate in $Zn^{2+}$ coordination by proteins in vivo [Berg, 1990, Ann. Rev. Biophy. Biochem. 19: 405–421 (Berg 1990)], the observed paucity of cysteines is consistent with the low contribution of cysteines to peptide retention in IMAC, calculated by Yip. Arnold (1991, Biotechnol. 9: 151–156) has suggested that cysteines may not contribute to retention in IMAC because they tend, in the presence of metal ions, to oxidize and form disulfide bridges, rendering them unavailable for interaction with immobilized metal. While the absence of a selection for cysteine residues might by explained by such an effect, the dramatic suppression of cysteines requires further explanation. It is possible that disulfide bonds would tend to constrain peptides into conformations incompatible with stable interaction with Zn(II)-IDA.

TABLE 2

TSARS BINDING ZINC

| Amino Acid Sequence[1] | Designation Name | SEQ ID NO |
|---|---|---|
| T G L H T F A H G V S Y G Y F G I G P G H H S S E G D H I P I H T D V S H H | Zn1C7 | 34 |
| G V V S S E W A S K H Y N H H F H T P G F L V R H F C T P I S Q M D H K E T | Zn1C6 | 35 |
| G A Y G H R Y M G H P I L I N V Q D P G F Q I L S T H W E F N N R A S H H P | Zn1B7 | 36 |
| E K F D A A H G T D M Y F S S Q H Y P G H N N I P H H P R A E F F H G H T L | Zn1B6 | 37 |
| T T H Q H H V T F S T S A H N P F S P G H N Y G V R T Q L P A T S H T H I P | Zn1B11 | 38 |
| H E T W D Y Y H H N S F L P H D Y S P G I L S S H N V F R K E R R E V E N S | Zn1A9 | 39 |
| Y N L I A P S F H G G N D R A Q S V P G V H H H H P E S K A Y P Q L S Y G K | Zn1A8 | 40 |
| A H E P N S F G F V Q G A H D H N P P G T T S P S P H D W P N L H H W G I I | Zn1A7 | 41 |
| S S H Q H F P Y L N S R D P I R S H P G H P E H Q Y P Y G A G I S S N S P S | Zn1A11 | 42 |
| M G P S Y T D N G D G N R H D H Y V P G H P I P P N E L H R H T T I P E S L | Zn1Z1 | 43 |
| G P P G D G A H A D D H K H R W T H P G Y H S G Y M H S P L T L H T Q H S Q | Zn1Z3 | 44 |
| S S H D S I Y N F E F R E V N H H S P G N G L G G V S H T H H S N M S R L D | Zn1Z4 | 45 |
| Q P T I S P P D F N H R A S L N H L P G H N M S H S N S S G S L T L P A V H | Zn1Z5 | 46 |
| D A N G T S L S D E R M Y H H N V S P G F R H F Q G W T H D H D H A Y P H M | Zn1Z6 | 47 |
| G V P R V T T R F S D S I G Y H Y A P G P R A E H S V H H G T H D S H P N T | Zn1Z9 | 48 |
| Y D H H S Y N G D M H Y P G W P P L P G P H H F A P I D V T T H S H T Q P D | Zn1A1 | 49 |
| I D H H H H T F T T R N A P S Q P N P G P P Y F P H V H H R D S S S M S K R | Zn1A6 | 50 |
| H S Y H D V A T T K P G S H C M H N P G H P P P P N C H M A K A H S H N R I | Zn1A12 | 51 |
| A T E Q H Y W T Q Y H K P Y H P S V P G F H V K S V T E T T D H W E S R N G | Zn1B8 | 52 |

[1]The non-variable amino acids at the $NH_2$ and COOH terminal residues are not shown.

Table 2 presents the deduced amino acid sequences of the binding domains of the Zn(II)-binding TSARs. While the amino acid sequences of the TSAR peptides reveal no significant linear consensus motif, their amino acid Superficially, some aspects of the distribution of amino acids within the peptides expressed on Zn(II)-IDA selected phage appear non-random. To investigate this possibility, we performed a number of statistical tests, in which the observed number of amino acids of a specific class found at positions n+1, n+2, n+3, or n+4 (relative to histidine residues) were compared to the number expected assuming a random distribution. We detected no statistically significant biases in the distribution of histidine residues relative one another. Similarly, amino acids with aromatic side chains (phenylalanine, tyrosine, and tryptophan) as a group, residues with aliphatic side chains (glycine, alanine, valine, leucine, and isoleucine) as a group, and proline residues appear to be randomly distributed relative to histidine. Finally, no significant biases in the positional distribution of histidines within the random peptide are evident.

Based upon their differing characteristics, four of the TSARs listed in Table 2 were chosen for chromatographic characterization: Zn1A1, Zn1A6, Zn1A12, and Zn1B8 (SEQ ID NOs. 49, 50, 51, 52). TSARs were selected in an attempt to represent a range of abundances and distributions of histidine residues within the variant insert. Zn1A1 and Zn1A6 each possess seven histidines within their random peptide, while Zn1A12 and Zn1B8 contain eight and five histidines, respectively. Zn1A12 and Zn1B8 both contain well distributed histidines within their unpredicted peptide, while the histidines in ZnA1 and ZnA6 are relatively and exceptionally clustered, respectively.

To quantitate the relative binding of the Zn(II)-IDA selected TSARs, each TSAR encoding phage was chromatographed over Zn(II)-IDA. Three fractions were collected and titered for phage: wash (unbound), elution (bound, eluted), and column (bound, not eluted). When fractionated in this manner, each TSAR binding domain consistently displayed at least a four log enrichment over non-selected phage clones (data not shown). Furthermore, each clone exhibited a consistent degree of retention, which ranged from 15% (for Zn1A1) to 85% (for Zn 1B8) of recovered phage.

As Zn1B8 possesses the fewest histidines within its binding domain, the absolute number of histidines does not appear to be the only determinant of efficiency of binding to Zn(II)-IDA. Sequences which separate histidyl residues must also contribute to retention, either directly (by coordinating metal) or indirectly (by affecting histidine-metal interactions). Although a number of studies (Hemdan, et al., 1989, Proc. Nat'l Acad. Sci. USA 86: 1811–1815; Yip) have concluded that protein retention by IMAC is primarily determined by the number of surface histidines, other functional groups have been shown to contribute to binding (Yip).

Further, the experiments demonstrate that the TSARs with the most clustered distribution of histidines (Zn1A12 and Zn 1B8) exhibit the least retention by Zn(II)-IDA. This observation is consistent with the fact that no statistically significant positional bias of histidines relative to one another within the random peptide was detected. It seems reasonable that polyhistidine runs of length n would contribute less to binding than n histidines randomly dispersed within the unpredicted peptide, as the coordination geometry of adjacent histidyl residues would probably be less favored than separated histidyl residues.

The binding specificity of a number of the identified Zn-binding proteins was evaluated by chromatography using IDA columns charged with $Zn^{+2}$, $Cu^{+2}$ or $Ni^{+2}$. A particular Zn-binding phage ($1 \times 10^{11}$ pfu) in 1 ml of 100 mM Tris-HCl, 150 mM NaCl, 0.1% Tween-20, pH 7.5 (T100NT) was loaded onto a Zn(II)-, Cu(II)- or Ni(II)-IDA column and the columns were washed as described above, except that T100NT was substituted for T10NT. The columns were eluted with acid; $Zn^{+2}$(2 ml 100 mM $ZnCl_2$ in T100NT, pH 7.5), or imidazole (2 ml 100 mM imidazole in T100NT, pH 7.5). Three fractions were collected and titered for the presence of phage: the wash fraction (■), the elution fraction (▨) and the metal II-IDA column matrix resuspended in T10NT (□). Results obtained are shown in FIG. 14A and 14B.

As shown in FIG. 14A and 14B, the Zn-binding TSARs also bind to Cu(II)-IDA and much less well to Ni(II)-IDA. Further, as shown in FIG. 14B, the Zn-binding TSARs were not retained by the uncharged IDA-sepharose and were eluted with Zn(II) i.e., $ZnCl_2$ in T100NT, (pH 7.5).

The TSAR-9 library was screened for $Cu^{+2}$ and $Ni^{+2}$ binding TSARs as described above for $Zn^{+2}$ binding except that the IMAC was charged with $Cu^{+2}$ or $Ni^{+2}$.

Tables 3 and 4 present the amino acid sequences of the binding domains of copper ($Cu^{+2}$) binding TSARs and nickel ($Ni^{+2}$) binding TSARs, respectively.

TABLE 3

TSARs BINDING $Cu^{+2}$

| | Designation | |
|---|---|---|
| Amino Acid Sequence[1] | Name | SEQ ID NO |
| S V K A H H M E R P L N N F D G P P P G D R V V G C H L F R V T S G Q C R H | CuB9F | 53 |
| F A V G S T N V V M V E H N S D H N P G H T V S C S A T Q G H I C D D N T R | CuB8F | 54 |
| E L V I N L A S I V S A G S R N I G P G R L S G L H Y G P P E Q Y F R H S P | CuB11F | 55 |
| Y L A T S R F P L T Q S V A L T H S P G S S S H P L T S Y R W D A H S N H P | CuA9F | 56 |
| D Y S V L V T S L R I T G S L Y C P P G P R Y N F H D N H G R P C G S R S C | CuA8F | 57 |
| Y F A V M C D E G R N T R V C H H S P G W L T H G R Y S V S A T D D L S G S | CuA11F | 58 |
| C H I T C K D C T G E H H S V Y C T P G I D S S N T E P Q A S M H Y F N P H | CuA10F | 59 |

[1]The non-variable amino acids at the $NH_2$ and COOH terminal residues are not shown.

TABLE 4

TSARs BINDING Ni$^{+2}$

| | Designation | |
|---|---|---|
| Amino Acid Sequence[1] | Name | SEQ ID NO |
| Y N G K D H Q L P M L T P S H A T G P G S C W F N Q T T V P T S D I E G H | HNIB1F | 60 |
| H E S D R H D A I S S V G R S L D V P G T H R D W A S H Y I H F I T G H N F | NIA6F | 61 |
| E S I R Y Y T S R Q D S Y R S N L A P G T Y N I V D Y N T S L H T L T H T T | NIA3F | 62 |
| S P I C H H S G Q F V Y D H P N H S P G P M K S L F Q H H C R N N E L P L N | NIA1F | 63 |

The non-variable amino acids at the NH$_2$ and COOH terminal residues are not shown.

7.4. IDENTIFICATION OF TSARs BINDING A POLYCLONAL ANTIBODY

In another series of experiments, the TSAR-9 library was screened for expressed proteins/peptides having binding specificity for a polyclonal antibody, i.e., a goat anti-mouse Fc antibody (GAM) using the screening method d The T above in Section 7.1.

The TSAR-9 library was screened with the polyclonal antibody as follows. An affinity purified goat anti-mouse Fc polyclonal antibody (GAM) was obtained commercially from Sigma Chemical Co., (St. Louis, Mo.) was incubated with magnetic beads (Advanced Magnetics, Cambridge, Mass.). GAM-coated magnetic beads were incubated with the TSAR-9 phage for 1–2 hr with tumbling. Phage expressing a TSAR having binding affinity for GAM were isolated by removing bound phage-GAM bead complexes using a strong magnet. The bound phage were recovered from the bead complexes by acid elution, i.e., 50 μl 200 mM glycine HCl, pH 2.2, followed by 100 μl 1M Na$_2$HPO$_4$, pH 7.0.

The deduced amino acid sequences of the GAM binding TSARs were determined by DNA sequencing. The amino acid sequences of the binding domain of TSARs encoded by the GAM binding phage are presented in Table 5. All the GAM binding TSARs presented in Table 5 failed to bind to magnetic beads coated with other goat anti-mouse polyclonal antibodies tested (data not shown). Such results suggest that polyclonal antibodies vary in specificity from one preparation to another. Thus, when the TSAR is intended to be useful for binding a polyclonal antibody, such as serum from autoimmune patients, screening should be done on an individual patient basis which can be efficiently accomplished using the rapid methods and the libraries of the invention.

that this sequence is present within the Fc regions of the mouse γ-2a and γ-3 heavy polypeptide chains (RTISKP; aa 216–221). Thus, it appears that one of the major targets of the affinity-purified goat polyclonal antibody, as mapped by this system, is a discrete region in the mouse immunoglobulin heavy chain. Interestingly, this region differs among vertebrate species.

The remaining GAM binding TSAR presented in Table 5 differs from the-other three GAM binding TSARs; yet it still binds to the goat anti-mouse Ig beads effectively. It is unclear what aspect of its insert sequence (i.e., primary, secondary) is responsible for its binding. Of note, the primary sequence of this TSAR does not match any mouse immunoglobulin sequence examined.

7.5. IDENTIFICATION OF TSARs BINDING C46 ANTIBODY

In still another series of experiments, the TSAR-9 library was screened for expressed proteins/peptides having binding specificity for an anti-carcinoembryonic monoclonal antibody i.e., anti-CEA C46 antibody, (see, Rosenstraus et al., 1990, Cancer Immunol. Immunother. 32: 207–213).

The TSAR-9 library was screened for C46 monoclonal antibody binding proteins/peptides as described above in Section 7.2.

Two recombinant phage encoding TSARs having specific binding affinity for the C46 monoclonal antibody have been consistently isolated. These phage did not bind to the anti-prostate carcinoma antibody 7E11-C5 or to an 18F7 antibody, a monoclonal antibody that recognizes the Sm antigen associated with a mouse model of the autoimmune disease systemic lupus erythematosus (see Section 7.6,

TABLE 5

GAM BINDING TSARs

| | | Designation | |
|---|---|---|---|
| No. Isolated | Amino Acid Sequence[1] | Name | SEQ ID NO |
| 17 | DVDMGTIFNTIANNITSRPGVSWGGST RTITKP KGAVA | GAM. 9-1 | 64 |
| 7 | QTAGQPG RTLSKP PIPNTPGPREPSLLHSMPHLPNLTA | GAM. 9-3 | 65 |
| 4 | V RTISKP VAREGWTRDTVPGPATSIVEKRFHLIGVNAQ | GAM. 9-2 | 66 |
| 1 | KGASFYPQCGGECQIYRVPGDHLPLFSLHRTGTPRHDS | GAM. 9-4 | 67 |

[1]The nonvariable amino acids at the NH$_2$ and COOH terminal residues are not shown.

Inspection of the TSAR sequences presented in Table 5 suggests a consensus among three of the GAM binding TSARs: RT(I/L)(S/T)KP. Examination of GenBank revealed infra). The amino acid sequences of the binding domains of TSARs encoded by the C46 binding phage are presented in Table 6.

TABLE 6

TSARs BINDING C46

| No. | | Designation | |
|---|---|---|---|
| Isolated | Amino Acid Sequence[1] | Name | SEQ ID NO |
| 1, 2 | NAVRVDSGYPPNPNTFHLPGCIDVLSSGCRLFSAHSEY | C46.9-1 | 68 |
| 6, 4 | CNFRGQCVSAPQTSNSKSPGWDTTWHDFRKEQFYNLTS | C46.9-2 | 69 |

[1]The non-variable amino acids at the NH$_2$ and COOH terminal residues are not shown.

The amino acid sequences of the two C46 binding TSARs identified have little to no apparent similarity to each other. When compared to the sequence of human CEA published by Barnett et al., 1988, Genomics 3: 59–66, there was little to no identity noticed with SEQ ID NO 69. On the other hand, a short region of SEQ ID NO 68, i.e., IDVL located at amino acid residues 22–25, was homologous to a short region on the CEA protein, i.e., LDVL at amino acid residues 586–590. Nevertheless, in view of the fact that such a 4 amino acid-long motif should have been isolated more frequently from the TSAR library, it appears that the epitope recognized by the C46 antibody may not be simple.

The ability of the C46 binding TSARs to recognize the antigen binding site of the C46 antibody was assessed using an ELISA assay as follows:

Microtiter dish wells were coated with 50 μl of the C46 monoclonal antibody (5 μg/ml in 100 mM NaHCO$_3$, pH 8.5) for 2 hr at 4° C. To the wells, 50 μl of BSA (1mg/ml in 100 mM NaHCO$_3$, pH 8.5) were added and the wells incubated for 30 min. at room temperature. The wells were washed (5×) with PBS-0.5% Tween 20.

To each well was added either 25 μl of C46-binding phage (C46.9-1 or C46.9-2) and increasing amounts of highly purified CEA (1, 25, 250, 2500 ng) (Scripps Clinic). After 2 hr incubation at room temperature, the wells were washed (10×) with PBS-0.5% Tween 20. 25 μl of 200 mM glycine-HCl (pH 2.2) were then added to the wells and they were incubated at room temperature for 5 min. The liquid was then transferred to new microtiter dish wells that contained 50 μl of 1M NaHPO$_4$. The contents of the well were then serially diluted and aliquots were plated to count plaques. The results are presented in FIG. 15.

As demonstrated in FIG. 15, CEA competes effectively with both of the C46 binding TSARs for binding to the C46 antibody.

7.6. IDENTIFICATION OF TSARs BINDING ANTI-Sm ANTIBODY

In yet another series of experiments, the TSAR-9 and TSAR-12 libraries were screened for expressed proteins/peptides having binding specificity for one of two monoclonal antibodies which recognize the SmB protein of the Sm antigen associated with a mouse model of the autoimmune disease systemic lupus erythematosus, i e., the 18F7 and 22G-12 antibodies (obtained as gifts from Debra Bloom and Steve Clark, University of North Carolina, Chapel Hill, N.C.) using an ELISA assay in a microtiter plate format as follows.

50 μl of the Sm antibody diluted to 1 μg/ml in 100 mM NaHCO$_3$, pH 8.5 was placed into wells of microtiter plates (Corning). The plates were incubated overnight at 4° C. 100 μl of BSA solution (1 mg/ml, in 100 mM NaHCO$_3$, pH 8.5) was added and the plates were incubated at room temperature for 1 hr. The microtiter plates were emptied and the wells washed carefully with PBS-0.5% Tween 20, using a squeeze bottle.

Plates were washed five times to remove unbound antibodies. Then 25 μl of phage solution was introduced into each well and the plates were incubated at room temperature for 1–2 hrs. The contents of microtiter plates were removed and the wells filled carefully with PBS-0.5% Tween 20, using a squeeze bottle. The plates were washed five times to remove unbound phage. The plates were incubated with wash solution for 20 minutes at room temperature to allow bound phage with rapid dissociation constants to be released. The wells were then washed five more times to remove any remaining unbound phage.

The phage bound to the wells were recovered by elution with a pH change. Fifty microliters of 50 mM glycine HCl (pH 2.2), 10 mg/ml BSA solution were added to washed wells to denature proteins and release bound phage. After 5–10 minutes, the contents were then transferred into clean tubes, and 100 μl 1 M Tris-HCl (pH 7.5) or 1M NaH$_2$PO$_4$ (pH 7) was added to neutralize the pH of the phage sample. The phage were then diluted $10^{-3}$ to $10^{-6}$ and aliquots plated with *E. coli* DH5αF' cells to determine the number of plaque forming units of the sample. In certain cases, the platings were conducted in the presence of XGal and IPTG for color discrimination of plaques (i.e., lacZ$^+$ plaques are blue, lacZ$^-$ plaques are white). The titer of the input samples was also determined for comparison (dilutions were generally $10^{-6}$ to $10^{-9}$).

Successful screening experiments have generally involved 3 rounds of serial screening. Serial screening was conducted in the following manner. First, the library was screened and the recovered phage rescreened immediately. Second, the phage that were recovered after the second round were plate amplified according to Maniatis. The phage were eluted into SMG, by overlaying the plates with ~5 ml of SMG and incubating the plates at 4° C. overnight. Third, a small aliquot was then taken from the plate and rescreened. The recovered phage were then plated at a low density to yield isolated plaques for individual analysis.

The individual plaques were picked with a toothpick and used to inoculate cultures of *E. coli* F' cells in 2XYT. After overnight culture at 37° C., the cultures were then spun down by centrifugation. The liquid supernatant was transferred to a clean tube and saved as the phage stock. Generally, it has a titer of $10^{12}$ pfu/ml that is stable at 4° C. Individual phage aliquots were then retested for their binding to the antibody conjugated ELISA plates and their lack of binding to other plate wells (i.e., BSA coated microtiter wells, or wells conjugated with a different control antibody).

The amino acid sequences of the binding domain of a number of the TSARs encoded by the Anti-Sm 18F7 antibody binding phage are presented in Table 7. The amino acid sequences of the binding domain of a number of TSARs encoded by the anti-Sm 22G-12 antibody binding phage are presented Table 8.

mation. The amino acid sequences of the Anti-Sm 22G12 binding TSARs presented in Table 8 reveal a motif E(V/L/R)(N/F/N)RYD and also non-motif sequences.

TABLE 7

TSARS BINDING ANTI-Sm ANTIBODY (18F7)

| | | | Designation | |
|---|---|---|---|---|
| No. Isolated | Amino Acid Sequence[1] | | Name | SEQ ID NO |
| 2 | G DGVP | LFNNSTHKITMLNPGHDTRMKTDFVNKKSVYSP | Sm.9-1 | 77 |
| 1 | TFKPDLKSNFAGSSASPNPGAWNGLRPRPV DGVP | SAVD | Sm.9-8 | 78 |
| 2 | HPACMGFSHPYGPTNCLSPGEV NKNVP | SLPITPDRESP | Sm.9-2 | 70 |
| 6 | SQVPTIDAFSVGMGKDDHPGMISEPSF NLRVP | HIDKFA | Sm.9-3 | 71 |
| 2 | PGEQSNL NTRVK | EGNWSSS[2] | Sm.9-4 | 72 |
| 1 | AYGTVCCSGMFTYSNSPRPGVNE NRRVP | VGDKGNNPDL | Sm.9-9 | 73 |
| 1 | TSPACASGSTHGALTDCWPGFSY NTRVP | YISQVETNAX | Sm.9-10 | 74 |
| 1 | YGFSNTMMAHGTHVYFSPPGFTLVVPISY NSRVP | RADA | Sm.9-11 | 75 |
| 2 | VRDADHTVFDATYCSSSAPGSPSHSNQML LNPHIL | RPC | Sm.9-7 | 83 |
| 1 | TMRTDWGFD LNPYIL | SPPGLSRTDFGPTEFRQNDAKK | Sm.9-17 | 87 |
| 1 | SNEHFRDRVSISKIHISSPGYAN LNPHLA | HKMKGQAH | Sm.9-16 | 79 |
| 1 | AFGREICIDFMHPCSRTRPGHDFSEKPNGSKDPQISFS | | Sm.9-5 | 81 |
| 4 | SDGMHCPHAFCNEHYHAPPGPHMLSDLFPGREKPPYTP | | Sm.9-6 | 82 |
| 1 | GPVDVHVALSVSHNSSKHPGTAPFTEMHSPLFDNPHHT | | Sm.9-12 | 84 |
| 1 | ADSHMGXWQYYRWWMRVGPGRWGSTPVLFRPEFDREWF | | Sm.9-13 | 85 |
| | RYNEPVYLYQPSVDQKGIPGPYLTLVHY NNRVP LTASI | | Sm.9-18 | 76 |
| | YLPWSKSFSPSQYTSMINPGHNSFSSQDTLYFERVAPH | | Sm.9-15 | 80 |
| | DPLLRDEINNKPGGDFYLPGFLWPWNYNFHSVHTQRPS | | Sm.9-14 | 86 |
| | GRTWHNISTFHPAHNSEGPGYIAFLNPFSETYVSSGSS | | Sm.9-19 | 88 |
| | PAEGGDEAGRGGATCRQKLRIAC | | Sm.12-1 | 89 |
| | GNDRHIGENRCGVWWREPECGAT | | Sm.12-2 | 90 |
| | GKLGSWRHAXXVCPTIP | | Sm.12-3 | 91 |
| | DSCSIAWFXACGEIPVP | | Sm.12-4 | 92 |
| | DVPDVMGARCGGAXRGWPELLRP | | Sm.12-5 | 93 |

[1]The nonvariable amino acids at the NH$_2$ and COOH terminal residues are not shown.
[2]This TSAR is not full length. This truncation is likely due to recombination in vivo or to the occurrence of an internal Xba I site in the cloned oligonucleotide fragment.
[3]X refers to unidentified amino acid residues due to ambiguities in the nucleotide sequences determined.

TABLE 8

TSARS BINDING ANTI-Sm ANTIBODY (22G12)

| | Designation | |
|---|---|---|
| Amino Acid Sequence[1] | Name | SEQ ID NO |
| VRLLDILSPEQLSLDDVSPGLP EVNRYP SKLPPPNRLG | 22G12.9-4 | 94 |
| TEALGDSGKKGGGVPSGP ELFRYP | 22G12.12-4 | 95 |
| VDPSTPNTLTDYYYMLSGPGATSFDG ERNRYP IVSTQH | 22G12.9-1 | 96 |
| YYPVYGSMRRLADYYSNGPGPECVRHQCTDEHRKAIDK | 22G12.9-2 | 97 |
| EYKARSSFVVMTGAEGNSPGCDVDRHCPYHHSYWTESI | 22G12.9-3 | 98 |
| DQASYFLDRWGGDGWSFTPTPPM | 22G12.12-1 | 99 |
| SLFFRPVWETSGECFQLFQPPPG | 22G12.12-2 | 100 |
| NGGRGCPVERCGDSVTGRAYDAI | 22G12.12-3 | 101 |
| MGGTYWEDRWGGVTLXPQXRETP | 22G12.12-5 | 102 |

[1]The non-variable amino acids at the NH$_2$ and COOH terminal residues are not shown.

The amino acid sequences of the Anti-Sm 18F7 binding TSARs presented in Tables 7 and 8 reveal no major shared sequences or similarity to the major Sm antigens (i.e., proteins B and D) except for the sequence RVP in the 5B protein. Nevertheless, there are motifs, i.e., DGVP, NXRVP, LNPHIL, that seem to be present in several of the phages encoding the TSARs. Non-motif sequences were also isolated. These preliminary data lead us to suspect that the antibody may be recognizing a discontinuous epitope or that the different motifs can adopt the same or a similar conformation.

7.7. IDENTIFICATION OF TSARs BINDING STREPTAVIDIN

In another series of experiments, the TSAR-9 and TSAR-12 libraries were screened for expressed proteins/peptides having binding specificity for streptavidin (SA). Phage were isolated from the library that bound to SA-coated magnetic beads (Advanced Magnetics, Cambridge, Mass.). After a 60 minutes incubation with tumbling, the phage-bead complexes were recovered with a strong magnet. Bound phage were recovered with 200 mM glycine-HCl (pH 2.2) and neutralized to pH 7.0, as described above in Section 7.1. After two additional rounds of purification, individual plaques were isolated. Most of the recovered phage bound >10⁵ times better to SA than non-binding phage (screened for phage that bind to SA).

Individual SA binding TSARs were recovered from 1to 20 times from the TSAR-9 library in two separate screening experiments each with two clones isolated. The amino acid sequences of the binding domains of TSARs encoded by the SA binding phage isolated from the TSAR-9 library are presented in Table 9. The corresponding sequences were not determined for the SA binding phage isolated from the TSAR-12 library. Table 9 shows that the binding phage fall into two classes. First, the majority of SA-binding peptides share the consensus motif HP(Q/M)θ (where "θ" signifies a nonpolar amino acid). The consensus sequence is similar to that determined with a random 15-amino acid phage library (Devlin, et al., 1990, Science 249: 404–406) and synthetic peptides on beads (Lam, et al., 1991, Nature 354: 82–84). The HP(Q/M)θ motif can be found at various positions throughout the length of the phage inserts. In addition, the motif was often (i.e., 69%) flanked on the COOH side by the amino acids P or D. Second, there is a minor class of SA-binding peptides that lacks any consensus sequence and has no apparent similarity with each other. Such class has not been reported by others describing smaller libraries screened for SA binding affinity.

Specificity of the binding of the identified proteins for streptavidin was investigated by evaluating inhibition of binding by biotin and by a number of biotin analogs, including diaminobiotin, immunobiotin, lipoic acid and imidazalidone. Four representative TSARs, pictured in Table 9, were evaluated, i.e., SA-1, -2, -4 and -14 (SEQ ID NOs. 116, 114, 104 and 117). Binding of each of the representative TSARs to streptavidin was completely inhibited by biotin and all the biotin analogs tested. $IC_{50}$ values of about 0.2, 3, 1050 and 5000 µl, respectively, were observed.

In addition, binding of the SA-binding TSARs to avidin was evaluated using the four representative SA-binders. None of the SA-binding TSARs were able to bind to native or non-glycosylated avidin (Accurate Chemicals, Westbury, N.Y.), even though SA and avidin are structurally similar proteins each having an affinity for biotin. Thus it appears that the binding domains are highly specific for the ligand of choice.

7.8. IDENTIFICATION OF TSARs BINDING POLYSTYRENE

In another experiment, it was observed that a number of the expressed proteins of the TSAR-12 library appeared to bind to magnetic beads alone. Accordingly, in another series of experiments, the TSAR-12 library was screened for expressed proteins/peptides having binding specificity for polystyrene. Two types of uncoated polystyrene magnetics

TABLE 9

TSARs BINDING SA

| No. Isolated | Amino Acid Sequence[1] | Designation Name | SEQ ID NO |
|---|---|---|---|
| 1 | HGMASQYFTCFHDSEPSSPGMFGWDPTTPTLP HPQV DE | SA.9-3 | 103 |
| 1 | IAHRVVAYNSLDSNPIWLPGEESSSVFGDY HPMF RAPV | SA.9-4 | 104 |
| 1 | HVPVFTRYNYAKPNDTDWPGGFVDSLSA HPQG PIAGGR | SA.9-6 | 105 |
| 2 | MTLGYDRASPAPNTSFSNPGLDFNPFTY HPQG PHQILQ | SA.9-11 | 106 |
| 2 | AGRAARDDDCRGHACMIIPGVSLFNSD HPMG AHPSIRR | SA.9-8 | 107 |
| 10 | DFSSFLTGTNAMAPFWPFPGSTYLLG HPMA PRDLQTSN | SA.9-10 | 108 |
| 3 | SASWKFNSSFGYPTGGIEPGPNC HPQA CPDVLAKSLSP | SA.9-13 | 109 |
| 2 | VSEMSSFSGCNTDH HPQG PGGRHDIMRSISESRGYGSL | SA.9-12 | 110 |
| 3 | EMLTLPLTSIPIPW HPQG PGYLYHKPPRGTDFRMLSSK. | SA.9-5 | 111 |
| 2, 1 | PYRFYHPYSHPR HPQG DVPGSSAEVFHTFPNTQGRNSR | SA.9-7 | 112 |
| 1 | ADYGTIGESPC HPQV DIC.PGALHHEFNEFFVGMSPEPS | SA.9-9 | 113 |
| 20, 3 | ARMAGLTE HPQG DIIDHHPGWVHDSKISPRNQDTYHSS | SA.9-2 | 114 |
| 1 | AHLFG HPQV GFDSIGSAFPGDIHCKQYKADSGLQSAAA | SA.9-15 | 115 |
| 9 | PDYDLMSSTCRFYGCSKMPGGVAVNGLFAVQGHSKYSS | SA.9-1 | 116 |
| 1 | TWDFTRSSLPAGDTSFTSPGSYSVMTRSCGISCVPAEV | SA.9-14 | 117 |

The non-variable amino acids at the $NH_2$ and COOH terminal residues are not shown.

Examination of the amino acid sequences of the SA binding TSARs illustrated in Table 9 shows that the proteins can be divided into two separate classes: (1) a group of thirteen proteins which share a consensus motif, i.e., HP(Q/M)(-), where—is a non-polar amino acid residue, ("motif" proteins); and (2) a small group of proteins which do not share such consensus motif ("non-motif" proteins). The motif is found at various positions throughout the length of the random oligonucleotide coding sequences. The non-motif proteins have no apparent similarity, with respect to amino acid sequence, either with each other or with the motif proteins.

To compare the relative binding of the phage to SA, several of the phage were converted to LacZ⁺ (blue) and mixed (1:1) with other LacZ⁻ (white) phage. The motif SA-binding TSARs appeared to bind equally well while the non-motif SA-binding TSARs bound about five fold better than motif SA-binding TSARs.

beads, i.e., Advanced Magnetics and Dynal, were used in a "panning" technique as described above. Protein-bead complexes were removed with a strong magnet and the bound phage were recovered as above.

In yet another series of experiments, the TSAR-12 library was screened for proteins having specificity for polystyrene using uncoated polystyrene microplates. Polystyrene-bead-binding phage were disassociated from the plates with acid denaturation.

The amino acid sequences of the binding domains of the polystyrene-binding TSARs are shown in Table 10. Most isolates were recovered only once. White there is no apparent linear motif, the peptides are rich in tryptophan, tyrisone and glycine, poor in arginine, valine and lysine and completely lack cysteine residues.

TABLE 10

TSARs BINDING POLYSTYRENE

| Amino Acid Sequence[1] | Designation Name | SEQ ID NO |
|---|---|---|
| S S R L A Y D H Y F P S W R S Y I F P G S N S S Y Y N N S W P T I T M E T N | SB.9-5 | 118 |
| P Y W M F Y G F D W R G G F P P S H Q I M D Q | SB.12-5 | 119 |
| D S W P L R I Y S G L S N Y Y H Y F P G S L V Y N M M Y P S H G E A P K G D | SB.9-9 | 120 |
| W G W A R G L G G G K G D A R H P S A P E A H | SB.12-2 | 121 |
| W M Q S W Y Y H W G G G E T F P I R R D S G G | SB.12-6 | 122 |
| H H G A M N R Y Y T W L W D N S R F P G R S Y L L S A P A T Q P E A S I S Q | SB.9-10 | 123 |
| L G F S G W Y W Q G L Y G L G S H D P G F I H E Q S P A E V A M E D T E Q S | SB.9-7 | 124 |
| R P Y L Y D P N E W H R Y Y S Y L L P G H S Y N V Q S W P D G L G | SB.9-6 | 125 |
| P W W W V S W V D A G G G S L A L P T Q P S D | SB.12-1 | 126 |
| I Y Y P F F V W G N Y A N G G L L S P G H V Y S S N F I P L Y M Q R E V S P | SB.9-4 | 127 |
| G W Q[2] S G W E W W I G G G N W T S N T T H | SB.12-4 | 128 |
| E I H G N L Y N W S P L L G Y S Y F P G I S P K H I S G E V L L G R L P Q V | SB.9-1 | 129 |
| Y T G W E T W Y S F D P F T H Y G G P G S R F D F V H D K S E D P I D R S Y | SB.9-2 | 130 |
| Q D L D H W S V W S M Y S T Y P T S P G L V P Y S W G Y G S P N S H T D K L | SB.9-3 | 131 |
| W W D P D I W F G W G G A H P P N L I Q P I S | SB.12-3 | 132 |
| Q T L I D F H D L H Y W G A Y Y G W P G I Y D E A S G S Q A V R H N M T H T | SB.9-8 | 133 |
| T Y D Y T Y D W S G L F W S P F T H P G .A H M T T H S P W A G H K P H A E T | SB.9-11 | 134 |

[1]The non-variable amino acids at the NH$_2$ and COOH terminal residues are not shown.
[2]Q residue encoded by a suppressed TAG codon.

As demonstrated in Table 10, a number of TSARs having binding affinity for polystyrene were identified. The polystyrene binding TSARs bind to the plastic either in the form of beads or plates; these TSARs do not bind to polyvinyl chloride or polypropylene.

7.9. IDENTIFICATION OF CALMODULIN BINDING TSARs

In yet another series of experiments, the TSAR-12 library was screened for expressed proteins/peptides having binding specificity for calmodulin (CaM).

In particular, the TSAR-12 library was screened three times in serial fashion for binding to CaM as follows:

ELISA plates were coated overnight at 4° C. with 5 µg/ml calmodulin in 100 mM NaH$_2$CO$_3$, (pH 8.5). To block non-specific binding of phage, 200 µl of 2 mg/ml BSA in 100 mM NaH$_2$CO$_3$, (pH 8.5) was added to each well and the plates were incubated at room temperature for 1 hr. After the wells were washed five times with PBS-0.5% Tween 20 to remove free calmodulin protein, 50 µl of phage (10$^{11}$ pfu/ml) was added for 2 hr incubation at room temperature. Prior to recovering the bound phage, the wells were washed ten times with PBS-0.5% Tween 20. The bound phage were eluted with 25 µl of 200 mM glycine-HCl, pH 2.2 and then the pH was neutralized with the addition of 50 µl of 100 mM NAPO$_4$ (pH 7.5). The recovered phage were rescreened immediately and the phage that bound to the ELISA plate the second time were plate amplified. The phage on the amplified plate were collected after 3 hr incubation with PBS and then rescreened a third time.

Three rounds of serial screening yielded phage isolates that encoded TSARs which bind CaM. Aliquots at each of the screening steps were mixed with m663 blue phage and screened simultaneously for binding to CaM coated ELISA plates. With each round of screening the yield of library recombinants (white) increased significantly. After the third round, eight isolates were grown in 2 ml cultures of *E. coli* DH5αF' cells in 2XYT overnight at 37° C. The phage in these cultures were then tested individually for their binding to CaM; seven of the eight phage were demonstrated to bind CaM. Moreover, the CaM binding phage do not bind BSA or polystyrene.

The CaM binding phage were also tested for their ability to bind CaM in the presence and absence of free calcium ions. More particularly, 10 µl of 100 mM CaCl$_2$ or 10 µl of 100 mM EGTA was added to the wells to provide conditions in which calcium ions were either present or absent. All seven CaM binding TSARs bound equally well in both treatments, suggesting that they bind calmodulin in a calcium-independent manner.

The oligonucleotides of the seven TSAR-encoding phages were sequenced and revealed to carry identical DNA inserts encoding the binding domain of the TSARs.

The deduced amino acid sequence (SEQ ID NO 135) of the binding domain of the CaM binding TSAR, designated CaM-12. 1, is shown in Table 11 below.

TABLE 11

CALMODULIN BINDING TSARs[1]

| V | P | R | W | I | E | D | S | L | R | G | G | A | A |
| R | A | Q | T | R | L | A | S | A | | | | | |

[1]The non-variable amino acids at the NH$_2$ and COOH terminal residues are not shown.

The TSAR-12 library was rescreened, using a slightly different approach to determine whether other members with affinity for CaM could be identified. To do this, an aliquot of the library was mixed with biotinylated CaM and bound phage were recovered with (streptavidin) SA-magnetic beads. To prevent the isolation of SA-binding phage from the TSAR library, excess free biotin was added to the bead complexes prior to washing. As free biotin binds very well to SA, it competed away the binding of all SA-binding phage in the libraries. The beads were washed ten times with PBS-0.5% Tween 20, using a strong magnet to recover the beads from the wash solution. The bound phage were eluted with 50 µl of 50 mM glycine-HCl, pH 2.2 and then the pH was neutralized with the addition of 100 µl of 100 mM NaPO$_4$ (pH 7.5). The recovered phage were rescreened immediately; the phage solution was mixed with biotinylated CaM and phage-CaM complexes were recovered with SA-magnetic beads.

The phage that bound the second time were plate amplified. The phage from the amplified plate were then screened for binding to ELISA plates coated with CaM. These phage were found to bind to CaM but not BSA coated wells. Phage recovered from the CaM coated wells were then plate amplified and screened a fourth time with CaM coated wells. The phage that were then grown recovered were grown as individual isolates. Forty-eight isolates were tested for binding to CaM coated wells and 47 appeared to bind. Nine of these phage were sequenced and all were discovered to have inserted synthesized oligonucleotides with an identical nucleotide sequence. This sequence matched that of TSAR CaM-12.1 (SEQ ID NO 135) shown above in Table 11. Thus, the phage expressing the TSAR CaM-12.1 was isolated repeatedly from two separate, different screening experiments.

The binding properties of the CaM-12.1 TSAR were further examined in several ways. First, the ability of CaM-12.1 phage to bind other calcium-binding proteins was tested. It failed to bind ELISA plate wells coated with parvalbumin or vitamin D calcium-binding protein (both from Sigma, St. Louis, Mo.). It also did not bind to the calmodulin-binding protein, calcineurin (Sigma, St. Louis, Mo.). Second, the ability of natural calmodulin binding peptides and proteins to compete for binding of the CaM-12.1 phage with CaM was tested. Preliminary experiments suggested that a peptide corresponding to the binding domain of CaM-dependent protein kinase (#208734; Calbiochem, San Diego, Calif.) and bee venom melittin (#444605; Calbiochem, San Diego, Calif.) could compete with CaM-binding TSAR CaM-12.1 to CaM. Third, the ability of a synthetic non-peptide CaM-antagonist, W7, (#681629; Calbiochem, San Diego, Calif.), was tested for its ability to compete for binding of CaM-12.1 to CaM. W7 appears to compete with CaM-12.1 for binding to CaM (results not shown). In summary, (1) CaM-12.1 binds CaM specifically, and not because it is a high-affinity $Ca^{2+}$-binding protein; (2) CaM-12.1 binds CaM at a site partially overlapping or influenced, by the binding sites of CaM-dependent protein kinase peptide, melittin and W7.

8. EXAMPLE: PHAGEMID VECTORS USEFUL FOR EXPRESSION OF TSAR LIBRARIES

Several phagemid vectors are described below which are useful for expression of TSAR libraries according to the present invention.

8.1. CONSTRUCTION OF VECTOR pDAF1

The vector pDAF1 is constructed as follows:

To create the phagemid vector pDAF1, a segment of the M13 gene III was transferred into the Bluescript II SK+ vector (GenBank #52328). This vector replicates autonomously in bacteria, has an ampicillin drug resistance marker, and the fl origin of replication which allows the vector under certain conditions to be replicated and packaged into M13 particles. These M13 viral particles would carry both wild-type pIII molecules encoded by helper phage and recombinant pIII molecules encoded by the phagemid. These phagemids express only one to two copies of the recombinant pIII molecule and have been termed monovalent display systems (See, Garrard et al., 1991, Biotechnol. 9: 1373–1377). Rather than express the entire gene III, this vector has a truncated form of gene III [See generally, Lowman et al., 1991 (Biochemistry 30: 10832–10838) which demonstrated that human growth hormone was more accessible to monoclonal antibodies when it was displayed at the $NH_2$-terminus of a truncated form of pIII protein than at the $NH_2$-terminus of the full-length form]. In the phagemid vector constructed here, the TSAR oligonucleotides are expressed at the mature terminus of a truncated pII molecule, which corresponds to amino acids 198 to 406 of the mature pIII molecules.

The preferred vector is pDAF, which encodes amino acids 198–406 of the pIII protein, a short polylinker within the pIII gene and the linker gly-gly-gly-ser between the polylinker and the pIII molecule. This plasmid expresses pIII from the promoter and utilizes the PelB leader sequence for direction of pIII's compartmentalization to the bacterial membrane for proper M13 viral assembly.

A pair of oligonucleotides were designed CGTTAC-GAATTCTTAAGACTCCTTATTACGCA (SEQ ID NO 136) and CGTTAGGATCCCCATTCGTTTCT-GAATATCAA (SEQ ID NO 137) to amplify a portion (aa 198–406) of the pIII Gene from M13mp8 DNA via PCR. Since these oligonucleotides carried Bam HI and Eco RI sites near the 5' termini, the PCR product was then digested with Bam HI and Eco RI, ligated with pBluescript II SK+ DNA digested with the same enzymes, and introduced into E. coli by transformation. After the recombinant was identified, an additional double-stranded DNA segment was cloned into it, encoding the PelB signal leader with an upstream ribosome binding site. This segment was prepared by PCR from E. coli DNA using the oligonucleotides GCGACGCGACGAGCTCGACTGCAAATTC-TATTTCAA (SEQ ID NO 138) and CTAATGTCTA-GAAAGCTTCTCGAGCCCTGCAGCTGCAC-CTGGGCCAT CGACTGG (SEQ ID NO 139). The termini of the PCR product introduced a short polylinker of Pst I, Xho I, Hind III, and Xba I sites into the vector. The Xho I and Xba I sites were positioned so that assembled TSAR oligonucleotides could be cloned and expressed in the same reading frame as in the phage vectors described above. The third and final segment of DNA introduced into the vector, encoded the linker sequence gly-gly-gly-gly-ser (SEQ ID NO 141) between the polylinker and gene III. This linker matches a repeated sequence motif of the pIII molecule and was included in the chimeric gene to create a swivel point separating the expressed peptide and the pIII protein molecule. This vector has been named pDAF1. FIG. 5A schematically illustrates the pDAF1 phagemid vector.

8.2. CONSTRUCTION OF VECTORS pDAF2 AND pDAF3

The vectors pDAF2 and pDAF3 are prepared from pDAF1 but differ from the parent vector in that each contains the c-myc encoding sequence at the NH2 and COOH terminal sides, respectively, of the polylinker of Pst I, Xho I, Hind III and Xba I restriction sites. FIGS. 5B and 5C schematically illustrate the phagemid vectors pDAF2 and pDAF3. The pDAF2 and pDAF3 vectors are constructed as shown schematically in FIG. 5D.

9. EXAMPLE: PLASMID VECTOR USEFUL FOR EXPRESSION OF TSAR LIBRARIES

9.1. THE INITIAL VECTOR pJG200

Plasmid pJG200 was the starting material that was modified to produce a general TSAR expression vector. The initial plasmid, pJG200, contained target cistrons that were fused in the correct reading frame to a marker peptide with a detectable activity via a piece of DNA that codes for a protease sensitive linker peptide [Germino and Bastia, 1984, Proc. Natl. Acad. Sci. USA 81: 4692; Germino et al., 1983, Proc. Natl. Acad. Sci. USA 80: 6848]. The promoter in the original vector pJG200 was the $P_R$ promoter of phage lambda. Adjacent to the promoter is the gene for the $C_1 857$ thermolabile repressor, followed by the ribosome-binding site and the AUG initiator triplet of the cro gene of phage lambda. Germino and Bastia inserted a fragment containing the triple helical region of the chicken pro-2 collagen gene into the Bam HI restriction site next to the ATG initiator, to produce a vector in which the collagen sequence was fused to the lacZ β-galactosidase gene sequence in the correct translational phase. A single Bam HI restriction site was regenerated and used to insert the plasmid R6K replication initiator protein coding sequence.

The plasmid pJG200 expressed the R6K replicator initiator protein as a hybrid fusion product following a temperature shift which inactivated the $C_1 857$ repressor and allowed transcription initiation from the $P_R$ promoter. Both the parent vector construct with the ATG initiator adjacent to and in frame with the collagen/β-galactosidase fusion (noninsert vector), and pJG200 containing the R6K replicator initiator protein joined in frame to the ATG initiator codon (5') and the collagen/β-galactosidase fusion (3') (insert vector), produced β-galactosidase activity in bacterial cells transformed with the plasmids. As a result, bacterial strains containing plasmids with inserts are not distinguishable from strains containing the parent vector with no insert.

9.2. REMOVAL OF THE $P_R, C_1 857$ REPRESSOR AND AMINO TERMINUS OF CRO

The first alteration to pJG200 according to this invention was the removal and replacement of the Eco RI-Bam HI fragment that contained the $P_R$ promoter, $C_1 857$ repressor and amino terminus of the cro protein which provided the ATG start site for the fusion proteins. An oligonucleotide linker was inserted to produce the p258 plasmid, which maintained the Eco RI site and also encoded the additional DNA sequences recognized by Nco I, Bgl II and Bam HI restriction endonucleases. This modification provided a new ATG start codon that was out of frame with the collagen/β-galactosidase fusion. As a result, there is no β-galactosidase activity in cells transformed with the p258 plasmid. In addition this modification removed the cro protein amino terminus so that any resultant recombinant fusion products inserted adjacent to the ATG start codon will not have cro encoded amino acids at their amino terminus. In contrast, recombinant proteins expressed from the original pJG200 vector all have cro encoded amino acids at their amino terminus.

9.3. ADDITION OF THE $P_{TAC}$ PROMOTER, SHINE DALGARNO SEQUENCE AND ATG CODON

In the second step of construction of a TSAR expression vector, a restriction fragment, the Eco RI-Nco I fragment of pKK233-2 (Pharmacia Biochemicals, Milwaukee, Wis.), was inserted into the Eco RI-Nco I restriction sites of plasmid p258 to produce plasmid p277. As a result, the p277 plasmid contained the $P_{TAC}$ (also known as $P_{TRC}$) promoter of pKK233-2, the lacZ ribosome binding site and an ATG initiation codon.

In the p277 plasmid, the insertion of a target protein sequence allows its transcription from an IPTG inducible promoter in an appropriate strain background. The appropriate strain background provides sufficient lac repressor protein to inhibit transcription from the uninduced $P_{TAC}$ promoter. Appropriate strains that can be used include JM101 or XL1-Blue. Because cells can be induced by the simple addition of small amounts of the chemical IPTG, the p277 plasmid provides a significant commercial advantage over promoters that require temperature shifts for induction. For example, induction by the $P_R$ promoter requires a temperature shift to inactivate the $C_1 857$ repressor inhibiting pJG200's $P_R$ promoter. Induction of commercial quantities of cell cultures containing temperature inducible promoters require the inconvenient step of heating large volumes of cells and medium to produce the temperature shift necessary for induction.

One additional benefit of the promoter change is that cells are not subjected to high temperatures or temperature shifts. High temperatures and temperature shifts result in a heat shock response and the induction of heat shock response proteases capable of degrading recombinant proteins as well as host proteins [See Grossman et al., 1984, Cell 38: 383; Baker et al., 1984, Proc. Natl. Acad. Sci. 81: 6779].

9.4. IMPROVEMENT OF THE RIBOSOME BINDING SITE

The p277 expression vector was further modified by insertion of twenty-nine base pairs, namely 5'CATGTATC-GATTAAATAAGGAGGAATAAC3' (SEQ ID NO 141) into the Nco I site of p277 to produce plasmid p340-1. This 29 bp sequence is related to, but different from, one portion of the Schoner "minicistron" sequence [Schoner et al., 1986, Proc. Nat'l. Acad. Sci. 83: 8506]. The inclusion of these 29 base pairs provides an optimum Shine/Dalgarno site for ribosomal/mRNA interaction. The p340-1 expression vector significantly differs from pJG200 because it contains a highly inducible promoter suitable for the high yields needed for commercial preparations, an improved synthetic ribosome binding site region to improve translation, and a means to provide a visual indicator of fragment insertion upon isolation. The steps in the construction of vector p340-1 are diagrammed in FIG. 16.

10. DEPOSIT OF MICROORGANISMS

The following plasmid was deposited with the American Type Culture Collection (ATCC), Rockville, Md. on Nov. 29, 1988, and has been assigned the indicated accession number:

| Plasmid | Accession Number |
|---------|------------------|
| p340    | ATCC 40516       |

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

It is also to be understood that all base pair and amino acid residue numbers and sizes given for nucleotides and peptides are approximate and are used for purposes of description.

A number of references are cited herein, the entire disclosures of which are incorporated herein, in their entirety, by reference.

What is claimed is:

1. A peptide which binds specifically to calmodulin and consisting of the amino acid sequence of SEQ ID NO 135.

2. A peptide which binds specifically to calmodulin, and consisting of an amino acid sequence which contains one or more substituted amino acids relative to the sequence of SEQ ID NO 135, in which each substituted amino acid is selected from a class of amino acids of similar polarity to the amino acid residue replaced by the substituted amino acid in SEQ ID NO 135.

3. A protein which binds specifically to calmodulin, and comprising the amino acid sequence of SEQ ID NO 135.

* * * * *